(12) United States Patent
Ganesh et al.

(10) Patent No.: US 11,572,559 B2
(45) Date of Patent: Feb. 7, 2023

(54) REDUCING BETA-CATENIN EXPRESSION TO POTENTIATE IMMUNOTHERAPY

(71) Applicant: Dicerna Pharmaceuticals, Inc., Lexington, MA (US)

(72) Inventors: Shanthi Ganesh, Shrewsbury, MA (US); Marc Abrams, Natick, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 569 days.

(21) Appl. No.: 16/497,310

(22) PCT Filed: Mar. 28, 2018

(86) PCT No.: PCT/US2018/024728
§ 371 (c)(1),
(2) Date: Sep. 24, 2019

(87) PCT Pub. No.: WO2018/183420
PCT Pub. Date: Oct. 4, 2018

(65) Prior Publication Data
US 2020/0377882 A1    Dec. 3, 2020

Related U.S. Application Data

(60) Provisional application No. 62/477,783, filed on Mar. 28, 2017.

(51) Int. Cl.
| | | |
|---|---|---|
| *C07H 21/04* | (2006.01) | |
| *C12N 15/113* | (2010.01) | |
| *A61P 35/02* | (2006.01) | |
| *A61P 35/00* | (2006.01) | |
| *A61K 9/51* | (2006.01) | |
| *A61K 39/395* | (2006.01) | |
| *A61K 47/69* | (2017.01) | |

(52) U.S. Cl.
CPC .......... *C12N 15/113* (2013.01); *A61K 9/5123* (2013.01); *A61K 9/5146* (2013.01); *A61K 39/39541* (2013.01); *A61K 47/6911* (2017.08); *A61P 35/00* (2018.01); *A61P 35/02* (2018.01); *C12N 2310/14* (2013.01); *C12N 2310/532* (2013.01); *C12N 2310/533* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 8,815,825 B2 | 8/2014 | Brown et al. | |
| 2013/0345286 A1* | 12/2013 | Gollob | A61P 35/00 514/44 A |
| 2018/0038868 A1* | 2/2018 | Gajewski | A61K 35/15 |

FOREIGN PATENT DOCUMENTS

| | | |
|---|---|---|
| WO | 2012/006243 A2 | 1/2012 |
| WO | 2012/018754 A2 | 2/2012 |
| WO | 2013/066721 A2 | 5/2013 |
| WO | 2016/141312 A1 | 9/2016 |
| WO | 2017/005773 A1 | 1/2017 |
| WO | 2017/011831 A1 | 1/2017 |
| WO | 2019/014398 A1 | 1/2019 |

OTHER PUBLICATIONS

Paul, S., and A. Dey. "Wnt signaling and cancer development: therapeutic implication Minireview." Neoplasma 55.3 (2008): 165-76.*
Spranger et al., "Melanoma-intrinsic β-catenin signalling prevents T cell infiltration and anti-tumor immunity", Journal for Immunotherapy of Cancer, Nov. 6, 2014, vol. 2 No. Suppl 3, 1 page.
Yee et al., "Adoptive T cell therapy using antigen-specific CD8+ T cell clones for the treatment of patients with metastatic melanoma: In vivo persistence, migration, and antitumor effect of transferred T cells", Proccedings of the National Academy of Sciences, Dec. 10, 2002, vol. 99, No. 25, pp. 16168-16173.
Ott et al., "CTLA-4 and PD-1/PD-L1 Blockade: New Immunotherapeutic Modalities with Durable Clinical Benefit in Melanoma Patients", Clinical Cancer Research, Oct. 1, 2013, vol. 19, No. 19, pp. 5300-5309.
Gajewski et al., "Cancer immunotherapy strategies based on overcoming barriers within the tumor microenvironment", Current Opinion in Immunology, Apr. 1, 2013, vol. 25, No. 2, pp. 268-276.
Extended European Search Report dated Dec. 16, 2020 from corresponding European Patent Application No. 18774640.9, 13 pages.
International Search Report and Written Opinion dated May 31, 2018 for International Application No. PCT/US2018/024728, 12 pages.
Deng et al., "β-catenin interacts with and inhibits NF-κB in human colon and breast cancer", Cancer Cell, Oct. 2002, vol. 2, pp. 323-334.

(Continued)

*Primary Examiner* — Kimberly Chong
(74) *Attorney, Agent, or Firm* — MH2 Technology Law Group, LLP

(57) ABSTRACT

Provided herein are methods and compositions for treating cancer, including cancer that is not responsive to immunotherapy. In one aspect, the methods of treatment comprise administering to the subject a therapeutically effective amount of a β-catenin inhibitor and a therapeutically effective amount of an immunotherapeutic agent. Another aspect is directed to pharmaceutical compositions comprising a β-catenin inhibitor for use in treating cancer, wherein the composition is administered in combination with an immunotherapeutic agent. Yet another aspect is directed to a method of potentiating the therapeutic effect of immunotherapy against a cancer using a β-catenin inhibitor, such as a β-catenin nucleic acid inhibitor molecule.

29 Claims, 34 Drawing Sheets

Specification includes a Sequence Listing.

(56) References Cited

OTHER PUBLICATIONS

Gajewski et al., "Innate and adaptive immune cells in the tumor microenvironment", Nat Immunol., Oct. 2013, vol. 14, No. 10, pp. 1014-1022.

Ganesh et al., "Direct Pharmacological Inhibition of β-Catenin by RNA Interference in Tumors of Diverse Origin", Molecular Cancer Therapeutics, Sep. 2016, vol. 15, No. 9, 12 pages.

Huang et al., "VEGF suppresses T-lymphocyte infiltration in the tumor microenvironment through inhibition of NF-κB-induced endothelial activation", The FASEB Journal, Jan. 2015, vol. 29, No. 1, pp. 227-238.

Ji et al., "An immune-active tumor microenvironment favors clinical response to ipilimumab", Cancer Immunol Immunother, 2012, vol. 61, pp. 1019-1031.

Kawakami et al., "Improvement of cancer immunotherapy by combining molecular targeted therapy", Frontiers in Oncology, May 2013, vol. 3, Article 136, 7 pages.

Ma et al., "Crosstalk between Wnt/β-Catenin and NF-κB Signaling Pathway during Inflammation", Frontiers in Immunology, Sep. 2016, vol. 7, Article 378, 14 pages.

Muthuswamy et al., "NF-κB hyper-activation in tumor tissues allows tumor-selective reprogramming of chemokine microenvironment to enhance the recruitment of cytolytic T effector cells", Cancer Research, Aug. 1, 2012; vol. 72, No. 15, pp. 3735-3743.

Ott et al., "Impact of MAPK pathway activation in BRAFV600 melanoma on T cell and dendritic cell function", Frontiers in Immunology, Oct. 2013, vol. 4, Article 346, 7 pages.

Scholer-Dahirel et al., "Maintenance of adenomatous polyposis coli (APC)-mutant colorectal cancer is dependent on Wnt/β-catenin signaling", PNAS, Oct. 2011, vol. 108, No. 41, pp. 17135-17140.

Segditsas et al., "Colorectal cancer and genetic alterations in the Wnt pathway", Oncogene, 2006, vol. 25, pp. 7531-7537.

Spranger et al., "Melanoma-intrinsic β-catenin signalling prevents anti-tumour immunity", Nature, Jul. 9, 2015, vol. 523, pp. 231-248.

Spranger et al., "Supplementary Information", Nature, Jul. 9, 2015, vol. 523, 113 pages.

Spranger et al., "A new paradigm for tumor immune escape: β-catenin-driven immune exclusion", Journal for ImmunoTherapy of Cancer, 2015, vol. 3, No. 43, 3 pages.

Spranger et al., "Tumor-intrinsic oncogene pathways mediating immune avoidance", Oncoimmunology 2016, vol. 5, No. 3, e1086862, 7 pages.

Webster et al., "The Wnts of Change: How Wnts Regulate Phenotype Switching in Melanoma", Biochim Biophys Acta., Dec. 2015, vol. 1856, No. 2, pp. 244-251.

Yaguchi et al., "Immune Suppression and Resistance Mediated by Constitutive Activation of Wnt/β-Catenin Signaling in Human Melanoma Cells", The Journal of Immunology, 2012, vol. 189, pp. 2110-2117.

\* cited by examiner

| TUMOR MODEL | TISSUE/TUMOR TYPE | MODEL TYPE | NUCLEAR β-CATENIN | EFFICACY OF β-CATENIN INHIBITION | |
|---|---|---|---|---|---|
| | | | | MONOTHERAPY | COMBINATION WITH IMMUNOTHERAPY |
| B16F10 | MELANOMA | SYNGENEIC ALLOGRAFT | NO | NO | YES |
| NEURO2A | NEUROBLASTOMA | SYNGENEIC ALLOGRAFT | NO | NO | YES |
| RENCA | RENAL CELL CARCINOMA | SYNGENEIC ALLOGRAFT | NO | NO | YES |
| 4T1 | MAMMARY | SYNGENEIC ALLOGRAFT | YES | YES | YES |
| MMTV-WNT | MAMMARY | GEMM (SPONTANEOUS TUMOR) | YES | YES | YES |

FIG. 2B

PASSENGER STRAND (SENSE)

5' AGAAUACAAAUGAUGUAGAAACAGCC 3'

3' CGUCUUAUGUUUACUACAUCUUUGUCGGTGCUAUCGAU 5'

GUIDE STRAND (ANTISENSE)

REDUCING BETA-CATENIN EXPRESSION TO POTENTIATE IMMUNOTHERAPY

CROSS-REFERENCE TO RELATED APPLICATIONS

This application is a U.S. National Stage application of PCT/US2018/024728 filed 28 Mar. 2018, which claims the benefit of, and relies on the filing date of, U.S. provisional patent application No. 62/477,783, filed 28 Mar. 2017, the entire disclosure of which is incorporated herein by reference.

SEQUENCE LISTING

The instant application contains a Sequence Listing which has been filed electronically in ASCII format and is hereby incorporated by reference in its entirety. Said ASCII copy, created on Mar. 23, 2018, is named 0243_0007-PCT_SL.txt and is 2 kilobytes in size.

BACKGROUND

The immune system uses certain molecules on the surface of immune cells as checkpoints to control T cell activation and prevent the immune system from targeting healthy cells and inducing autoimmunity. Certain cancer cells are able to take advantage of these immune checkpoint molecules to evade the immune system. In recent years, immunotherapeutic strategies to block immune checkpoint molecules, such as cytotoxic T-lymphocyte-associated protein-4 (CTLA-4) and programmed cell death receptor 1 (PD-1), have shown success against certain cancers. An anti-CTLA-4 monoclonal antibody (ipilimumab) was approved for the treatment of patients with advanced melanoma in 2011. An anti-PD-1 monoclonal antibody (nivolumab) was approved for the treatment of patients with certain advanced cancers in 2014, alone or in combination with ipilimumab. Antibodies that block immune checkpoint molecules like CTLA-4, PD-1, and PD-L1 appear to release the brakes on T cell activation and promote potent anti-tumor immune responses. However, only a subset of patients respond to this immunotherapy.

At least in certain instances, the tumors that respond to immunotherapy have a pre-existing T cell inflamed phenotype, with infiltrating T cells, a broad chemokine profile that recruits T cells to the tumor microenvironment, and high levels of IFN gamma secretion (also called hot or inflamed tumors). Gajewski et al., Nat Immunol., 2013, 14(10):1014-22; Ji et al., Cancer Immunol Immunother, 2012, 61:1019-31. Conversely, certain tumors that do not respond to immunotherapy have been shown to not have a T cell inflamed phenotype (also known as cold or non-inflamed tumors). Id.

There remains a need in the art to develop new cancer treatment options, including options that would make non-inflamed tumors responsive to immunotherapy.

SUMMARY

Typically, cancer that is not responsive to immunotherapy is characterized by a non-T cell inflamed phenotype (also known as cold or non-inflamed tumors), with little to no infiltrating CD8+ T cells in the tumor microenvironment. This application discloses that reducing β-catenin expression can convert a cold or non-inflamed tumor into a hot or inflamed tumor and potentiate the effect of immunotherapy, even in tumors that do not have an activated Wnt/β-catenin pathway. In other words, by combining a β-catenin inhibitor with immunotherapy, it is possible to treat cold or non-inflamed tumors that normally do not respond to immunotherapy. Typically, a β-catenin nucleic acid inhibitor molecule is used to reduce β-catenin expression including, but not limited to, short interfering RNA (siRNA), conventional antisense oligonucleotides, microRNA (miRNA), ribozymes, and aptamers. However, any β-catenin inhibitor or Wnt/β-catenin pathway inhibitor that reduces β-catenin expression can be used in the methods and compositions described herein, including, but not limited to small molecules, peptides, and antibodies that target β-catenin or a component of the Wnt/β-catenin pathway. This combination therapy approach has been shown to potently, and in many instances synergistically, inhibit tumor growth in vivo across a broad variety of cancers, including cancers with and without an activated Wnt/β-catenin pathway.

One aspect is directed to a method of treating cancer in a subject, comprising administering to the subject a therapeutically effective amount of a β-catenin inhibitor and a therapeutically effective amount of an immunotherapeutic agent. In certain embodiments, the cancer is a non-Wnt activated cancer. In other embodiments, the cancer is a Wnt activated cancer. In certain embodiments, the subject is a human.

In certain embodiments, the immunotherapeutic agent is an antagonist of an inhibitory immune checkpoint molecule or an agonist of a co-stimulatory checkpoint molecule. In certain embodiments, the immunotherapeutic agent is an antagonist of an inhibitory check point, and the inhibitory check point is PD-1 or PD-L1. In certain embodiments, the antagonist of the inhibitory immune checkpoint molecule or the agonist of the co-stimulatory checkpoint molecule is a monoclonal antibody. In certain embodiments, the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

In certain embodiments, the method of treating cancer in a human subject, comprises administering to the human subject:
a therapeutically effective amount of a β-catenin nucleic acid inhibitor molecule, wherein the β-catenin nucleic acid inhibitor molecule is a double stranded RNAi inhibitor molecule comprising a sense and an antisense strand and a region of complementarity between the sense strand and the antisense strand of 18-34 base pairs, wherein the sense strand is 18-36 nucleotides in length and the antisense strand is 18-38 nucleotides in length and comprises 1-5 single-stranded nucleotides at its 3' terminus; and
a therapeutically effective amount of an immunotherapeutic agent, wherein the immunotherapeutic agent comprises an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody. In certain embodiments, the sense strand is 25-35 nucleotides in length and the antisense strand is 26-38 nucleotides in length.

In certain embodiments, the cancer is a non-Wnt activated cancer. In other embodiments, the cancer is a Wnt activated cancer.

In certain embodiments, the subject has been identified as having the non-Wnt activated cancer before the administering step.

In certain embodiments, the method further comprises before the administering step, a step of analyzing a tumor sample from the subject to determine if the subject has the non-Wnt activated cancer.

Another aspect is directed to a method of potentiating a therapeutic effect of an immunotherapeutic agent against a cancer, comprising administering to a subject having the cancer a β-catenin nucleic acid inhibitor molecule in an amount sufficient to potentiate the therapeutic effect of the immunotherapeutic agent against the cancer. In certain embodiments, the cancer is a non-Wnt activated cancer. In other embodiments, the cancer is a Wnt activated cancer.

In certain embodiments, prior to administering the β-catenin nucleic acid inhibitor molecule, the cancer is associated with a non-T cell inflamed phenotype that is resistant to immunotherapy and wherein administering the β-catenin nucleic acid inhibitor molecule converts the non-T cell inflamed phenotype into a T cell-inflamed phenotype that is responsive to an immunotherapeutic agent.

Another aspect is directed to a pharmaceutical composition comprising a β-catenin inhibitor for use in treating cancer, wherein the composition is administered in combination with an immunotherapeutic agent.

In one embodiment, the pharmaceutical composition comprises a β-catenin nucleic acid inhibitor molecule for use in treating cancer, wherein the composition is administered in combination with an immunotherapeutic agent, wherein the β-catenin nucleic acid inhibitor molecule is a double stranded RNAi inhibitor molecule comprising a sense and an antisense strand and a region of complementarity between the sense strand and the antisense strand of 18-34 base pairs, wherein the sense strand is 19-36 nucleotides in length and the antisense strand is 19-38 nucleotides in length and comprises 1-5 single-stranded nucleotides at its 3' terminus, and wherein the immunotherapeutic agent is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody. In certain embodiments, the sense strand is 25-34 nucleotides in length and the antisense strand is 26-38 nucleotides in length. In certain embodiments, the cancer is a non-Wnt activated cancer. In other embodiments, the cancer is a Wnt activated cancer.

In certain embodiments of the methods or compositions, the non-Wnt activated cancer is resistant to treatment with the immunotherapeutic agent when the immunotherapeutic agent is not administered in combination with the β-catenin nucleic acid inhibitor molecule.

In certain embodiments of the methods or compositions, the non-Wnt activated cancer is a melanoma, a neuroblastoma, or a renal cancer.

In certain embodiments of the methods or compositions, the β-catenin inhibitor is a β-catenin nucleic acid inhibitor molecule, including, but not limited to, siRNA, conventional antisense oligonucleotides, miRNA, ribozymes, and aptamers. In certain embodiments of the methods or compositions, the β-catenin nucleic acid inhibitor molecule is a double stranded RNAi inhibitor molecule comprising a sense strand and an antisense strand that form a region of complementarity, optionally wherein the region of complementarity between the sense strand and the antisense strand is about 15-45 base pairs.

In certain embodiments of the methods or compositions, the β-catenin nucleic acid inhibitor molecule is a double stranded RNAi inhibitor molecule comprising a sense stand and an antisense strand and a region of complementarity between the sense strand and the antisense strand of about 15-45, 18-26, or 19-21 base pairs. In certain embodiments, the sense strand is 15-66 nucleotides and the antisense strand is 15-66 nucleotides. In certain embodiments, the sense strand is 25-40 nucleotides or 19-25 nucleotides. In certain embodiments, the antisense strand is 25-40 nucleotides or 19-25 nucleotides. In certain embodiments, the sense strand is 19-25 nucleotides and the antisense strand is 19-25 nucleotides.

In certain embodiments of the methods or compositions, the β-catenin nucleic acid inhibitor molecule contains a tetraloop. In certain embodiments, the sense strand is 34-40 nucleotides and contains a stem and tetraloop and the antisense strand is 18-24 nucleotides, wherein the sense strand and antisense strand form a duplex region of 18-24 base pairs. In certain embodiments, the sense strand is 34-36 nucleotides and contains a stem and tetraloop, and the antisense strand is 18-24 nucleotides, wherein the sense strand and antisense strand form a duplex region of 18-24 base pairs.

In certain embodiments of the methods or compositions, the β-catenin nucleic acid inhibitor molecule is a double stranded RNAi inhibitor molecule comprising a sense and an antisense strand and a region of complementarity between the sense strand and the antisense strand of 18-36 base pairs, wherein the sense strand is 25-34 nucleotides in length and the antisense strand is 26-38 nucleotides in length and comprises a single-stranded overhang of 1-5 nucleotides at its 3' terminus. In certain embodiments, the sense strand is 18-34 nucleotides in length. In certain embodiments, the antisense strand of the double stranded RNAi inhibitor molecule further comprises a single-stranded overhang of 1-10 nucleotides at its 5' terminus.

In certain embodiments of the methods or compositions, the β-catenin nucleic acid inhibitor molecule is a double stranded RNAi inhibitor molecule comprising a sense and an antisense strand and a region of complementarity between the sense strand and the antisense strand of 20-30, 21-26, 19-24, or 19-21 base pairs. In certain embodiments, the sense strand has 21 nucleotides and includes a single-stranded overhang of 2 nucleotides at its 3' terminus, the antisense strand is 21 nucleotides and has a single-stranded overhang of 2 nucleotides at its 3' end, and sense strand and antisense strand form a duplex region of 19 base pairs. In certain embodiments, the sense strand is 21 nucleotides, the antisense strand is 23 nucleotides and has a single-stranded overhang of 2 nucleotides at its 3' end, sense strand and antisense strand form a duplex region of 21 base pairs, and the 3' end of the sense strand and the 5' end of the antisense strand form a blunt end.

In certain embodiments of the methods or compositions, the region of complementarity between the sense strand and the antisense strand is 21-26 base pairs, wherein the sense strand is 21-26 nucleotides in length and wherein the antisense strand is 23-38 nucleotides in length and includes a single-stranded overhang of 1-2 nucleotides at its 3' terminus. In certain embodiments, the antisense strand further comprises a single-stranded overhang of 1-10 nucleotides at its 5' terminus.

In certain embodiments of the methods or compositions, the β-catenin nucleic acid inhibitor molecule is a double stranded RNAi inhibitor molecule comprising a sense and an antisense strand and a region of complementarity between the sense strand and the antisense strand of 26 base pairs, wherein the sense strand is 26 nucleotides in length and wherein the antisense strand is 38 nucleotides in length and includes a single-stranded overhang of 2 nucleotides at its 3' terminus and a single-stranded overhang of 10 nucleotides at its 5' terminus.

In certain embodiments of the double stranded RNAi inhibitor molecule, the sense strand comprises or consists of the sequence of SEQ ID NO: 1. In certain embodiments of the double stranded RNA inhibitor molecule, the antisense strand comprises or consists of the sequence of SEQ ID NO: 2.

In certain embodiments of the methods or compositions, the β-catenin nucleic acid inhibitor molecule is a single-stranded oligonucleotide. In certain embodiments of the method or composition, the β-catenin nucleic acid inhibitor molecule is a conventional antisense oligonucleotide that has a nucleotide sequence in the 5' to 3' direction that comprises the reverse complement of a segment of a human β-catenin gene and is 12-30, 12-25, 12-22, 14-20, or 18-22 nucleotides in length. In certain embodiments, the conventional antisense oligonucleotide is 16-18 or 18-20 nucleotides in length.

In certain embodiments of the methods or compositions, the β-catenin nucleic acid inhibitor molecule is formulated with a lipid nanoparticle. In certain embodiments, the lipid nanoparticle comprises a cationic lipid and a pegylated lipid.

In certain embodiments of the methods or compositions, the immunotherapeutic agent is an antagonist of an inhibitory immune checkpoint molecule or an agonist of a co-stimulatory checkpoint molecule. In certain embodiments, the immunotherapeutic agent is an antagonist of an inhibitory check point, and the inhibitory checkpoint is PD-1 or PD-L1. In certain embodiments, the antagonist of the inhibitory immune checkpoint molecule or the agonist of the co-stimulatory checkpoint molecule is a monoclonal antibody. In certain embodiments, the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

In other embodiments, the immunotherapeutic agent is an antagonist of an inhibitory immune checkpoint molecule, wherein the inhibitory immune checkpoint molecule is a ligand for PD-1, such as PD-L1 or PD-L2; a ligand for CTLA4, such as CD80 or CD86; or a lymphocyte activation gene 3 (LAG3), killer cell immunoglobulin like receptor (KIR), T cell membrane protein 3 (TIM3), galectin 9 (GAL9), or adenosine A2a receptor (A2aR). In certain embodiments, the immunotherapeutic agent is an agonist of a co-stimulatory molecule, wherein the co-stimulatory molecule is CD28, inducible T cell co-stimulator (ICOS), CD137, OX40, or CD27. In other embodiments, the immunotherapeutic agent is an agonist of a ligand of a co-stimulatory molecule, including, for example, CD80, CD86, B7RP1, B7-H3, B7-H4, CD137L, OX40L, or CD70.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 2B is a table summarizing the tissue/tumor type, model type, nuclear β-catenin staining, and efficacy of β-catenin inhibition as monotherapy or in combination with immunotherapy for B16F10, Neuro2A, Renca, 4T1, and MMTV-Wnt.

DEFINITIONS

Figure 1:
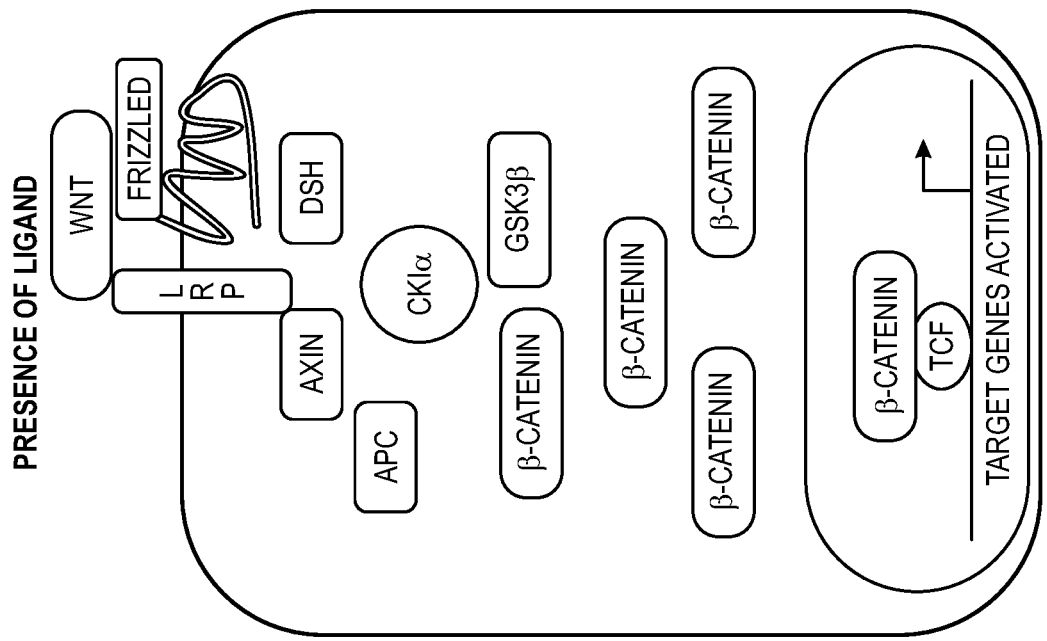
FIG. 1 shows a simplified diagram of the Wnt signaling pathway. The left side depicts a cell where the Wnt ligand is not bound to its surface receptor, β-catenin is sequestered in a destruction complex and targeted for ubiquitination and degradation, and target genes are repressed. The right side depicts a cell after the Wnt ligand has bound its surface receptor, where the destruction complex disassembles, stabilized β-catenin is released and travels to the nucleus, and target genes are activated.
Figure 1:
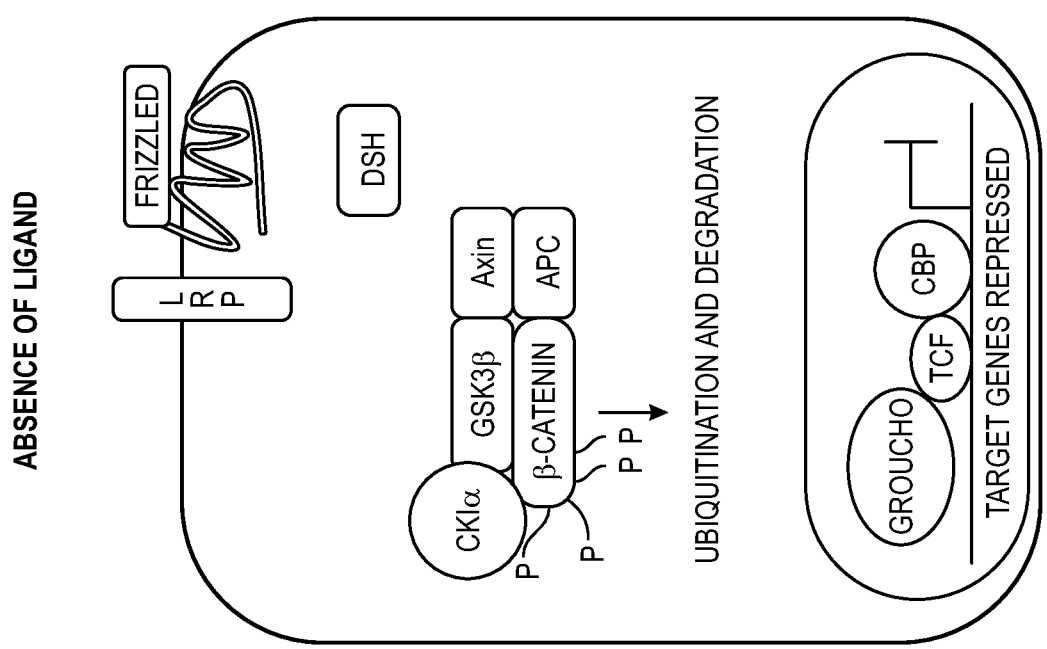

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Antibody: As used herein, the term "antibody" refers to an immunoglobulin or an antigen-binding domain thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

Antigen-Binding Domain: As used herein, the term "antigen-binding domain" refers to a part of an antibody molecule that comprises amino acids responsible for the specific binding between antibody and antigen. For certain antigens, the antigen-binding domain may only bind to a part of the antigen. The part of the antigen that is specifically recognized and bound by the antibody is referred to as the "epitope" or "antigenic determinant." Antigen-binding domains include Fab (Fragment antigen-binding); a F(ab')2 fragment, a bivalent fragment having two Fab fragments linked by a disulfide bridge at the hinge region; Fv fragment; a single chain Fv fragment (scFv) see e.g., Bird et al. (1988) Science 242:423-426; and Huston et al. (1988) Proc. Natl. Acad. Sci. USA 85:5879-5883); a Fd fragment having the two $V_H$ and $C_H1$ domains; dAb (Ward et al., (1989) Nature 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ peptide may be used as a linker, but other linkers are known in the art. These antibody fragments are obtained using conventional techniques known to those with skill in the art, and the fragments are evaluated for function in the same manner as are intact antibodies.

Antisense strand: A dsRNAi inhibitor molecule comprises two oligonucleotide strands: an antisense strand and a sense strand. The antisense strand or a region thereof is partially, substantially or fully complementary to a corresponding region of a target nucleic acid. In addition, the antisense strand of the dsRNAi inhibitor molecule or a region thereof is partially, substantially or fully complementary to the sense strand of the dsRNAi inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a dsRNAi inhibitor molecule is also referred to as the guide strand.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

β-catenin: As used herein, "β-catenin" refers either to a polypeptide or a nucleic acid sequence encoding such a β-catenin protein. When referring to a polypeptide, "β-catenin" refers to the polypeptide gene product of a β-catenin gene/transcript (CTNNB1) (Genbank Accession Nos. NM_001904.3 (human β-catenin transcript variant 1), NM_001098209.1 (human β-catenin transcript variant 2), NM_001098210.1 (human β-catenin transcript variant 3), and NM_007614.2 & NM_007614.3 (mouse β-catenin).

BCAT1: As used herein "BCAT1" refers to a nucleic acid inhibitor molecule that targets the β-catenin gene and has a sense strand with a nucleic acid sequence consisting of SEQ ID NO:1 and an antisense strand with a nucleic acid sequence consisting of SEQ ID NO:2.

Complementary. As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementary" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double stranded nucleic acid inhibitor molecule that is partially, substantially or fully complementary to the other strand.

Conventional antisense oligonucleotide: As used herein, the term "conventional antisense oligonucleotide" refers to single stranded oligonucleotides that inhibit the expression of a targeted gene by one of the following mechanisms: (1) Steric hindrance, e.g., the antisense oligonucleotide interferes with some step in the sequence of events involved in gene expression and/or production of the encoded protein by directly interfering with, for example, transcription of the gene, splicing of the pre-mRNA and translation of the mRNA; (2) Induction of enzymatic digestion of the RNA transcripts of the targeted gene by RNase H; (3) Induction of enzymatic digestion of the RNA transcripts of the targeted gene by RNase L; (4) Induction of enzymatic digestion of the RNA transcripts of the targeted gene by RNase P: (5) Induction of enzymatic digestion of the RNA transcripts of the targeted gene by double stranded RNase; and (6) Combined steric hindrance and induction of enzymatic digestion activity in the same antisense oligo. Conventional antisense oligonucleotides do not have an RNAi mechanism of action like RNAi inhibitor molecules. RNAi inhibitor molecules can be distinguished from conventional antisense oligonucleotides in several ways including the requirement for Ago2 that combines with an RNAi antisense strand such that the antisense strand directs the Ago2 protein to the intended target(s) and where Ago2 is required for silencing of the target.

Deoxyribonucleotide: As used herein, the term "deoxyribonucleotide" refers to a natural nucleotide (as defined herein) or a modified nucleotide (as defined herein), which has a hydrogen group at the 2'-position of the sugar moiety.

Duplex: As used herein, the term "duplex," in reference to nucleic acids (e.g., oligonucleotides), refers to a structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Immune checkpoint molecules: As used herein, the term "immune checkpoint molecule" refers to molecules on immune cells, such as T cells, that are important under normal physiological conditions for the maintenance of self-tolerance (or the prevention of autoimmunity) and the protection of host cells and tissue when the immune system responds to a foreign pathogen. Certain immune checkpoint molecules are co-stimulatory molecules that amplify a signal involved in the T cell response to antigen while certain immune checkpoint molecules are inhibitory molecules (e.g., CTLA-4 or PD-1) that reduce a signal involved in the T cell response to antigen.

Loop: As used herein, the term "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins and tetraloops.

Modified nucleoside: As used herein, the term "modified nucleoside" refers to a nucleoside containing one or more of a modified or universal nucleobase or a modified sugar. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2'-, 3'-, 4'-, or 5'-carbon position of the sugar. The modified sugar may also include non-natural alternative carbon structures such as those present in locked nucleic acids ("LNA") (see, e.g., Koshkin et al. (1998), Tetrahedron, 54,3607-3630) bridged nucleic acids ("BNA") (see, e.g., U.S. Pat. No. 7,427,672 and Mitsuoka et al. (2009), Nucleic Acids Res., 37(4):1225-38); and unlocked nucleic acids ("UNA") (see, e.g., Snead et al. (2013), Molecular Therapy—Nucleic Acids, 2, e103(doi: 10.1038/mtna.2013.36)). Suitable modified or universal nucleobases or modified sugars in the context of the present disclosure are described herein.

Modified nucleotide: As used herein, the term "modified nucleotide" refers to a nucleotide containing one or more of a modified or universal nucleobase, a modified sugar, or a modified phosphate group. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2'-, 3'-, 4'-, or 5'-carbon position of the sugar. The modified sugar may also include non-natural alternative carbon structures such as those present in locked nucleic acids ("LNA") (see, e.g., Koshkin et al. (1998), Tetrahedron, 54,3607-3630); bridged nucleic acids ("BNA") (see, e.g., U.S. Pat. No. 7,427,672 and Mitsuoka et al. (2009), Nucleic Acids Res., 37(4):1225-38); and unlocked nucleic acids ("UNA") (see, e.g., Snead et al. (2013), Molecular Therapy—Nucleic Acids, 2, e103(doi: 10.1038/mtna.2013.36)). Modified phosphate groups refer to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups and non-phosphorous containing linking groups, as described herein. Suitable modified or universal nucleobases, modified sugars, or modified phosphates in the context of the present disclosure are described herein.

Naked oligonucleotide: As used herein, the term "naked oligonucleotide" refers to an oligonucleotide that is not formulated in a protective lipid nanoparticle or other protective formulation and is thus exposed to the blood and endosomal/lysosomal compartments when administered in vivo.

Natural nucleoside: As used herein, the term "natural nucleoside" refers to a heterocyclic nitrogenous base in N-glycosidic linkage with a sugar (e.g., deoxyribose or ribose or analog thereof). The natural heterocyclic nitrogenous bases include adenine, guanine, cytosine, uracil and thymine.

Natural nucleotide: As used herein, the term "natural nucleotide" refers to a heterocyclic nitrogenous base in N-glycosidic linkage with a sugar (e.g., ribose or deoxyribose or analog thereof) that is linked to a phosphate group. The natural heterocyclic nitrogenous bases include adenine, guanine, cytosine, uracil and thymine.

non-T cell inflamed phenotype: As used herein, "non-T cell inflamed phenotype" refers to a tumor microenvironment without a pre-existing T cell response against the tumor, as evidenced by little to no accumulation of infiltrating CD8+ T cells in the tumor microenvironment. Typically, the non-T cell inflamed phenotype is also characterized by a limited chemokine profile that does not promote the recruitment and accumulation of CD8+ T cells in the tumor microenvironment and/or a minimal or absent type I IFN gene signature.

non-Wnt activated disease or disorder: As used herein, a "non-Wnt activated" disease or disorder refers to a disease or disorder that is not associated with activation of the Wnt/β-catenin pathway. A "non-Wnt activated" disease or disorder includes certain cancer and/or proliferative diseases, conditions, or disorders, including certain colorectal, desmoid, endometrial, gastric, hepatocellular, hepatoblastoma, kidney (Wilms' tumor), medulloblastoma, melanoma, neuroblastoma, ovarian (endometrioid), pancreatic, pilomatricoma, prostate, renal, thyroid (anaplastic) and uterine (endometrium) cancers. In one embodiment, the "non-Wnt activated" disease or disorder is colorectal cancer, hepatocellular carcinoma, or melanoma. In one embodiment, the "non-Wnt activated" disease or disorder is neuroblastoma, renal cancer, or melanoma. It is understood that a disease or disorder, including the cancer and/or proliferative diseases listed above, may include both a non-Wnt activated sub-type of the disease or disorder and a Wnt activated sub-type of the disease or disorder, consistent with the definition of Wnt activated disease or disorder provided below.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleoside: As used herein, the term "nucleoside" refers to a natural nucleoside or a modified nucleoside.

Nucleotide: As used herein, the term "nucleotide" refers to a natural nucleotide or a modified nucleotide.

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that are capable of forming a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of a β-catenin nucleic acid inhibitor molecule or an immunotherapeutic agent, such as an antibody (including, for example, one or more of an anti-CTLA-4, anti-PD-1, or anti-PD-L1 antibody) and a pharmaceutically acceptable excipient. As used herein, "pharmacologically effective amount," "therapeutically effective amount" or "effective amount" refers to that amount of a β-catenin nucleic acid inhibitor molecule or an immunotherapeutic agent, such as an antibody (including, for example, one or more of an anti-CTLA-4, anti-PD-1, or anti-PD-L1 antibody) effective to produce the intended pharmacological, therapeutic or preventive result.

Pharmaceutically acceptable excipient: The phrase "pharmaceutically acceptable excipient" means that the excipient is one that is suitable for use with humans and/or animals without undue adverse side effects (such as toxicity, irritation, and allergic response) commensurate with a reasonable benefit/risk ratio.

Phosphate mimic: As used herein, the term "phosphate mimic" refers to a chemical moiety at the 5'-terminal end of an oligonucleotide that mimics the electrostatic and steric properties of a phosphate group. Many phosphate mimics have been developed that can be attached to the 5'-end of an oligonucleotide (see, e.g., U.S. Pat. No. 8,927,513; Prakash et al. *Nucleic Acids Res.*, 2015,43(6):2993-3011). Typically, these 5'-phosphate mimics contain phosphatase-resistant linkages. Suitable phosphate mimics include 5'-phosphonates, such as 5'-methylenephosphonate (5'-MP) and 5'-(E)-vinylphosphonate (5'-VP) and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate, as described in International Publication No. WO 2018/045317, which is hereby incorporated by reference in its entirety. In certain embodiments, the 4'-oxymethylphosphonate is represented by the formula —O—$CH_2$—$PO(OH)_2$ or —O—$CH_2$—$PO(OR)_2$, where R is independently selected from H, $CH_3$, an alkyl group, or a protecting group. In certain embodiments, the alkyl group is $CH_2CH_3$. More typically, R is independently selected from H, $CH_3$, or $CH_2CH_3$. Other modifications have been developed for the 5'-end of oligonucleotides (see, e.g., WO 2011/133871).

Potentiate: The term "potentiate" or "potentiating" as used herein refers to the ability of one therapeutic agent (e.g., a β-catenin nucleic acid inhibitor molecule) to increase or enhance the therapeutic effect of another therapeutic agent (e.g., an antagonist of an inhibitory immune checkpoint molecule, such as CTLA-4 or PD-1, or an agonist of a co-stimulatory checkpoint molecule).

Reduce(s): The term "reduce" or "reduces" as used herein refers to its meaning as is generally accepted in the art. With reference to exemplary nucleic acid inhibitor molecules (e.g., β-catenin RNAi inhibitor molecules), the term generally refers to the reduction in the expression of a gene, or level of RNA molecules or equivalent RNA molecules encoding one or more proteins or protein subunits, or activity of one or more proteins or protein subunits, below that observed in the absence of the nucleic acid inhibitor molecules.

Resistance: The term "resistance" or "resistant" as used in relation to immunotherapy refers to a cancer and/or proliferative disease, condition or disorder that does not show a medically significant response to immunotherapy. As disclosed herein, resistance to immunotherapy can be reversed by reducing β-catenin expression.

Ribonucleotide: As used herein, the term "ribonucleotide" refers to a natural or modified nucleotide which has a hydroxyl group at the 2'-position of the sugar moiety.

RNAi inhibitor molecule: As used herein, the term "RNAi inhibitor molecule" refers to either (a) a double stranded nucleic acid inhibitor molecule ("dsRNAi inhibitor molecule") having a sense strand (passenger) and antisense strand (guide), where the antisense strand or part of the antisense strand is used by the Argonaute 2 (Ago2) endonuclease in the cleavage of a target mRNA or (b) a single stranded nucleic acid inhibitor molecule ("ssRNAi inhibitor molecule") having a single antisense strand, where the antisense strand (or part of the antisense strand) is used by the Ago2 endonuclease in the cleavage of a target mRNA.

Sense strand: A dsRNAi inhibitor molecule comprises two oligonucleotide strands: an antisense strand and a sense strand. The sense strand or a region thereof is partially, substantially or fully complementary to the antisense strand of the dsRNAi inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Subject: As used herein, the term "subject" means any mammal, including mice, rabbits, and humans. In one embodiment, the subject is a human. The terms "individual" or "patient" are intended to be interchangeable with "subject."

T cell-inflamed tumor phenotype: As used herein, "T cell-inflamed phenotype" refers to a tumor microenvironment with a pre-existing T cell response against the tumor, as evidenced by an accumulation of infiltrating CD8+ T cells in the tumor microenvironment. Typically, the T cell-inflamed phenotype is also characterized by a broad chemokine profile capable of recruiting CD8+ T cells to the tumor microenvironment (including CXCL9 and/or CXCL10) and/or a type I IFN gene signature.

Tetraloop: As used herein, the term "tetraloop" refers to a loop (a single stranded region) that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the nucleotides in a tetraloop include but are not limited to non-Watson-Crick base pairing, stacking interactions, hydrogen bonding, and contact interactions (Cheong et al., Nature, 1990, 346(6285):680-2; Heus and Pardi, Science, 1991, 253(5016):191-4). A tetraloop confers an increase in the melting temperature (Tm) of an adjacent duplex that is higher than expected from a simple model loop sequence consisting of random bases. For example, a tetraloop can confer a melting temperature of at least 50° C., at least 55° C., at least 56° C., at least 58° C., at least 60° C., at least 65° C. or at least 75° C. in 10 mM NaHPO4 to a hairpin comprising a duplex of at least 2 base pairs in length. A tetraloop may contain ribonucleotides, deoxyribonucleotides, modified nucleotides, and combinations thereof. In certain embodiments, a tetraloop consists of four nucleotides. In certain embodiments, a tetraloop consists of five nucleotides.

Examples of RNA tetraloops include the UNCG family of tetraloops (e.g., UUCG), the GNRA family of tetraloops (e.g., GAAA), and the CUUG tetraloop. (Woese et al., PNAS, 1990, 87(21):8467-71; Antao et al., Nucleic Acids Res., 1991, 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). (Nakano et al. Biochemistry, 2002, 41(48):14281-14292. Shinji et al., Nippon Kagakkai Koen Yokoshu, 2000, 78(2):731).

Therapeutically effective amount: As used herein, a "therapeutically effective amount" or "pharmacologically effective amount" means an amount of compound or compounds effective to prevent, alleviate or ameliorate disease or condition symptoms of the subject being treated.

Wnt activated disease or disorder. As used herein, a "Wnt activated" disease or disorder refers to a disease or disorder that is associated with an activated Wnt/β-catenin pathway. A "Wnt-associated" disease or disorder includes cancer and/or proliferative diseases, conditions, or disorders, including colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers. In one embodiment, the "Wnt activated" disease or disorder is colorectal cancer, hepatocellular carcinoma, or melanoma. It is understood that a disease or disorder, including the cancer and/or proliferative diseases listed above, may include both a Wnt activated version of the disease or disorder and a non-Wnt activated version of the disease or disorder, consistent with the definition of non-Wnt activated disease or disorder provided above.

Wnt/β-catenin pathway: As used herein the "Wnt/β-catenin pathway" refers to a molecular signaling pathway in cells that is mediated through a combination of Wnt ligands, receptors, and co-receptors, which initiate a downstream signaling pathway that involves β-catenin (see e.g., FIG. 1). In the absence of Wnt signaling, β-catenin is targeted for degradation via ubiquitination in the cellular cytoplasm. In the presence of Wnt ligand and Wnt signaling, β-catenin is stabilized and travels to the cell nucleus where it can interact with transcription factors, such as T cell transcription factor (TCF) and lymphoid enhanced transcription factor (LEF), and activate gene transcription. Deregulation and activation of the Wnt/β-catenin pathway is most often caused by mutations in the β-catenin gene or the gene encoding adenomatous polyposis coli (APC), which negatively regulates β-catenin function, but can also be caused by a mutation in a gene encoding other components of the Wnt/β-catenin pathway, such as Axin, LEF, and ICAT.

DETAILED DESCRIPTION

This application provides new methods and compositions for treating cancer, including cancer that is not responsive to immunotherapy (e.g., blockade of immune checkpoint molecules). Typically, cancer that is not responsive to immunotherapy is characterized by a non-T cell inflamed phenotype (also known as cold or non-inflamed tumors), with little to no infiltrating CD8+ T cells in the tumor microenvironment. Reducing β-catenin expression can convert a cold or non-inflamed tumor into a hot or inflamed tumor and potentiate the effect of immunotherapy, even in tumors that do not have an activated Wnt/β-catenin pathway. In other words, by combining a β-catenin inhibitor with immunotherapy, it is possible to treat cold or non-inflamed tumors that normally do not respond to immunotherapy. Typically a β-catenin nucleic acid inhibitor molecule is used to reduce β-catenin expression. However, any β-catenin inhibitor or Wnt/β-catenin pathway inhibitor that reduces β-catenin expression can be used in the methods and compositions described herein, including, but not limited to small molecules, peptides, and antibodies that target β-catenin or a component of the Wnt/β-catenin pathway. This combination therapy approach has been shown to potently inhibit tumor growth in vivo across a broad variety of cancers, including cancers with and without an activated Wnt/β-catenin pathway.

Wnt/β-Catenin Pathway

As discussed above, the Wnt/β-catenin pathway is mediated through a combination of Wnt ligands, receptors, and co-receptors, which initiate a downstream signaling pathway that involves the β-catenin oncogene (see e.g., FIG. 1). In the absence of Wnt signaling, β-catenin is targeted for degradation via ubiquitination in the cellular cytoplasm. In the presence of Wnt ligand and Wnt signaling, β-catenin is stabilized and travels to the cell nucleus where it can interact with transcription factors, such as T cell transcription factor (TCF) and lymphoid enhanced transcription factor (LEF), and activate gene transcription.

β-catenin is a key mediator of Wnt signaling in cells. β-catenin serves several cellular functions at multiple cellular locations, including the plasma membrane, where β-catenin contributes to the stabilization of intercellular adhesive complexes, the cytoplasm where β-catenin levels are regulated, and the nucleus where β-catenin is involved in transcriptional regulation and chromatin interactions.

Mutations in β-catenin (encoded by the CTNNB1 gene in humans) have been specifically associated with colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers (Polakis P. Genes Dev. 14: 1837-51; Samowitz et al. Cancer Res. 59: 1442-4; Iwao et al. Cancer Res. 58: 1021-6; Mirabelli-Primdahl et al. Cancer Res. 59: 3346-51; Shitoh et al. J Clin Path. 52: 695-6; Tejpar et al. Oncogene 18: 6615-20; Kitaeva et al. Cancer Res. 57: 4478-81; Sparks et al. Cancer Res. 58: 1130-4; Miyaki et al. Cancer Res. 59: 4506-9; Park et al. Cancer Res. 59: 4257-60; Huang et al. Am J Pathol. 155: 1795-801; Nhieu et al. Am J Pathol. 155: 703-10; Legoix et al. Oncogene 18: 4044-6; Jeng et al. Cancer Lett. 152: 45-51; Koch et al. Cancer Res. 59: 269-73; Wei et al. Oncogene 19: 498-504; Koesters et al. Cancer Res. 59: 3880-2; Maiti et al. Cancer Res. 60: 6288-92; Zurawel et al. Cancer Res. 58: 896-9; Gamallo et al. Am J Pathol. 155: 527-36; Palacios and Gamallo Cancer Res. 58: 1344-7; Wright et al. Int J Cancer 82: 625-9; Gerdes et al. Digestion 60: 544-8; Chan et al. Nat Genet. 21: 410-3; Voeller et al. Cancer Res. 58: 2520-3; Garcia-Rostan et al. Cancer Res. 59: 1811-5; Fukuchi et al. Cancer Res. 58: 3526-8).

The β-catenin/Wnt pathway is consistently activated in over 80% of colorectal cancers. The role of β-catenin in the development of colorectal cancer has been shown to be regulated by the expression product of the APC (adenomatous polyposis of the colon) gene, a tumor suppressor. (Korinek et al., Science, 1997, 275:1784-1787; Morin et al., Science, 1997, 275:1787-1790). The APC protein normally binds β-catenin in conjunction with TCF/LEF forming a transcription factor complex. Morin et al. (Morin et al., Science, 1997, 275:1787-1790) report that APC protein down-regulates the transcriptional activation mediated by β-catenin and Tcf-4 in colon cancer. Their results indicated that the regulation of β-catenin is associated with APC's tumor suppressive effect and that this regulation can be circumvented by mutations in either APC or β-catenin.

The β-catenin/Wnt pathway is also consistently activated in over 50% of hepatocellular carcinoma (HCC) patients. Activated Wnt signaling and nuclear 13-catenin correlate with recurrence of disease and poor prognosis (Takigawa et al. 2008, Curr Drug Targets November; 9 (11):1013-24).

Mutations in the β-catenin gene include truncations that lead to deletion of part of the N-terminus of β-catenin or point mutations that affect the serine and threonine residues that are targeted by components of the cytoplasmic destruction complex, such as GSK3a/β or CKIα, that mediate the phosphorylation of β-catenin and target its degradation by the proteosome. These mutant β-catenin proteins are refractory to phosphorylation and thus escape proteasomal degradations. Consequently, β-catenin accumulates within affected cells. Stabilized and nuclear-localized β-catenin is a hallmark of nearly all cases of colon cancer. (Clevers, H., 2006, Cell 127:469-480). Morin et al. demonstrated that mutations of β-catenin that altered phosphorylation sites rendered the cells insensitive to APC-mediated down-regulation of β-catenin and that this disrupted mechanism was important to colorectal tumorigenesis. (Morin et al., 1997, Science 275:1787-1790).

In certain embodiments of the methods and compositions disclosed herein, the cancer has an activated Wnt/β-catenin signaling pathway. In other embodiments, the cancer does not have an activated Wnt/β-catenin signaling pathway.

Nucleic Acid Inhibitor Molecules

In certain embodiments, β-catenin expression is reduced using a nucleic acid inhibitor molecule. Various oligonucleotide structures have been used as nucleic acid inhibitor molecules, including single stranded and double stranded oligonucleotides.

In certain embodiments, the nucleic acid inhibitor molecule is a double-stranded RNAi inhibitor molecule comprising a sense (or passenger) strand and an antisense (or guide) strand. A variety of double stranded RNAi inhibitor molecule structures are known in the art. For example, early work on RNAi inhibitor molecules focused on double-stranded nucleic acid molecules with each strand having sizes of 19-25 nucleotides with at least one 3'-overhang of 1 to 5 nucleotides (see, e.g., U.S. Pat. No. 8,372,968). Subsequently, longer double-stranded RNAi inhibitor molecules that get processed in vivo by the Dicer enzyme to active RNAi inhibitor molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401, which are incorporated by reference for their disclosure of these double-stranded nucleic acid inhibitor molecules). Those structures include single-stranded extensions (on one or both sides of the molecule) and double-stranded extensions.

In some embodiments, the sense and antisense strands range from 15-66, 25-40, or 19-25 nucleotides. In some embodiments, the sense strand is less than 30 nucleotides, such as 19-24 nucleotides, such as 21 nucleotides. In some embodiments, the antisense strand is less than 30 nucleotides, such as 19-24 nucleotides, such as 21, 22, or 23 nucleotides. Typically, the duplex structure is between 15 and 50, such as between 15 and 30, such as between 18 and 26, more typically between 19 and 23, and in certain instances between 19 and 21 base pairs in length.

In some embodiments, the dsRNAi inhibitor molecule may further comprise one or more single-stranded nucleotide overhang(s). Typically, the dsRNAi inhibitor molecule has a single-stranded overhang of 1-10, 1-4, or 1-2 nucleotides. The single stranded overhang is typically located at the 3' end of the sense strand and/or the 3' end of the antisense strand. In certain embodiments, a single-stranded overhang of 1-10, 1-4, or 1-2 nucleotides is located at the 5' end of the antisense strand. In certain embodiments, a single-stranded overhang of 1-10, 1-4, or 1-2 nucleotides is located at the 5' end of the sense strand. In certain embodiments, the single-stranded overhang of 1-2 nucleotides is located at the 3' end of the antisense strand. In certain embodiments, the dsRNA inhibitor molecule has a blunt end, typically at the right hand side of the molecule, i.e., 3' end of the sense strand and the 5' end of the antisense strand.

In certain embodiments, the dsRNAi inhibitor molecule has a guide strand of 21 nucleotides in length and a passenger strand of 21 nucleotides in length, where there is a two nucleotide 3'-passenger strand overhang on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 19 base pair duplex region.

In certain embodiments, the dsRNAi inhibitor molecule has a guide strand of 23 nucleotides in length and a passenger strand of 21 nucleotides in length, where there is a blunt end on the right side of the molecule (3'-end of passenger strand/5'-end of guide strand) and a two nucleotide 3'-guide strand overhang on the left side of the molecule (5'-end of the passenger strand/3'-end of the guide strand). In such molecules, there is a 21 base pair duplex region.

In some embodiments, the dsRNAi inhibitor molecules include a stem and loop. Typically, a 3'-terminal region or 5'-terminal region of a passenger strand of a dsRNAi inhibitor molecule form a single stranded stem and loop structure.

In some embodiments, the dsRNAi inhibitor molecule contains a stem and tetraloop. In certain embodiments, the dsRNAi inhibitor molecule comprises a guide strand and a passenger strand, wherein the passenger strand contains a stem and tetraloop and ranges from 20-66 nucleotides in length. Typically, the guide and passenger strands are separate strands, each having a 5' and 3' end, that do not form a contiguous oligonucleotide (sometimes referred to as a "nicked" structure).

In certain of those embodiments, the guide strand is between 15 and 40 nucleotides in length. In certain embodiments, the extended part of the passenger strand that contains the stem and tetraloop is on 3'-end of the strand. In certain other embodiments, the extended part of the passenger strand that contains the stem and tetraloop is on 5'-end of the strand.

In certain embodiments, the passenger strand of a dsRNAi inhibitor molecule containing a stem and tetraloop is between 34 and 40 nucleotides in length and the guide strand of the dsRNAi inhibitor molecule contains between 20 and 24 nucleotides, wherein the passenger strand and guide strand form a duplex region of 18-24 base pairs.

In certain embodiments, the dsRNAi inhibitor molecule comprises (a) a passenger strand that contains a stem and tetraloop and is 36 nucleotides in length, wherein the first 20 nucleotides of the passenger strand from the 5'-end are complementary to the guide strand and the following 16 nucleotides of the passenger strand form the stem and tetraloop and (b) a guide strand that is 22 nucleotides in length and has a single-stranded overhang of two nucleotides at its 3' end, wherein the guide and passenger strands are separate strands that do not form a contiguous oligonucleotide.

In certain embodiments, the nucleic acid inhibitor molecule is a single-stranded nucleic acid inhibitor molecule. Single stranded nucleic acid inhibitor molecules are known in the art. For example, recent efforts have demonstrated activity of ssRNAi inhibitor molecules (see, e.g., Matsui et al., *Molecular Therapy*, 2016, 24(5):946-55). And, antisense molecules have been used for decades to reduce expression of specific target genes. Pelechano and Steinmetz, Nature Review Genetics, 2013, 14:880-93. A number of variations on the common themes of these structures have been developed for a range of targets. Single stranded nucleic acid inhibitor molecules include, for example, conventional antisense oligonucleotides, microRNA, ribozymes, aptamers, and ssRNAi inhibitor molecules, all of which are known in the art.

In certain embodiments, the nucleic acid inhibitor molecule is a ssRNAi inhibitor molecule having 14-50, 16-30, or 15-25 nucleotides. In other embodiments, the ssRNAi inhibitor molecule has 18-22 or 20-22 nucleotides. In certain embodiments, the ssRNAi inhibitor molecule has 20 nucleotides. In other embodiments, the ssRNAi inhibitor molecule has 22 nucleotides. In certain embodiments, the nucleic acid inhibitor molecule is a single-stranded oligonucleotide that inhibits exogenous RNAi inhibitor molecules or natural miRNAs.

In certain embodiments, the nucleic acid inhibitor molecule is a single-stranded antisense oligonucleotide having 8-80, 12-50, 12-30, or 12-22 nucleotides. In certain embodiments, the single-stranded antisense oligonucleotide has 16-20, 16-18, 18-22 or 18-20 nucleotides.

Modifications

Typically, multiple nucleotide subunits of the nucleic acid inhibitor molecule are modified to improve various characteristics of the molecule such as resistance to nucleases or lowered immunogenicity. See, e.g., Bramsen et al. (2009), *Nucleic Acids Res.*, 37, 2867-2881. Many nucleotide modifications have been used in the oligonucleotide field, particularly for nucleic acid inhibitor molecules. Such modifications can be made on any part of the nucleotide, including the sugar moiety, the phosphoester linkage, and the nucleobase. In certain embodiments of the nucleic acid inhibitor molecule, from one to every nucleotide is modified at the 2'-carbon of the sugar moiety, using, for example, 2'-carbon modifications known in the art and described herein. Typical examples of 2'-carbon modifications include, but are not limited to, 2'-F, 2'-O-methyl ("2'-OMe" or "2'-OCH$_3$"), 2'-O-methoxyethyl ("2'-MOE" or "2'-OCH$_2$CH$_2$OCH$_3$"). Modifications can also occur at other parts of the sugar moiety of the nucleotide, such as the 5'-carbon, as described herein.

In certain embodiments, the ring structure of the sugar moiety is modified, including, but not limited to, Locked Nucleic Acids ("LNA") (see, e.g., Koshkin et al. (1998), Tetrahedron, 54, 3607-3630)), bridged nucleic acids ("BNA") (see, e.g., U.S. Pat. No. 7,427,672 and Mitsuoka et al. (2009), *Nucleic Acids Res.*, 37(4):1225-38); and Unlocked Nucleic Acids ("UNA") (see, e.g., Snead et al. (2013), *Molecular Therapy—Nucleic Acids*, 2, e103(doi: 10.1038/mtna.2013.36)).

Modified nucleobases include nucleobases other than adenine, guanine, cytosine, thymine and uracil at the 1'-position, as known in the art and as described herein. A typical example of a modified nucleobase is 5'-methylcytosine.

The natural occurring internucleotide linkage of RNA and DNA is a 3' to 5' phosphodiester linkage. Modified phosphoester linkages include non-naturally occurring internucleotide linking groups, including internucleotide linkages that contain a phosphorous atom and internucleotide linkages that do not contain a phosphorous atom, as known in the art and as described herein. Typically, the nucleic acid inhibitor molecule contains one or more phosphorous-containing internucleotide linking groups, as described herein.

In other embodiments, one or more of the internucleotide linking groups of the nucleic acid inhibitor molecule is a non-phosphorus containing linkage, as described herein. In certain embodiments, the nucleic acid inhibitor molecule contains one or more phosphorous-containing internucleotide linking groups and one or more non-phosphorous containing internucleotide linking groups.

The 5'-end of the nucleic acid inhibitor molecule can include a natural substituent, such as a hydroxyl or a phosphate group. In certain embodiments, a hydroxyl group is attached to the 5'-terminal end of the nucleic acid inhibitor molecule. In certain embodiments, a phosphate group is attached to the 5'-terminal end of the nucleic acid inhibitor molecule. Typically, the phosphate is added to a monomer prior to oligonucleotide synthesis. In other embodiments, 5'-phosphorylation is accomplished naturally after a nucleic acid inhibitor molecule is introduced into the cytosol, for example, by a cytosolic Clp1 kinase. In some embodiments, the 5'-terminal phosphate is a phosphate group, such as 5'-monophosphate [$(HO)_2(O)P$—O-5'], 5'-diphosphate [$(HO)_2(O)P$—O—$P(HO)(O)$—O-5'] or a 5'-triphosphate [$(HO)_2(O)P$—O—$(HO)(O)P$—O—$P(HO)(O)$-0-5'].

The 5'-end of the nucleic acid inhibitor molecule can also be modified. For example, in some embodiments, the 5'-end of the nucleic acid inhibitor molecule is attached to a phosphoramidate [$(HO)_2(O)P$—NH-5', $(HO)(NH_2)(O)P$—O-5']. In certain embodiments, the 5'-terminal end of the nucleic acid inhibitor molecule is attached to a phosphate mimic. Suitable phosphate mimics include 5'-phosphonates, such as 5'-methylenephosphonate (5'-MP), 5'-(E)-vinylphosphonate (5'-VP). Lima et al., Cell, 2012, 150-883-94; WO2014/130607. Other suitable phosphate mimics include 4-phosphate analogs that are bound to the 4'-carbon of the sugar moiety (e.g., a ribose or deoxyribose or analog thereof) of the 5'-terminal nucleotide of an oligonucleotide as described in International Publication No. WO 2018/045317, which is hereby incorporated by reference in its entirety. For example, in some embodiments, the 5'-end of the nucleic acid inhibitor molecule is attached to an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the nucleic acid inhibitor molecule include one or more deoxyribonucleotides. Typically, the nucleic acid inhibitor molecules contain fewer than 5 deoxyribonucleotides. In certain embodiments, the nucleic acid inhibitor molecules include one or more ribonucleotides. In certain embodiments, all of the nucleotides of the nucleic acid inhibitor molecule are ribonucleotides.

In certain embodiments one or two nucleotides of a nucleic acid inhibitor molecule are reversibly modified with a glutathione-sensitive moiety. Typically, the glutathione-sensitive moiety is located at the 2'-carbon of the sugar moiety and comprises a sulfonyl group. In certain embodiment, the glutathione-sensitive moiety is compatible with phosphoramidite oligonucleotide synthesis methods, as described, for example, in International Publication No. WO 2018/045317, which is hereby incorporated by reference in its entirety. In certain embodiments, more than two nucleotides of a nucleic acid inhibitor molecule are reversibly modified with a glutathione-sensitive moiety. In certain embodiments, most of the nucleotides are reversibly modified with a glutathione-sensitive moiety. In certain embodiments, all or substantially all the nucleotides of a nucleic acid inhibitor molecule are reversibly modified with a glutathione-sensitive moiety.

The at least one glutathione-sensitive moiety is typically located at the 5'- or 3'-terminal nucleotide of a single-stranded nucleic acid inhibitor molecule or the 5'- or 3'-terminal nucleotide of the passenger strand or the guide strand of a double-stranded nucleic acid inhibitor molecule. However, the at least one glutathione-sensitive moiety may be located at any nucleotide of interest in the nucleic acid inhibitor molecule.

In certain embodiments, a nucleic acid inhibitor molecule is fully modified, wherein every nucleotide of the fully modified nucleic acid inhibitor molecule is modified. In certain embodiments, the fully modified nucleic acid inhibitor molecule does not contain a reversible modification. In some embodiments, at least one, such as at least two, three, four, five, six, seven, eight, nine, 10, 11, 12, 13, 14, 15, 16, 17, 18, 19, or 20 nucleotides of a single stranded nucleic acid inhibitor molecule or the guide strand or passenger strand of a double stranded nucleic acid inhibitor molecule are modified.

In certain embodiments, the fully modified nucleic acid inhibitor molecule is modified with one or more reversible, glutathione-sensitive moieties. In certain embodiments, substantially all of the nucleotides of a nucleic acid inhibitor molecule are modified. In certain embodiments, more than half of the nucleotides of a nucleic acid inhibitor molecule are modified with a chemical modification other than a reversible modification. In certain embodiments, less than half of the nucleotides of a nucleic acid inhibitor molecule are modified with a chemical modification other than a reversible modification. Modifications can occur in groups on the nucleic acid inhibitor molecule or different modified nucleotides can be interspersed.

In certain embodiments of the nucleic acid inhibitor molecule, from one to every nucleotide is modified at the 2'-carbon. In certain embodiments, the nucleic acid inhibitor molecule (or the sense strand and/or antisense strand thereof) is partially or fully modified with 2'-F, 2'-O-Me, and/or 2'-MOE. In certain embodiments of the nucleic acid inhibitor molecule, from one to every phosphorous atom is modified and from one to every nucleotide is modified at the 2'-carbon.

β-Catenin Nucleic Acid Inhibitor

As disclosed herein, a β-catenin nucleic acid inhibitor molecule can be combined with immunotherapy for treating certain diseases or disorders, such as non-Wnt activated cancer. We have shown that these combinations can produce synergetic effects as compared to the administration of each agent individually. See e.g., Example 4.

β-catenin nucleic acid inhibitor molecules are known, as disclosed, for example, in U.S. Provisional Application No. 62/573,999; U.S. Published Application Nos. 2015/0291954 and 2015/0291956 and U.S. Pat. No. 6,066,500; 8,198,427; 8,835,623; or 9,243,244, all of which are incorporated by reference for their disclosure of these β-catenin nucleic acid inhibitor molecules. In certain embodiments, the β-catenin nucleic acid inhibitor molecule is a molecule disclosed in U.S. Pat. No. 9,243,244. In certain embodiments, the β-catenin nucleic acid inhibitor molecule is a molecule disclosed in U.S. Provisional Application No. 62/573,999.

In certain embodiments, the β-catenin nucleic acid inhibitor molecules of the invention are dsRNAi inhibitor molecules where the double-stranded region of the molecule is between 15-40 nucleotides in length. In certain of those embodiments, the double-stranded region is between 19-30, 19-23, or 19-21 nucleotides in length. In certain of those embodiments, the double-stranded region is 19, 20, 21, 22, 23, 24, 25, or 26 nucleotides in length.

In certain embodiments, the β-catenin nucleic acid inhibitor molecules of the invention are dsRNAi inhibitor molecules where the sense strand is between 18 and 66 nucleotides in length. In certain embodiments, the sense strand is between 18 and 25 nucleotides in length. In certain embodiments, the sense strand is 18, 19, 20, 21, 22, 23, or 24 nucleotides in length. In certain of those embodiments, the sense strand is between 25 and 45 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In certain embodiments, the β-catenin nucleic acid inhibitor molecules are dsRNAi inhibitor molecules where the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In certain embodiments, the β-catenin nucleic acid inhibitor molecule is a dsRNAi inhibitor molecule comprising a sense and an antisense strand and a duplex region of between 18-34 base pairs, wherein the sense strand is 25-34 nucleotides in length and the antisense strand is 26-38 nucleotides in length and comprises 1-5 single-stranded nucleotides at its 3' terminus. In certain embodiments, the sense strand is 26 nucleotides, the antisense strand is 38 nucleotides and has a single-stranded overhang of 2 nucleotides at its 3' terminus and a single-stranded overhang of 10 nucleotides at its 5' terminus, and the sense strand and antisense strand form a duplex region of 26 base pairs. In certain embodiments, the sense strand is 25 nucleotides, the antisense strand is 27 nucleotides and has a single-stranded overhang of 2 nucleotides at its 3' terminus, and the sense strand and antisense strand form a duplex region of 25 base pairs.

In certain embodiments, the β-catenin nucleic acid inhibitor molecule is a dsRNAi inhibitor molecule comprising a sense and an antisense strand and a duplex region of between 19-21 base pairs, wherein the sense strand is 19-21 nucleotides in length and the antisense strand is 21-23 nucleotides in length and comprises a single-stranded overhang of 1-2 nucleotides at its 3' terminus. In certain embodiments, the sense strand is 21 nucleotides and has a single-stranded overhang of 2 nucleotides at its 3' end, the antisense strand is 21 nucleotides and has a single-stranded overhang of 2 nucleotides at its 3' end, and sense strand and antisense strand form a duplex region of 19 base pairs. In certain embodiments, the sense strand is 21 nucleotides, the antisense strand is 23 nucleotides and has a single-stranded overhang of 2 nucleotides at its 3' end, the sense strand and antisense strand form a duplex region of 21 base pairs, and the 3' end of the sense strand and the 5' end of the antisense strand form a blunt end.

In some embodiments, the β-catenin nucleic acid inhibitor molecule is a dsRNAi inhibitor molecule comprising a stem and tetraloop. In certain embodiments, the sense strand of the dsRNAi inhibitor molecule contains the stem and tetraloop and is between 34-40 or 34-36 nucleotides in length and the antisense strand of the dsRNAi inhibitor molecule contains between 20-24 nucleotides, wherein the sense strand and antisense strand form a duplex region of 18-24 base pairs.

In certain embodiments, the dsRNAi inhibitor molecule comprises (a) a sense strand that contains a stem and tetraloop and is 36 nucleotides in length, wherein the first 20 nucleotides of the sense strand from the 5'-end are complementary to the antisense strand and the following 16 nucleotides of the sense strand form the stem and tetraloop and (b) an antisense strand that is 22 nucleotides in length and has a single-stranded overhang of two nucleotides at its 3' end, wherein the antisense and sense strands are separate strands that do not form a contiguous oligonucleotide.

In certain embodiments, the β-catenin nucleic acid inhibitor molecule is a conventional antisense oligonucleotide that has a sequence in the 5' to 3' direction that comprises the reverse complement of a segment of a target nucleic acid (e.g., β-catenin). In certain embodiments, the antisense oligonucleotide comprises 12-30, 12-25, 12-22, 14-20, 16-20, or 18-22 nucleotides. In certain embodiments, the antisense oligonucleotide comprises 16-18 nucleotides. In certain embodiments, the antisense oligonucleotide comprises 18-20 nucleotides. In other embodiment, the antisense oligonucleotide has 8-80 or 12-50 nucleotides. In certain embodiments, the antisense oligonucleotide or a portion thereof is fully complementary to a target nucleic acid (e.g., β-catenin) or a specific portion thereof. In certain embodiments, the antisense oligonucleotide or a portion thereof is complementary to at least 12, 13, 14, 15, 16, 17, 18, 19, 20, or more contiguous nucleotides of the target nucleic acid (e.g., β-catenin). In certain embodiments, the antisense oligonucleotide contains no more than 5, 4, 3, 2, or 1 non-complementary nucleotides relative to the target nucleic acid (e.g., β-catenin) or portion thereof. It is possible to decrease the length of the antisense oligonucleotide and/or introduce mismatch bases without eliminating activity.

In certain embodiments, the β-catenin nucleic acid inhibitor molecules of the invention are ssRNAi inhibitor molecules.

In certain embodiments, the antisense strand of the β-catenin nucleic acid inhibitor molecule comprises the sequence of SEQ ID NO: 2. In certain embodiments, the antisense strand of the β-catenin nucleic acid inhibitor molecule consists of the sequence of SEQ ID NO: 2. In certain embodiments, the β-catenin nucleic acid inhibitor molecule is a dsRNAi inhibitor molecule and the sense strand comprises the sequence of SEQ ID NO: 1. In certain embodiments, the β-catenin nucleic acid inhibitor molecule is a dsRNAi inhibitor molecule and the sense strand consists of the sequence of SEQ ID NO: 1. In certain embodiments, the β-catenin nucleic acid inhibitor molecule is a dsRNAi inhibitor molecule and the sense strand comprises the sequence of SEQ ID NO: 1 and the antisense strand comprises the sequence of SEQ ID NO: 2. In certain embodiments, the β-catenin nucleic acid inhibitor molecule is a dsRNAi inhibitor molecule where the sense strand consists of the sequence of SEQ ID NO: 1 and the antisense strand consists of the sequence of SEQ ID NO: 2.

The level or activity of a β-catenin RNA can be determined by a suitable method now known in the art or that is later developed. It can be appreciated that the method used to measure a target RNA and/or the "expression" of a target gene can depend upon the nature of the target gene and its encoded RNA. For example, where the target β-catenin RNA sequence encodes a protein, the term "expression" can refer to a protein or the β-catenin RNA/transcript derived from the β-catenin gene (either genomic or of exogenous origin). In such instances the expression of the target β-catenin RNA can be determined by measuring the amount of β-catenin RNA/transcript directly or by measuring the amount of β-catenin protein. Protein can be measured in protein assays such as by staining or immunoblotting or, if the protein catalyzes a reaction that can be measured, by measuring reaction rates. All such methods are known in the art and can be used. Where target β-catenin RNA levels are to be measured, art-recognized methods for detecting RNA levels can be used (e.g., RT-PCR, Northern Blotting, etc.). In targeting β-catenin RNAs, measurement of the efficacy of the nucleic acid inhibitor molecule in reducing levels of β-catenin RNA or protein in a subject, tissue, in cells, either in vitro or in vivo, or in cell extracts can also be used to determine the extent of reduction of β-catenin-associated phenotypes (e.g., disease or disorders, e.g., cancer or tumor formation, growth, metastasis, spread, etc.), as disclosed, for example, in International Application No. PCT/US2017/022510, which is published as WO/2017/160983. The above measurements can be made on cells, cell extracts, tissues, tissue extracts or other suitable source material.

Immunotherapy

The methods and compositions disclosed herein relate to combination therapy with a β-catenin inhibitor and immunotherapy (or an immunotherapeutic agent). Administering the β-catenin inhibitor renders tumors that are not responsive to immunotherapy susceptible to immunotherapy.

Immunotherapy refers to methods of enhancing an immune response. Typically, in the methods disclosed herein an anti-tumor immune response is enhanced. In certain embodiments, immunotherapy refers to methods of enhancing a T cell response against a tumor or cancer.

In certain embodiments, the immunotherapy or immunotherapeutic agent targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory immune checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these inhibitory immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody and preferably is a monoclonal antibody. In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In certain embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab (Opdivo®). In certain embodiments, the anti-CTLA4 antibody is ipilimumab (Yervoy®). In certain embodiments, the anti-PD-L1 antibody is one or more of atezolizumab (Tecentriq®), avelumab (Bavencio®), or durvalumab (Imfinzi®).

In certain embodiments, the immunotherapy or immunotherapeutic agent is an antagonist (e.g. antibody) against CD80, CD86, LAG3, KIR, TIM3, GAL9, or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In certain embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

Pharmaceutical Compositions

The present disclosure provides pharmaceutical compositions comprising a therapeutically effective amount of a β-catenin nucleic acid inhibitor molecule and a pharmaceutically acceptable excipient. Typically, the β-catenin nucleic acid inhibitor molecule is not included in the same pharmaceutical composition as the IDO inhibitor or the immunotherapeutic agent. However, in certain embodiments, the pharmaceutical composition comprising the β-catenin nucleic acid inhibitor molecule and the pharmaceutically acceptable excipient further comprises a therapeutically effective amount of an immunotherapeutic agent, such as an antagonist of an inhibitory immune checkpoint molecule (e.g., one or more of an anti-CTLA-4, anti-PD-1, or anti-PD-L1 antibody) or an agonist of a co-stimulatory checkpoint molecule.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous excipient prior to administration. The pH of the preparations typically will be between 3 and 11, more preferably between 5 and 9 or between 6 and 8, and most preferably between 7 and 8, such as 7 to 7.5.

The pharmaceutical compositions of the present disclosure are applied for therapeutic use. Thus, one aspect of the disclosure provides a pharmaceutical composition, which may be used to treat a subject including, but not limited to, a human suffering from a disease or condition by administering to said subject a therapeutically effective amount of a pharmaceutical composition of the present disclosure. Typically, the disease or condition is cancer, as described herein.

In certain embodiments, the present disclosure features the use of a therapeutically effective amount of a pharmaceutical composition as described herein for the manufacture of a medicament for treatment of a subject in need thereof. Typically, the subject has cancer, as described herein.

Pharmaceutically-Acceptable Excipients

Typically, the pharmaceutically-acceptable excipients useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

Dosage Forms

The pharmaceutical compositions may be formulated with conventional excipients for any intended route of administration.

Typically, the pharmaceutical compositions of the present disclosure that contain a β-catenin nucleic acid inhibitor molecule are formulated in liquid form for parenteral administration, for example, by subcutaneous, intramuscular, intravenous or epidural injection. Typically, the pharmaceutical compositions that contain an immunotherapeutic agent, such as an antagonist of an inhibitory immune checkpoint molecule (e.g., one or more of an anti-CTLA-4, anti-PD-1, or anti-PD-L1 antibody) or an agonist of a co-stimulatory checkpoint molecule are formulated in liquid form for parenteral administration, for example, by subcutaneous, intramuscular, intravenous or epidural injection.

Dosage forms suitable for parenteral administration typically include one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by the use of surfactants. Liquid formulations can be lyophilized and stored for later use upon reconstitution with a sterile injectable solution.

The pharmaceutical compositions may also be formulated for other routes of administration including topical or transdermal administration, rectal or vaginal administration, ocular administration, nasal administration, buccal administration, or sublingual administration.

Delivery Agents

The β-catenin nucleic acid inhibitor molecule may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the β-catenin nucleic acid inhibitor molecule is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may desirable to remove solvent (e.g., ethanol) used to form the nanoparticle and/or exchange buffer, which can be accomplished by, for example, dialysis or tangential flow filtration. Methods of making lipid nanoparticles containing nucleic acid interference molecules are known in the art, as disclosed, for example in U.S. Published Patent Application Nos. 2015/0374842 and 2014/0107178.

In certain embodiments, the LNP comprises a core lipid component comprising a cationic liposome and a pegylated lipid. The LNP can further comprise one or more envelope lipids, such as a cationic lipid, a structural or neutral lipid, a sterol, a pegylated lipid, or mixtures thereof.

Figure 11:
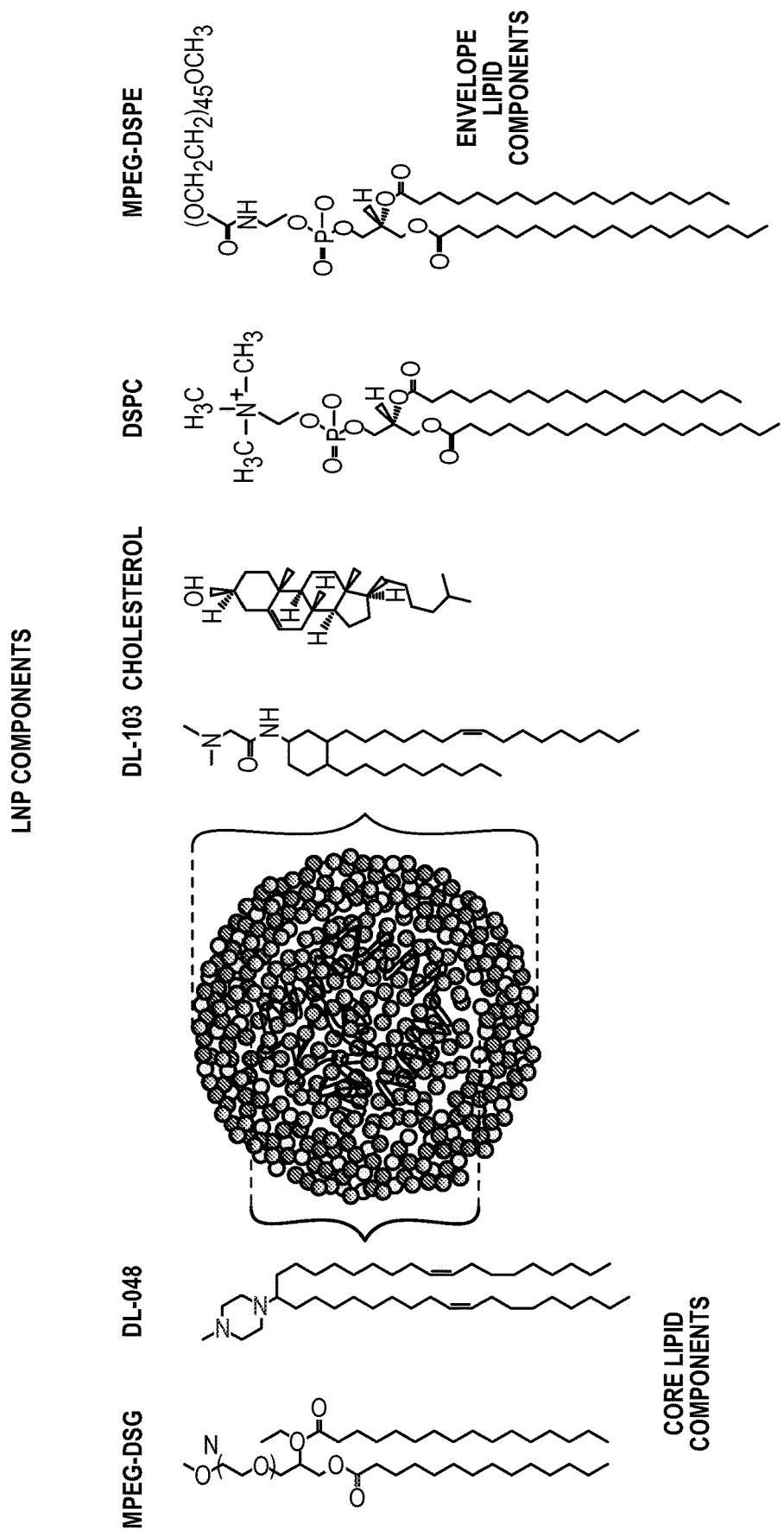
FIG. 11 shows one non-limiting embodiment of a lipid nanoparticle (LNP) that can be used to formulate the β-catenin nucleic acid inhibitor molecule. The LNP includes the following core lipids: DL-048 (cationic lipid) and DSG-MPEG (pegylated lipid), and the following envelope lipids: DL-103 (cationic lipid), DSPC, cholesterol, and DSPE-MPEG (pegylated lipid).

Cationic lipids for use in LNPs are known in the art, as discussed for example in U.S. Published Patent Application Nos. 2015/0374842 and 2014/0107178. Typically, the cationic lipid is a lipid having a net positive charge at physiological pH. In certain embodiments, the cationic liposome is DODMA, DOTMA, DL-048, or DL-103. In certain embodiments the structural lipid is DSPC, DPPC or DOPC. In certain embodiments, the sterol is cholesterol. In certain embodiments, the pegylated lipid is DMPE-PEG, DSPE-PEG, DSG-PEG, DMPE-PEG2K, DSPE-PEG2K, DSG-PEG2K, or DSG-MPEG. In one embodiment, the cationic lipid is DL-048, the pegylated lipid is DSG-MPEG and the one or more envelope lipids are DL-103, DSPC, cholesterol, and DSPE-MPEG. See e.g., FIG. 11, showing one non-limiting embodiment of a LNP that can used to formulate the β-catenin nucleic acid inhibitor molecule.

In certain embodiments, the β-catenin nucleic acid inhibitor molecule is covalently conjugated to a ligand that directs delivery of the oligonucleotide to a tissue of interest. Many such ligands have been explored. See, e.g., Winkler, Ther. Deliv. 4(7): 791-809 (2013). For example, the β-catenin nucleic acid inhibitor molecule can be conjugated to one or more sugar ligand moieties (e.g., N-acetylgalactosamine (GalNAc)) to direct uptake of the oligonucleotide into the liver. See, e.g., U.S. Pat. Nos. 5,994,517; 5,574,142; WO 2016/100401. Typically, the β-catenin nucleic acid inhibitor molecule is conjugated to three or four sugar ligand moieties (e.g., GalNAc). Other ligands that can be used include, but are not limited to, mannose-6-phosphate, cholesterol, folate, transferrin, and galactose (for other specific exemplary ligands see, e.g., WO 2012/089352). Typically, when an oligonucleotide is conjugated to a ligand, the oligonucleotide is administered as a naked oligonucleotide, wherein the oligonucleotide is not also formulated in an LNP or other protective coating. In certain embodiments, each nucleotide within the naked oligonucleotide is modified at the 2'-position of the sugar moiety, typically with 2'-F, 2'-OMe, and/or 2'-MOE.

Methods of Administration/Treatment

The pharmaceutical compositions described herein that contain a β-catenin nucleic acid inhibitor molecule or an immunotherapeutic agent are typically administered parenterally. Pharmaceutical compositions containing the β-catenin nucleic acid inhibitor molecule are typically administered intravenously or subcutaneously. Pharmaceutical compositions containing the immunotherapeutic agent are typically administered intravenously. However, the pharmaceutical compositions disclosed herein may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the pharmaceutical compositions disclosed herein may be useful for the treatment or prevention of symptoms related to a Wnt activated disease or disorder, such as cancer. In other embodiments, the pharmaceutical compositions disclosed herein may be useful for the treatment or prevention of symptoms related to a non-Wnt activated disease or disorder, such as cancer.

One embodiment is directed to a method of treating cancer, comprising administering to a subject a pharmaceutical composition comprising a therapeutically effective amount of a β-catenin nucleic acid inhibitor molecule and a therapeutically effective amount of an immunotherapeutic agent. In some embodiments, the β-catenin nucleic acid inhibitor molecule is an RNAi inhibitor molecule, including a ssRNAi inhibitor molecule or a dsRNAi inhibitor molecule. In some embodiments, the immunotherapeutic agent is as an antagonist of an inhibitory immune checkpoint molecule or an agonist of a co-stimulatory checkpoint molecule. In certain embodiments, the antagonist of an inhibitory immune checkpoint molecule is an anti-CTLA-4, anti-PD-1, anti-PD-L1 antibody, or a combination of thereof.

Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. In certain embodiments, the present disclosure features methods of treating liver cancer, liver carcinoma, hepatoma, hepatocellular carcinoma, cholangiocarcinoma and hepatoblastoma. In certain embodiments of the treatment methods, the cancer is colorectal cancer, hepatocellular carcinoma, or melanoma. In certain embodiments of the treatment methods, the cancer is a melanoma, a neuroblastoma, or a renal cancer.

In certain embodiments of the treatment methods, prior to the administration of the β-catenin nucleic acid inhibitor molecule, the cancer is not responsive to immunotherapy, such as an antagonist of an inhibitory immune checkpoint molecule (e.g., one or more of an anti-CTLA-4, anti-PD-1, or anti-PD-L1 antibody) or an agonist of a co-stimulatory checkpoint molecule, such as an anti-CD28 antibody.

In some embodiments, the cancer is associated with an activated Wnt/β-catenin pathway. In other embodiments, the cancer is a non-Wnt activated cancer. In certain embodiments, the subject has been identified as having a non-Wnt activated cancer before administering the β-catenin nucleic acid inhibitor molecule. The subject may be identified as having a non-Wnt activated cancer using any method available to the skilled artisan. Typically, however, a sample from the subject is analyzed to determine if the subject has a non-Wnt activated cancer. In certain embodiments, the sample comprises tissue, cells, blood, or urine. In certain embodiments, the sample is analyzed for one or more biomarkers associated with an activated Wnt/β-catenin pathway, an inactive Wnt/β-catenin pathway and/or a non-T cell inflamed phenotype. Any appropriate biomarker can be analyzed, including, but not limited to nucleic acids (e.g., mRNA), proteins, and peptides using any suitable assay or technique. In certain embodiments, the biomarker is a gene mutation that is associated with an activated Wnt/β-catenin pathway, such as a mutation in a gene encoding β-catenin or APC or one or more other components involved in the Wnt/β-catenin pathway, such as, Axin, LEF, and ICAT.

In certain embodiments, the non-Wnt activated cancer is resistant to immunotherapy, but the resistance to immunotherapy can be reversed by administering the immunotherapy in combination with the β-catenin nucleic acid inhibitor molecule.

In some embodiments, the present disclosure provides a method of potentiating an in vivo immune response against a cancer, comprising administering to a subject having cancer a β-catenin nucleic acid inhibitor molecule in an amount sufficient to potentiate the therapeutic effect of immunotherapy against the cancer or otherwise render the cancer susceptible to the immunotherapy. Typically, prior to administering the β-catenin nucleic acid inhibitor molecule, the cancer is associated with a non-T cell inflamed phenotype that is resistant to immunotherapy and administering the β-catenin nucleic acid inhibitor molecule converts the non-T cell inflamed phenotype into a T cell-inflamed phenotype, such that the cancer becomes responsive to immunotherapy. In certain embodiments, the subject experiences tumor regression following treatment with the β-catenin nucleic acid inhibitor molecule and the immunotherapy. In certain embodiments, the cancer that is resistant to immunotherapy is a Wnt activated cancer. In other embodiments, the cancer that is resistant to immunotherapy is a non-Wnt activated cancer. Typically, the subject begins taking the immunotherapeutic agent after the initiation of administration of the β-catenin nucleic acid inhibitor molecule. In other embodiments, the subject may already be taking the immunotherapeutic agent at the initiation of the administration of the β-catenin nucleic acid inhibitor molecule. In yet other embodiments, the subject may begin administration of both the immunotherapeutic agent and the β-catenin nucleic acid inhibitor molecule at about the same time.

Dosing and Schedule

Typically, the β-catenin nucleic acid inhibitor molecule is administered separately from, and on a different schedule than, the immunotherapeutic agent. For example, when used as a single agent, ipilimumab (anti-CTLA-4 antibody) is administered intravenously over 90 minutes at a recommended dose of 3 mg/kg every 3 weeks for a total of 4 doses. Similarly, when used as a single agent, nivolumab (anti-PD-1 antibody), is administered intravenously at a recommended dose of 240 mg (or 3 mg/kg) over 60 minutes every 2 weeks. When nivolumab is administered in combination with ipilimumab, the recommended dose of nivolumab is 1 mg/kg administered intravenously over 60 minutes, followed by ipilimumab on the same day at a recommended dose of 3 mg/kg every 3 weeks for a total of 4 doses, and then nivolumab at a recommended dose of 240 mg every 2 weeks. When pembrolizumab is used as a single agent, it is typically administered intravenously over 30 minutes at a recommended dosage of 200 mg every 3 weeks until disease progression, unacceptable toxicity, or up to 24 months without disease progression.

In certain embodiments, the β-catenin nucleic acid inhibitor molecule is administered before the immunotherapeutic agent. In certain embodiments, the β-catenin nucleic acid inhibitor molecule is administered after the immunotherapeutic agent. In certain embodiments, the patient has been previously treated with the therapeutic agent before beginning treatment with the β-catenin nucleic acid inhibitor molecule. The therapeutically effective amount of the β-catenin nucleic acid inhibitor molecule or immunotherapeutic agent may depend on the route of administration and the physical characteristics of the patient, such as the size and weight of the subject, the extent of the disease progression or penetration, the age, health, and sex of the subject and can be adjusted as necessary depending on these and other factors.

Typically, the β-catenin nucleic acid inhibitor molecule is administered parenterally (such as via intravenous, intramuscular, or subcutaneous administration). In certain embodiments, the β-catenin nucleic acid inhibitor molecule is administered at a dosage of 20 micrograms to 10 milligrams per kilogram body weight of the recipient per day, 100 micrograms to 5 milligrams per kilogram, 0.25 milligrams to 2.0 milligrams per kilogram, or 0.5 to 2.0 milligrams per kilogram. Typically, the β-catenin nucleic acid inhibitor molecule is administered at a dosage of about 0.25 to 2.0 milligrams per kilogram body weight of the recipient per day.

The β-catenin nucleic acid inhibitor molecule may be administered every day or intermittently. For example, intermittent administration of the β-catenin nucleic acid inhibitor molecule or immunotherapeutic agent may be administration one to six days per week, one to six days per month, once weekly, once every other week, once monthly, once every other month, once or twice per year, or divided into multiple yearly, monthly, weekly, or daily doses. Typically, the β-catenin nucleic acid inhibitor molecule is administered every week or every two weeks. In some embodiments, intermittent dosing may mean administration in cycles with the initial β-catenin nucleic acid inhibitor molecule or immunotherapeutic agent administration followed by a rest period with no administration for up to one week, up to one month, up to two months, up to three months or up to six months or more) or it may mean administration on alternate days, weeks, months or years.

The β-catenin nucleic acid inhibitor molecule is typically administered separately from, and on a different schedule than, the immunotherapeutic agent.

The therapeutically effective amount of the β-catenin nucleic acid inhibitor molecule or immunotherapeutic agent may depend on the route of administration and the physical characteristics of the patient, such as the size and weight of the subject, the extent of the disease progression or penetration, the age, health, and sex of the subject and can be adjusted as necessary depending on these and other factors.

EXAMPLES

Example 1: BCAT1 Construct

Figure 9A:
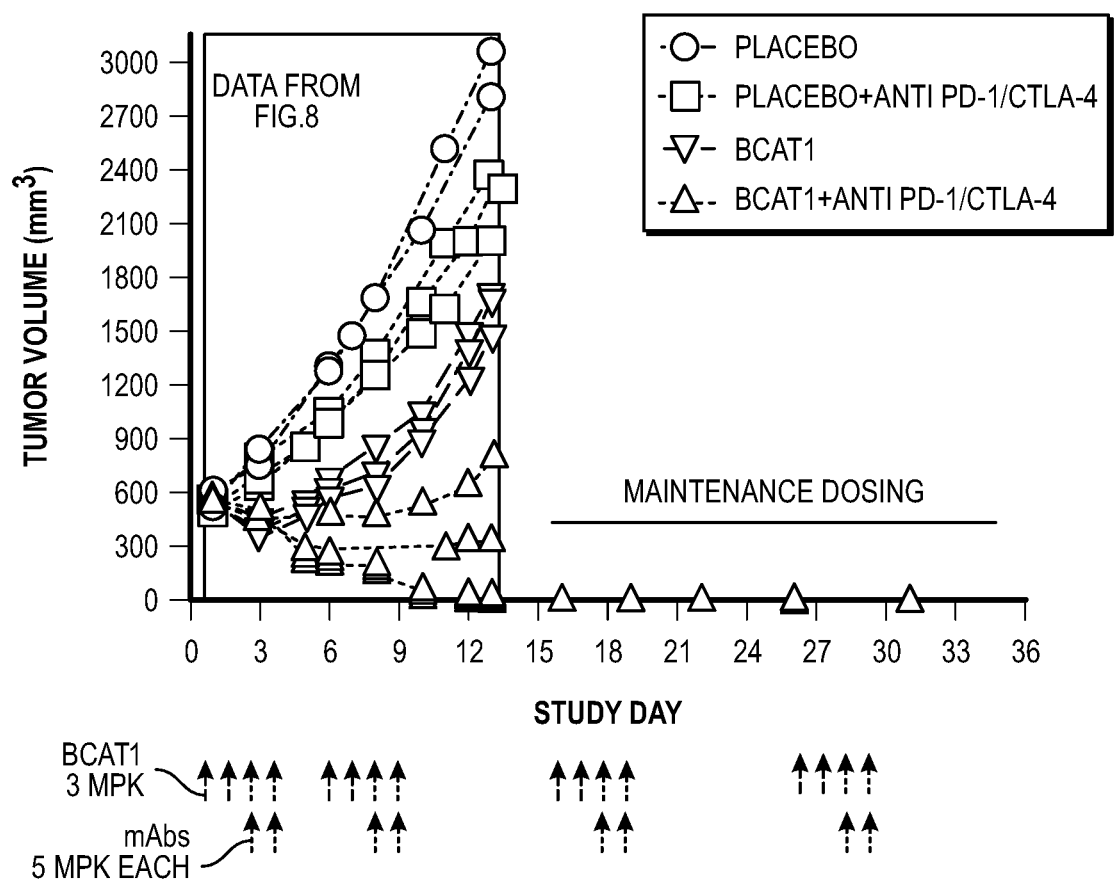
FIG. 9A shows the combination therapy treatment schedule for mice with spontaneous MMTV-Wnt1 tumors that completed the Cycle 1 treatment schedule and received follow on maintenance doses of BCAT1 and anti-PD-1/CTLA-4 antibodies.
Figure 9B:
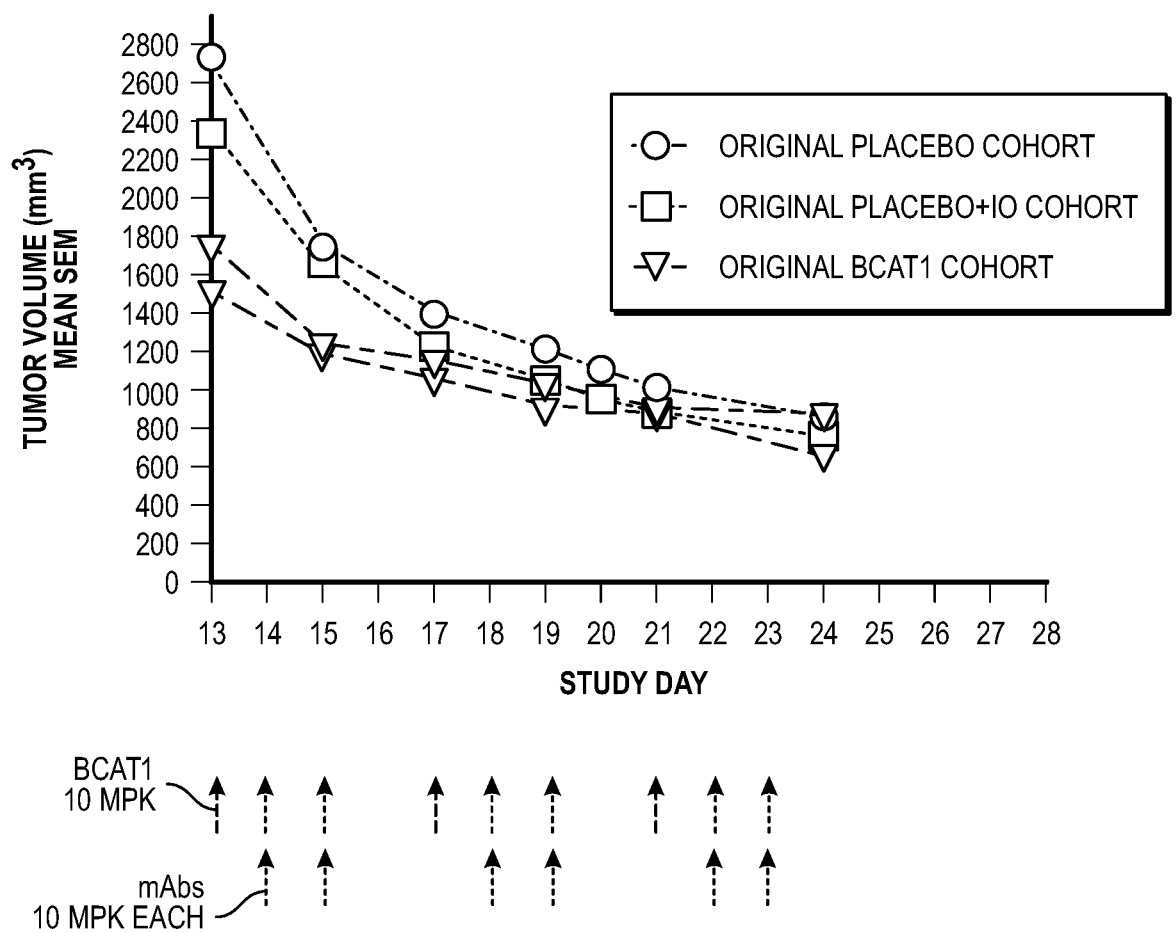
FIG. 9B shows that four mice with large tumors following completion of the Cycle 1 treatment exhibited potent inhibition of tumor growth when treated with BCAT1 and anti-PD-1/CTLA-4 antibodies according to the Cycle 2 treatment schedule.
Figures 9C, 10:
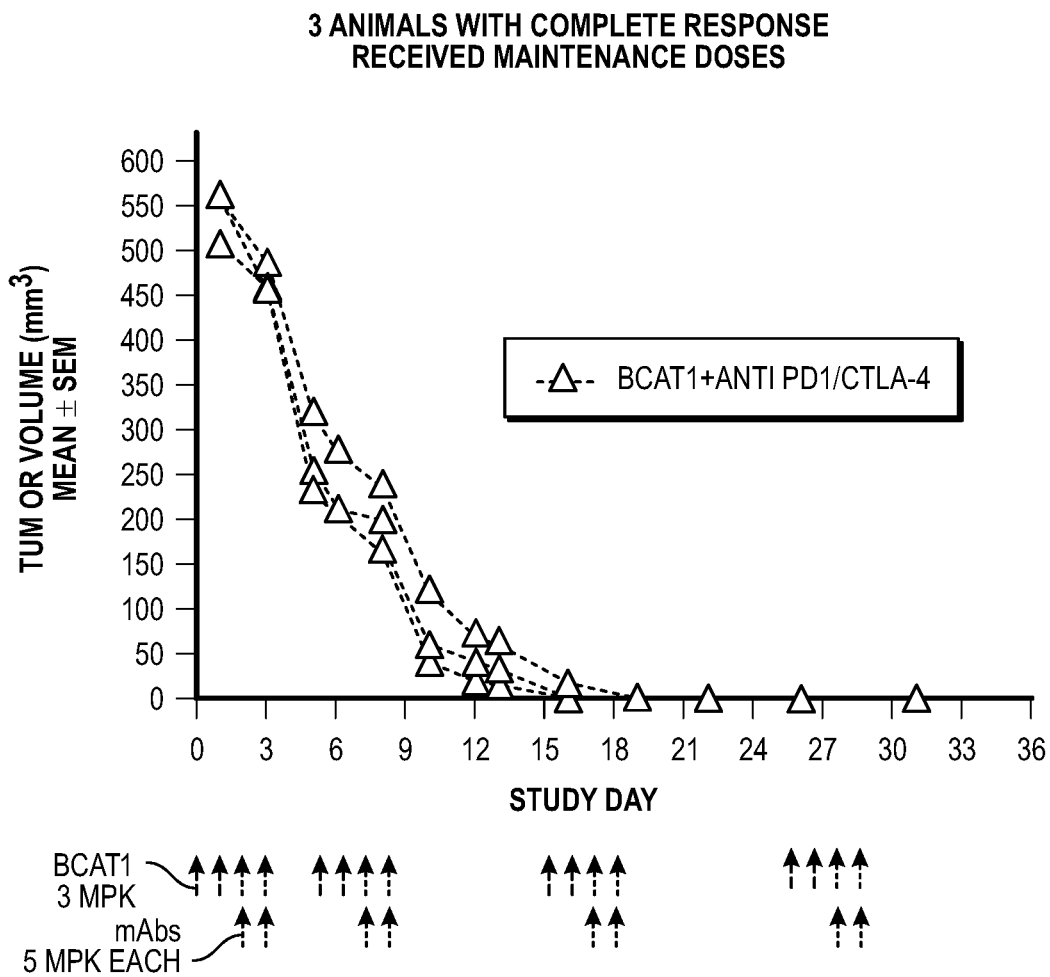
FIG. 9C shows that the three mice with complete tumor regression following completion of the Cycle 1 treatment schedule remained tumor free when treated with maintenance doses of BCAT1 and anti-PD-1/CTLA-4.
FIG. 10 shows one non-limiting embodiment of a double-stranded β-catenin nucleic acid inhibitor molecule, having of a sense (or passenger) strand (SEQ ID NO: 1) and an antisense (guide) strand (SEQ ID NO: 2). This β-catenin nucleic acid inhibitor molecule is referred to herein as BCAT1.

A nucleic acid inhibitor molecule that targets the β-catenin gene was constructed ("BCAT1"). BCAT1 has a 26 base pair passenger strand and a 38 base pair guide strand that form a duplex region consisting of 26 base pairs. FIG. 10. The 5' end of the guide strand consists of a 10-base pair, single stranded overhang, and the 3' end of the guide strand consists of a two-base pair single-stranded, overhang. FIG. 10.

The BCAT1 construct was formulated in EnCore lipid nanoparticles (LNP). The LNP formulated BCAT1 has been shown to effectively deliver the nucleic acid payload to multiple tumor types (see Table I below), including subcutaneous, orthotopic, disseminated and metastatic xenograft tumors, patient-derived xenografts (PDX), and genetically engineered models (GEM).

TABLE I

Delivery of BCAT1 to Various Tumor Types

| Tumor type | Description | Tumor location in model |
|---|---|---|
| Acute lymphoblastic leukemia | ALL697 | disseminated/spleen |
| Acute lymphoblastic leukemia | NALM-6 | disseminated/spleen |
| Acute myelogenous leukemia | KG1 | disseminated/spleen, liver |
| Breast | MMTV-Wnt1 | Spontaneous/mammary |
| Breast | 4T1 | Subcutaneous/flank |
| Colorectal | LS411N CLDX | metastases/liver, primary/spleen |
| Colorectal | SW403 CLDX | metastases/liver |
| Colorectal | LS174T CLDX | metastases/liver, primary/spleen |
| Colorectal | SW1116 CLDX | primary/spleen |
| Colorectal | LS411N CLDX | subcutaneous/flank |
| Colorectal | SW403 CLDX | subcutaneous/flank |
| Colorectal | LS1741 CLDX | subcutaneous/flank |
| Colorectal | PDX | subcutaneous/flank |
| Hepatoblastoma | liver-specific GEMM/CTNNB1-YAP | spontaneous/liver |
| Hepatoblastoma | HepG2 CLDX | subcutaneous/flank |
| Hepatoblastoma | HepG2 CLDX | orthotopic/liver |
| Hepatocellular Carcinoma | Hep3B CLDX | subcutaneous/flank |
| Hepatocellular Carcinoma | Hep3B CLDX | orthotopic/liver |
| Hepatocellular Carcinoma | PDX | orthotopic/liver |
| Hepatocellular Carcinoma | GEMM/Mst1 | spontaneous/liver |
| Hepatocellular Carcinoma | liver-specific GEMM/CTNNB1-KRAS | spontaneous/liver |
| Hepatocellular Carcinoma | liver-specific GEMM/Myc | spontaneous/liver |
| Lung | Lewis Lung Carcinoma | subcutaneous/flank |
| Melanoma | B16F10 CLDX | subcutaneous/flank |
| Melanoma | B16F10 CLDX | disseminated/lung, liver |
| Melanoma | A2058 | Subcutaneous/flank |
| Multiple Myeloma | KMS11 | subcutaneous/flank |
| Neuroblastonna | Neuro2A | Subcutaneous/flank |
| NSCLC | PDX | subcutaneous/flank |
| Osteosarcoma | PDX | subcutaneous/flank |
| Ovarian | PDX | subcutaneous/flank |
| Pancreatic | MiaPaca2 | subcutaneous/flank |
| Pancreatic | PDX | subcutaneous/flank |
| Renal Cell Carcinoma | 786/0 | subcutaneous/flank |

Negative: HCT116, DLD1, HL60

Example 2: Tumor Studies 6-8 week old immunocompetent mice (C57BL/6 or NJ or Balb/C) were injected subcutaneously with $1\times10^6$ B16F10, $2\times10^6$ Neuro2A, $1\times10^6$ Renca, or $2\times10^6$ 4 T1 cells under the right shoulder. Tumor volume was measured every 2-3 days to monitor tumor growth. Dosing was initiated when the tumors reached about 100 mm³. For tumor growth inhibition studies, animals were randomized and assigned to different cohorts and subjected to dosing cycles. BCAT1 or Placebo (LNP with scrambled CTNNB1 dsRNAi inhibitor molecule) was given intravenously via lateral tail vein at a total volume of 10 ml/kg. Immunotherapy treatments (anti-PD-1 and anti-CTLA-4 antibodies) were given intraperitoneally at a volume of 10 ml/kg.

Figure 2A:
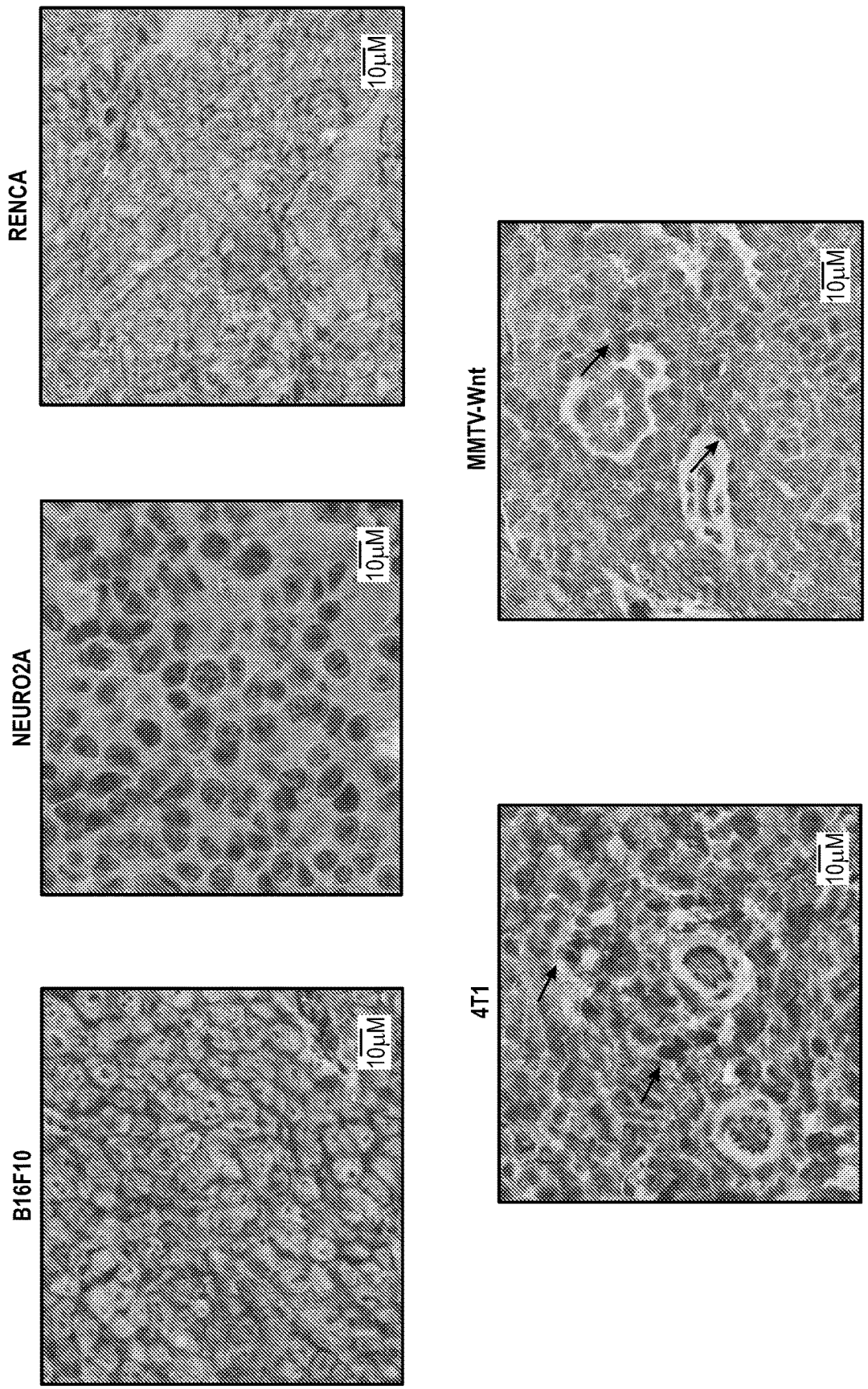
FIG. 2A shows by immunohistochemistry (40×) that β-catenin localizes in nucleus of the 4T1 cell line and spontaneous MMTV-Wnt1 tumors, both of which have an activated Wnt pathway, but does not localize in the nucleus of the non-Wnt activated cell lines, Neuro 2A, B16F10, and Renca.

Mouse cell lines B16F10, Neuro2A, Renca and 4T1 cells were obtained from ATCC (Manassas, Va.) and grown in RPMI/DMEM medium supplemented with 10% FBS. B16F10 is a murine melanoma cell line with no Wnt activation. Neuro2A is a murine neuroblastoma cell line with no Wnt activation. Renca is a murine renal cancer cell line with no Wnt activation. 4T1 is a murine breast cell line having an activated Wnt pathway. MMTV-Wnt mammary tumors spontaneously grow in mice in 3-6 months from the time of birth with Wnt pathway activation. Nuclear staining of β-catenin is a hallmark of an activated Wnt/β-catenin pathway. Kawakami et al., 2013, Frontiers in Oncology, 3(136):1-7; Segditsas and Tomlinson, 2006, Oncogene, 25:7531-37; Clevers, H., 2006, Cell 127:469-480. B16F10, Neuro2A, and Renca cells, had no nuclear localization of β-catenin, as measured by immunohistochemistry, whereas the 4T1 cell line and spontaneous MMTV-Wnt tumors, both exhibited nuclear localization of β-catenin. FIGS. 2A-B.

Figure 3A:
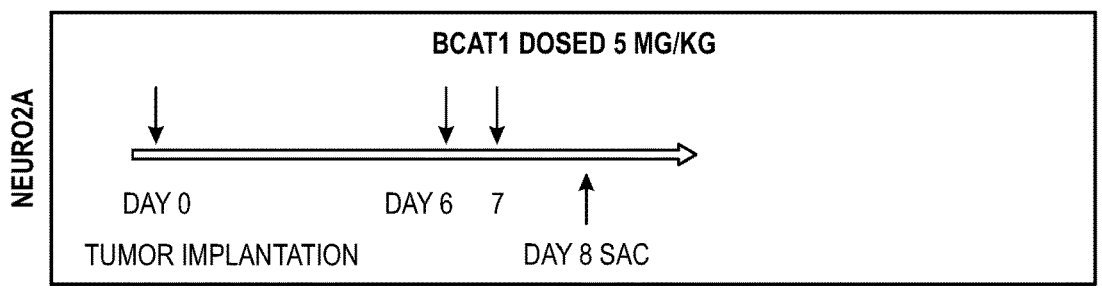
FIG. 3A shows the treatment schedule for A/J mice that were implanted with non-Wnt activated, Neuro2A tumors and treated with PBS or BCAT1, as described in Example 3.

Example 3: Inhibiting β-Catenin Enhances T Cell Infiltration in Tumors without Wnt Activation Neuro2A To investigate whether specific pharmacological inhibition of Ctnnb1 mRNA impacts immune cell subpopulations, Neuro2A tumor cells were implanted subcutaneously in NJ mice. As noted above, Neuro2A is a murine neuroblastoma cell line with no Wnt activation. At six days post Neuro2A tumor cell implantation, with the average tumor size of 100 mm³, the NJ mice with tumors were sorted into 2 groups (n=5) and were treated with either PBS or BCAT1 at 5 mg/kg for 2 days (qdx2, 5 mg/kg) as shown in FIG. 3A.

Figure 3B:
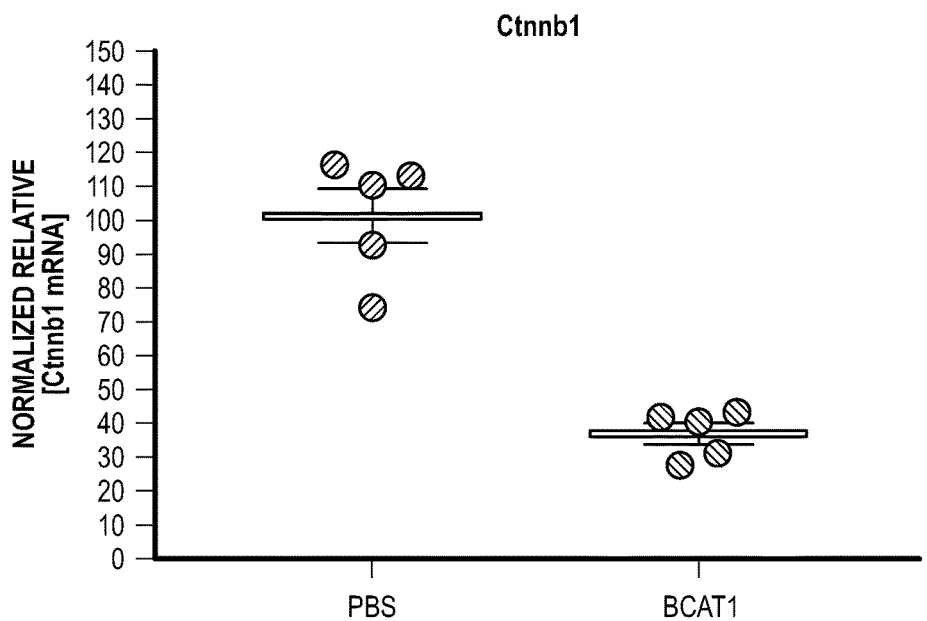
FIG. 3B shows that a single treatment cycle with BCAT1 in mice implanted with Neuro2A tumor cells, which do not have an activated Wnt pathway, reduces β-catenin mRNA expression, has no affect on the Wnt/β-catenin responsive marker, cMyc, and enhances mRNA expression of immune cells markers (CD8), chemokines (CCL4) and checkpoints that are involved in T cell infiltration and activation (PD-1, PD-L1).
Figure 3B:
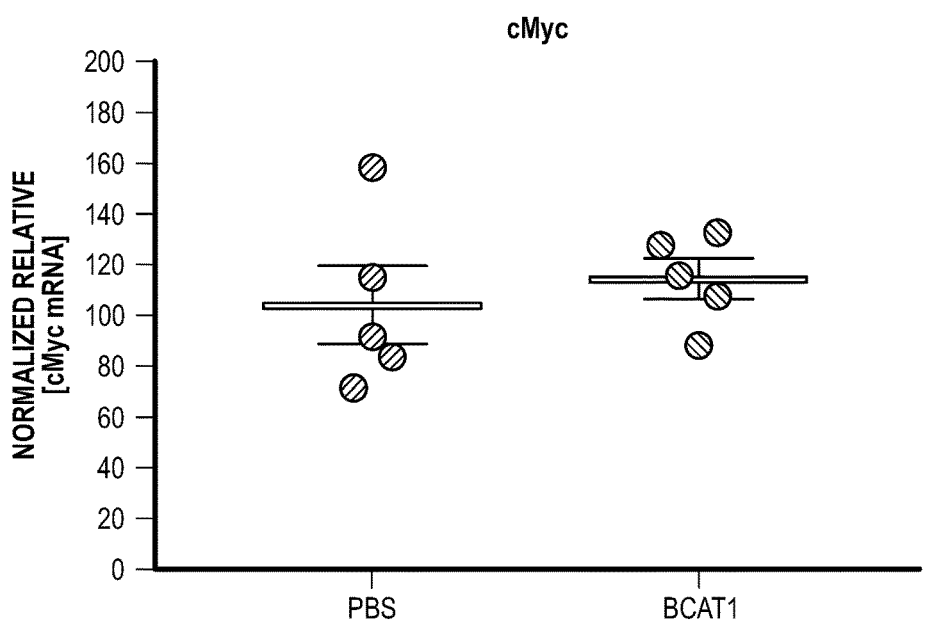
Figure 3B:
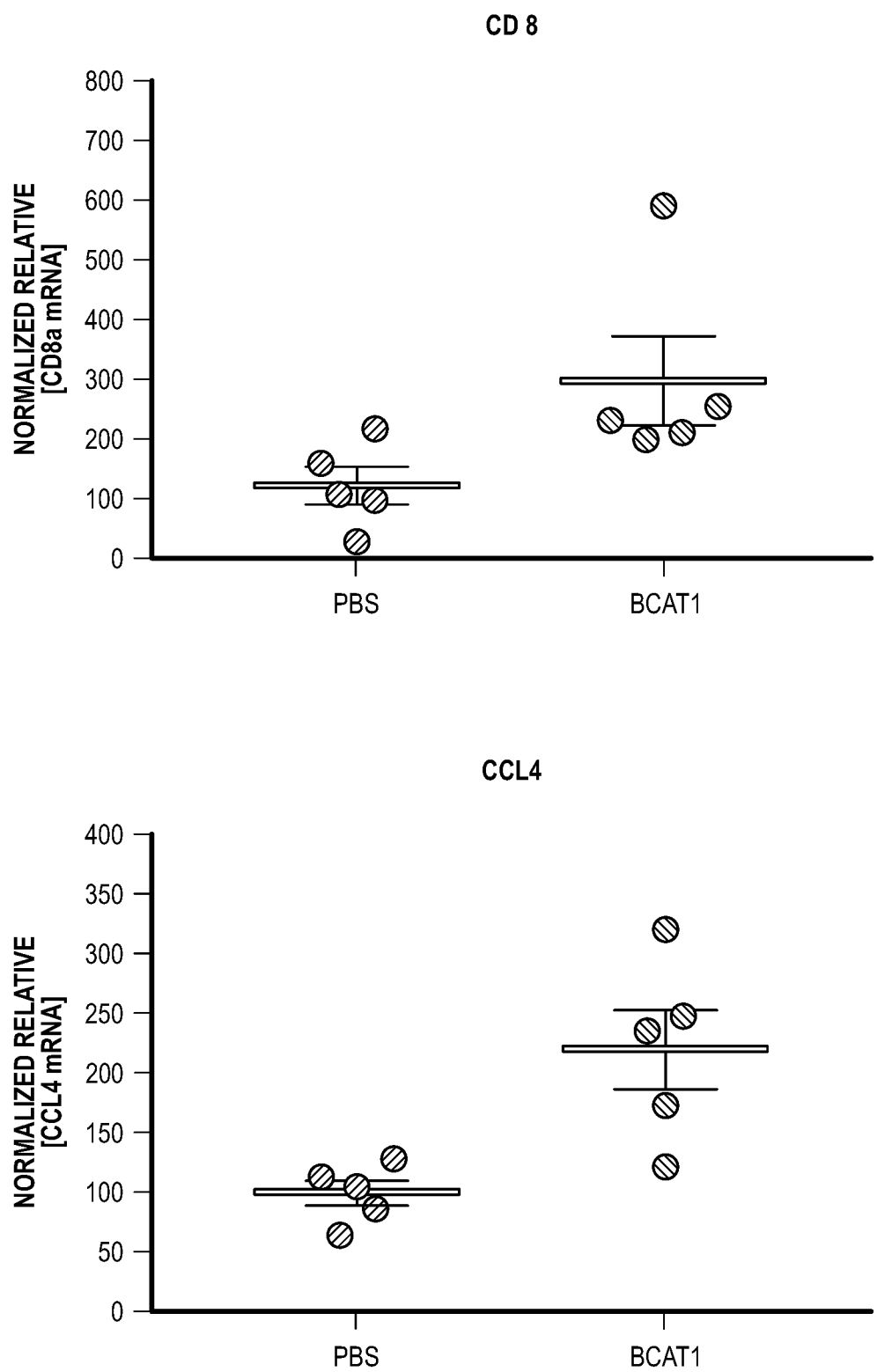
Figure 3B:
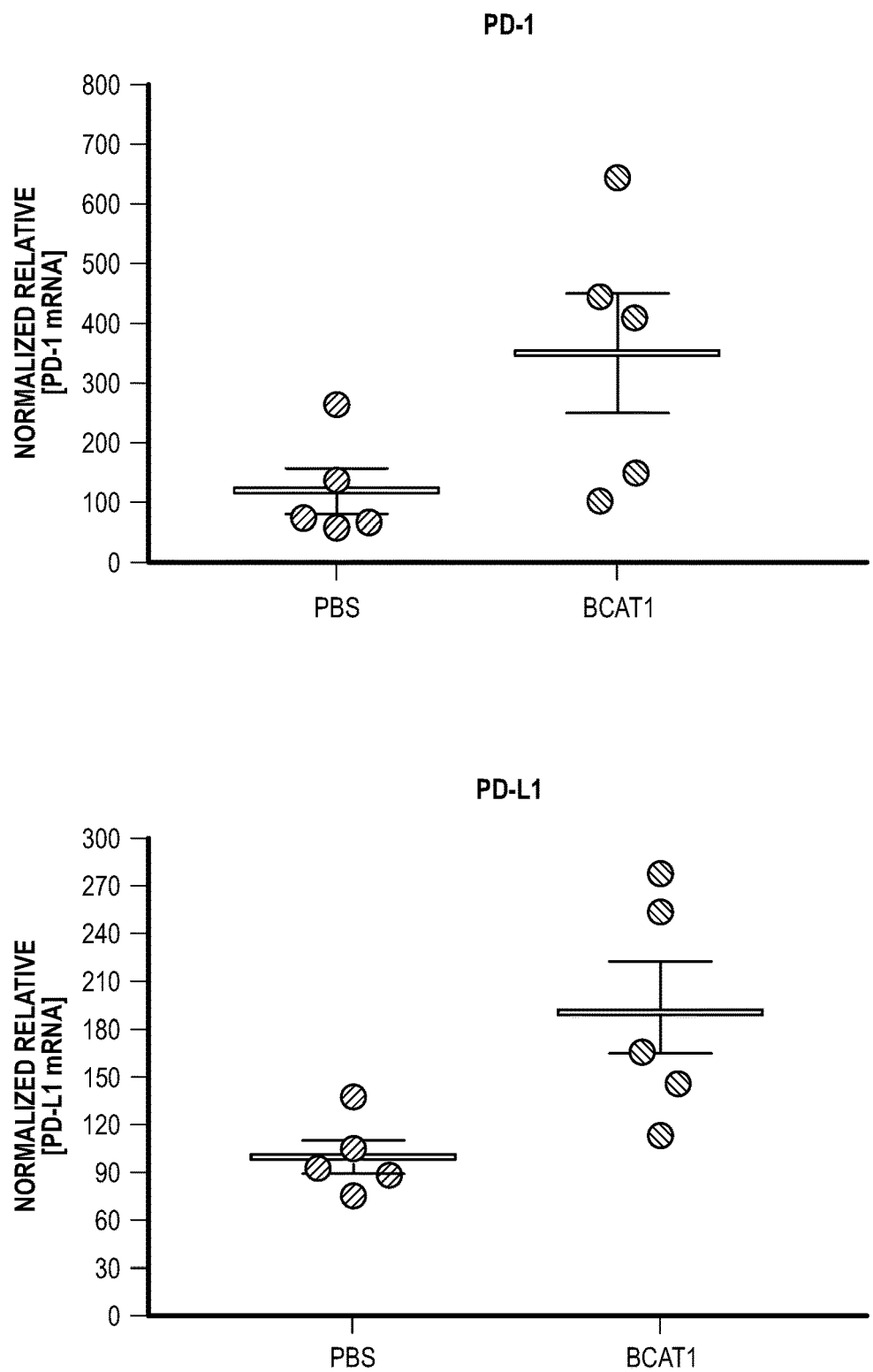
Figure 4A:
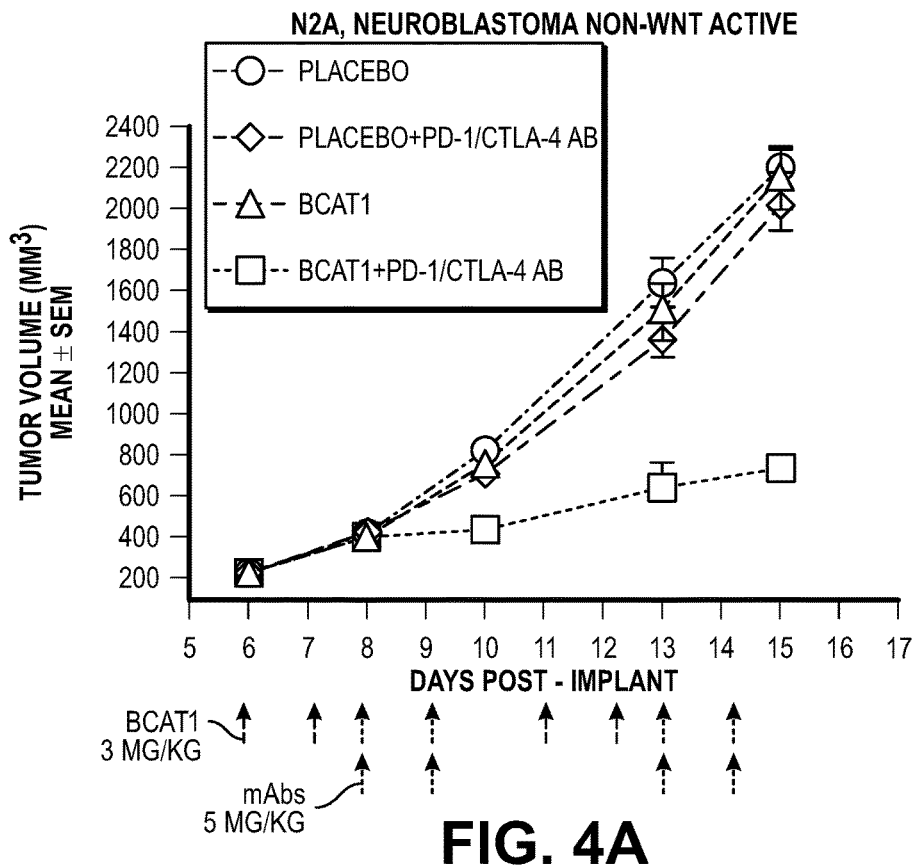
FIGS. 4A-D demonstrate that combination therapy with BCAT1 and checkpoint molecule inhibitors (anti-PD-1/anti-CTLA-4 antibodies) results in significant tumor growth delay compared to either BCAT1 alone or a combination of Placebo and the checkpoint molecule inhibitors in tumors with an activated Wnt pathway, such as 4T1 (C) and even in tumors without an activated Wnt pathway, such as Neuro2A (A), B16F10 (B), and Renca (D).

Twenty-four hours after the last dose, tumors were collected and analyzed by qPCR for mRNA levels of Wnt/β-catenin responsive markers (cMyc), immune cell markers (CD8 and CD3), chemokines (CCL4), and immune checkpoints (PD-1 and PD-L1). In tumors from mice treated with BCAT1, there was no change in the mRNA levels of cMyc. FIG. 3B. cMyc is a β-catenin target gene that is known to be upregulated in tumors having an active Wnt/β-catenin pathway (Scholer-Dahirel et al., 2011, PNAS, 108(41): 17135-40) and, thus, serves as a Wnt/β-catenin marker. Although expression levels of the β-catenin gene (Ctnnb1) decreased about 50-60% as compared to control levels in tumors from mice treated with BOAT (FIG. 3B), there was no change in cMyc expression levels. If Neuro2A cells have an active Wnt/β-catenin pathway, one would expect cMyc expression to be downregulated in these tumors when β-catenin expression was downregulated. Here, it was not. In addition, nuclear localization of β-catentin was not observed in Neuro2A cells (FIGS. 2A-B), and the BCAT1-mediated reduction of β-catentin was not associated with any reduction in tumor growth (FIG. 4A). Combined with the unchanged levels of cMyc expression, these results indicate that Neuro2A cells do not have an activated Wnt pathway. Accordingly, the BCAT1-mediated reduction of β-catenin in these tumors is not expected to be associated with any reduction in tumor growth.

BCAT1-treated tumors had significantly increased levels of the immune cell markers, tumor cell markers, and checkpoint molecules analyzed. More specifically, there was a significant increase in the levels of CD8, CCL4, PD-1 and PD-L1 after BCAT1 treatment. FIG. 3B. These data from the Neuro2A tumor model confirm that the inhibition of β-catenin increases the expression of key T cell markers (CD8), chemokines (CCL4) and checkpoint molecules (PD-1 and PD-L1) and unexpectedly suggests that inhibiting β-catenin expression, even in tumors without an activated Wnt/β-catenin pathway, can convert a non-T cell inflamed phenotype to a T cell-inflamed phenotype.

B16F10

As noted above, B16F10 is a non-Wnt activated tumor. B16F10 tumors are also known to be refractory to immune checkpoint therapy. Thus, B16F10 tumors were used to further investigate how specific pharmacological inhibition of Ctnnb1 mRNA impacts immune cell subpopulations and relevant signaling intermediates in a model of murine melanoma. B16F10 tumors were subcutaneously allografted into immunocompetent C57BL/6 mice. After the tumors reached a volume of 250 mm$^3$, BCAT1 or a placebo (a scrambled DsiRNA with matched chemistry and formulation), along with a separate vehicle control, were administered intravenously via tail vein, according to the dosing regimen shown in FIG. 12A (n=5-6/cohort).

Tumors were excised for pharmacodynamic endpoint analysis after treatment. Quantitative PCR (qPCR) measurements using total RNA isolated from the tumor shows that BCAT1 caused a partial reduction in Ctnnb1 mRNA and concomitant increase in the Ccl4 mRNA (FIG. 12B). As β-catenin has been previously shown to cause immune evasion, in part, by transcriptional repression of Ccl4, the alleviation of Ccl4 repression is associated with robust increases in the dendritic cell mRNA marker Itage, which encodes CD103, and the cytotoxic T-cell mRNA markers Cd8a (FIG. 12B). Flow cytometry was then performed to measure surface markers on single-cell suspensions prepared from the extracted B16F10 tumors (FIG. 12C). While the placebo had no significant effect on the tumor immune compartment, BCAT1 treatment resulted in highly significant increases in total T-cells (CD3), cytotoxic T-cells (CD8), antigen-presenting dendritic cells (CD103), and the PD-1 T-cell checkpoint (FIG. 12C).

Figure 13A:
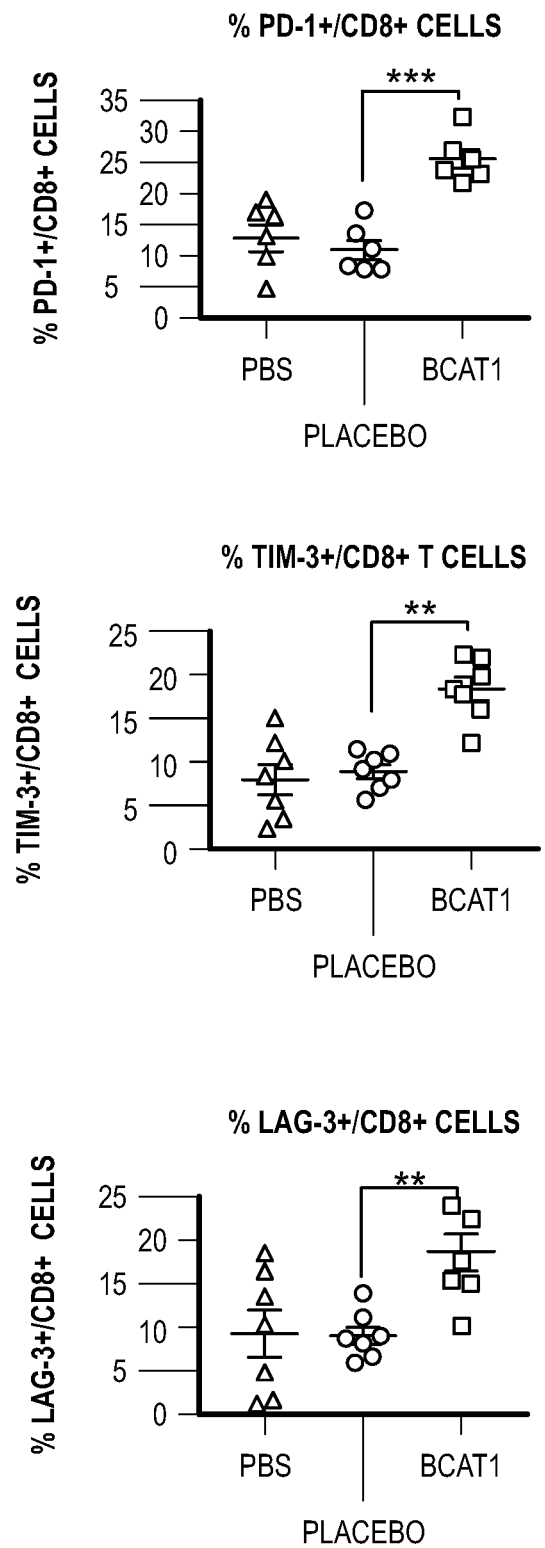
FIGS. 13A-B show by flow cytometry of the tumor microenvironment that a single treatment cycle with BCAT1 in C57BL/6 mice with grafted B16F10 tumors leads to an increase in three different T-cell receptor cofactors expressed on CD8+ T cells (PD-1, TIM-3 and LAG-3) (A); and minimal to no observed treatment-related effects on tumor-associated natural killer (NK) cells, myeloid derived suppressor cells (MDSCs), or Regulatory T-cells (Tregs) (B).
Figure 13B:
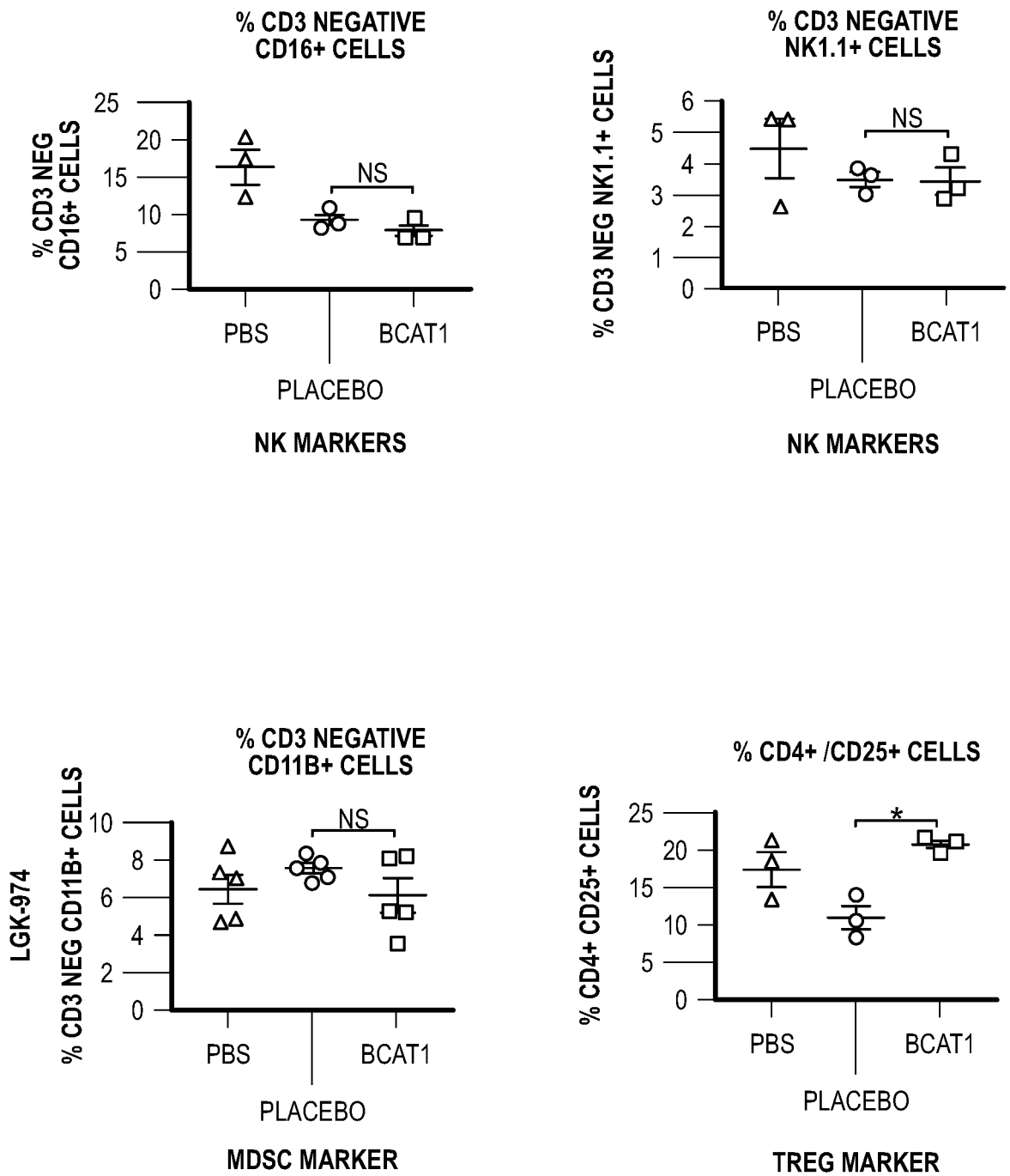

Additional flow cytometry analyses showed a treatment-associated increase in three different T-cell receptor (TCR) cofactors known to be checkpoints within CD8+ T-cells: PD-1, TIM-3 and LAG-3 (FIG. 13A). In contrast to the robust increase in tumor T-cell content, there were no observed treatment-related effects on tumor-associated natural killer (NK) cells, another important subpopulation known to modulate response to immunotherapy (FIG. 13B). Similarly, changes in immunosuppressive myeloid derived suppressor cells (MDSCs) and Regulatory T-cells (Tregs) after treatment were minimal and variable (FIG. 13B). These data suggest that recruitment of cytotoxic T-cells is a dominant mechanism of immunomodulation mediated by β-catenin inhibition.

Figure 12A:
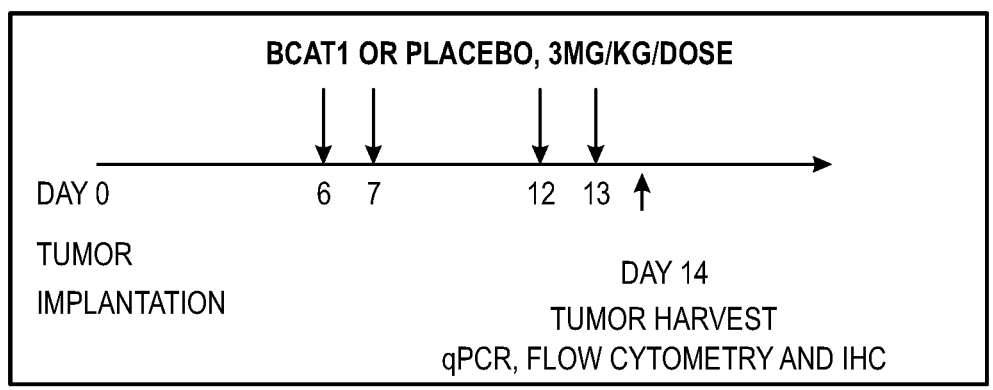
FIG. 12A shows the treatment schedule for C57BL/6 mice that were subcutaneously allografted with non-Wnt activated, B16F10 tumors and treated with Placebo or BCAT1, as described in Example 3.
Figure 12B:
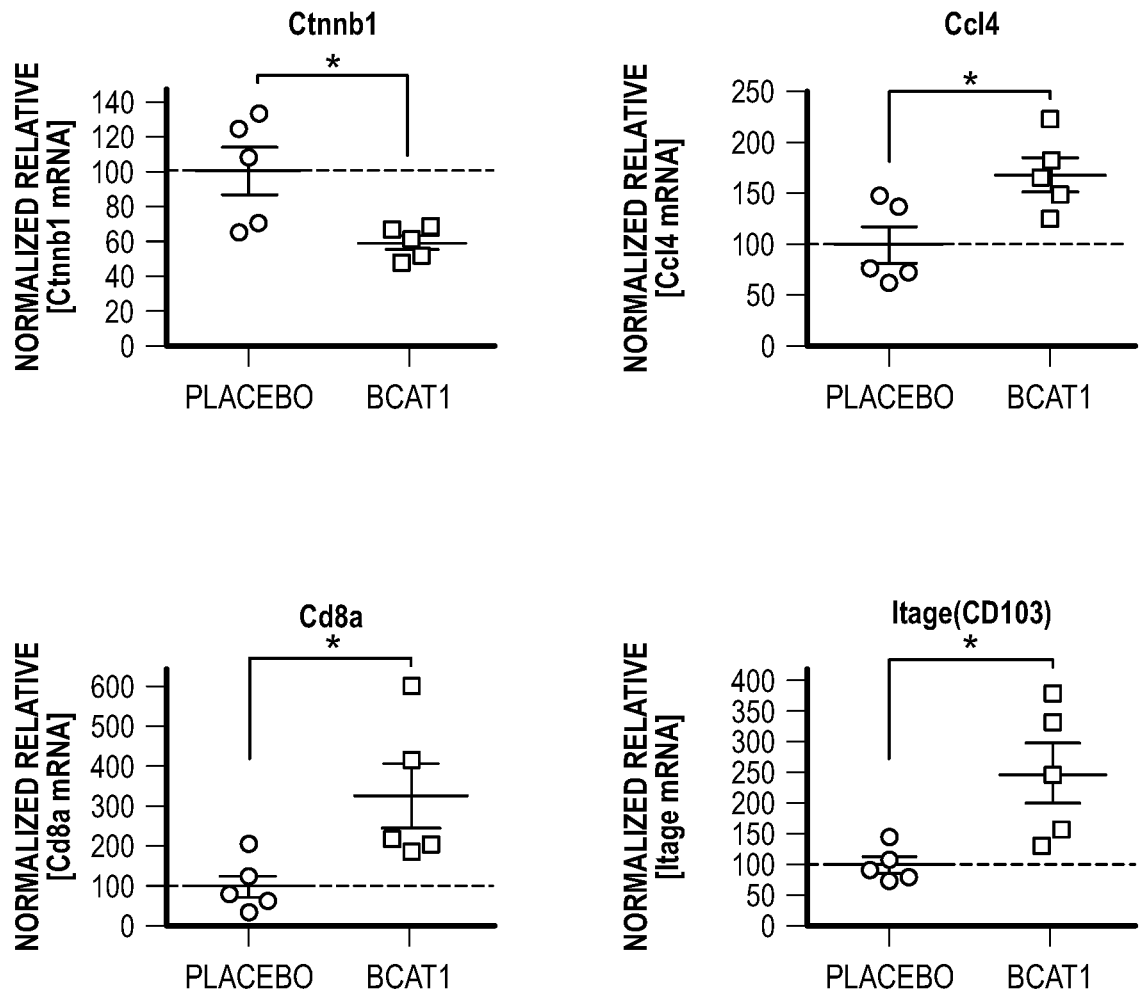
FIGS. 12B-D show that a single treatment cycle with BCAT1 in C57BL/6 mice with grafted B16F10 tumors leads to partially reduced levels of β-catenin (Ctnnb1) mRNA and a concomitant increase in CCL4, CD8a, and Itage (CD103) mRNA as measured by qPCR (B); increased CD3, CD8, CD103, and PD-1 expression in the tumor microenvironment as measured by flow cytometry (C); and reduced levels of β-catenin protein and increased levels of CD8 protein as measured by immunohistochemistry (IHC) (D).
Figure 12C:
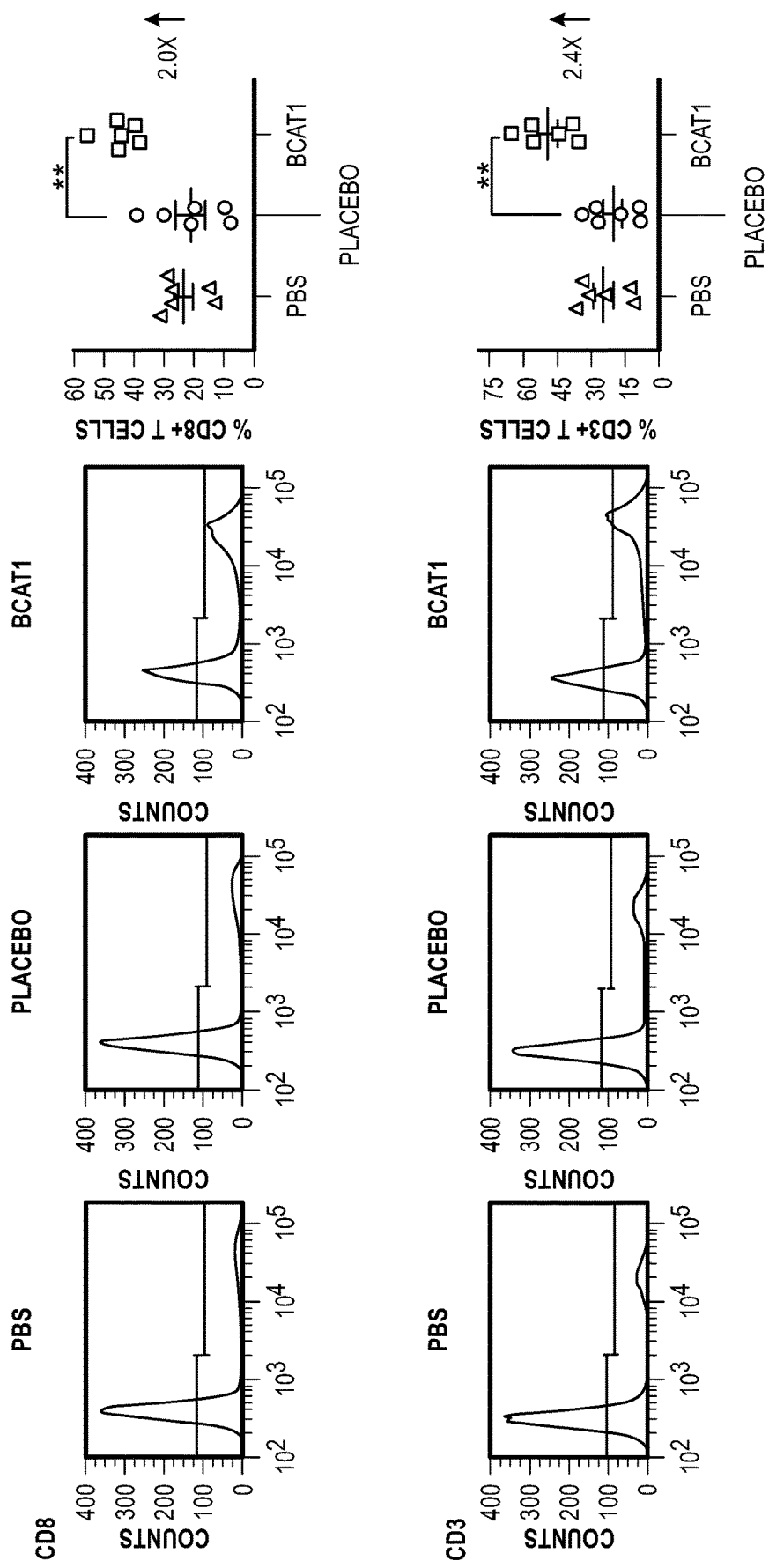
Figure 12C:
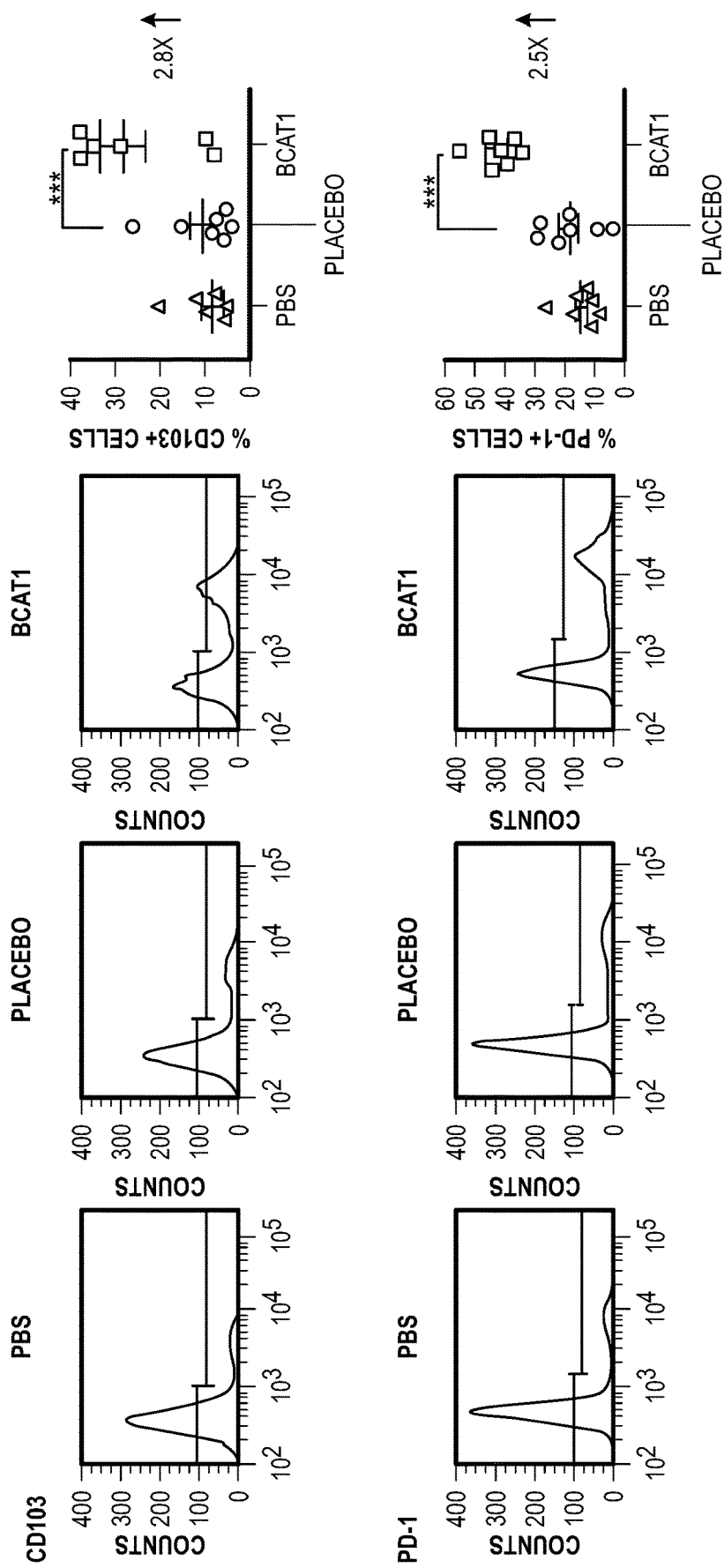
Figure 12D:
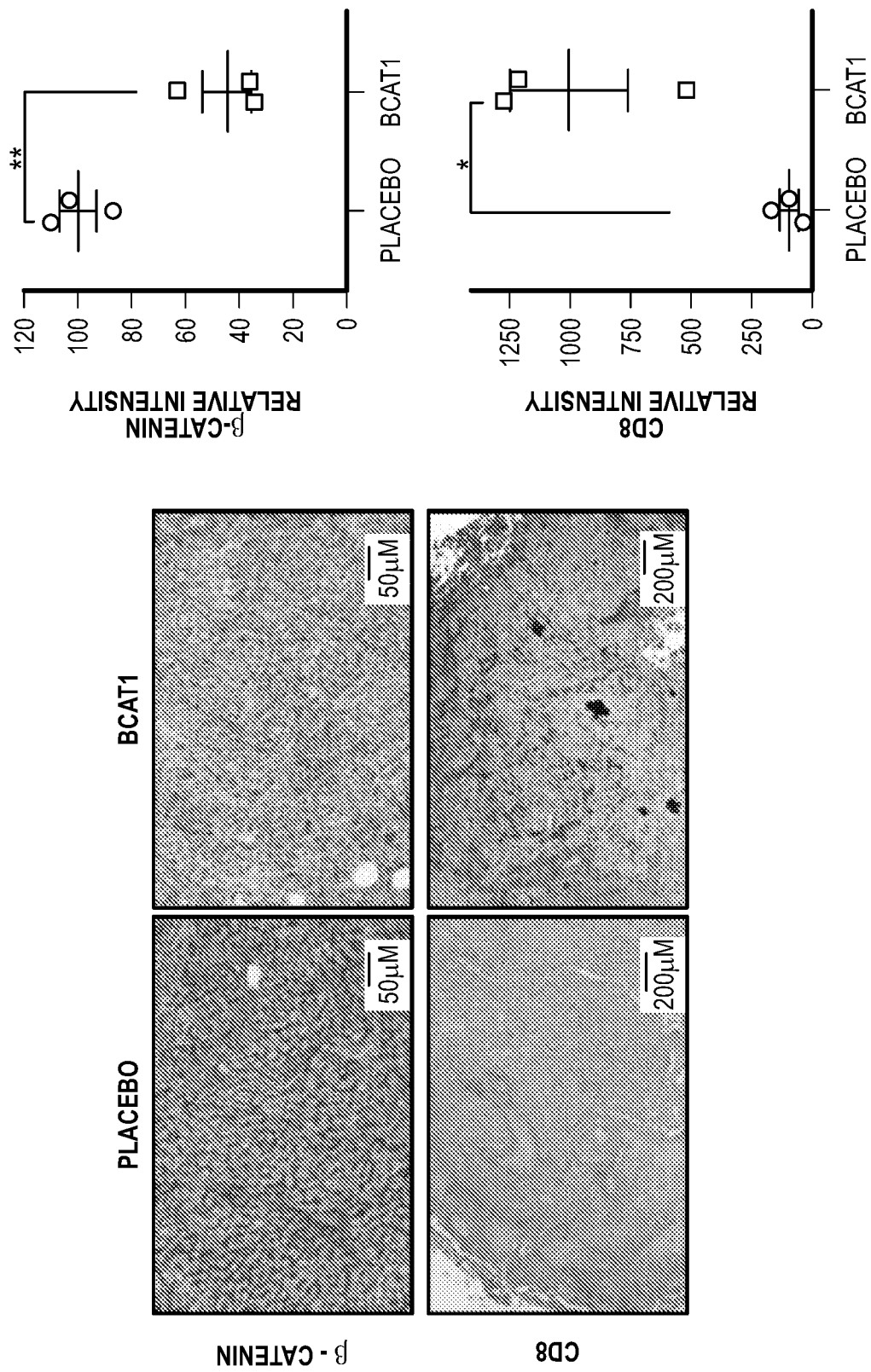

Finally, immunohistochemistry (IHC) for β-catenin and CD8 proteins, performed on formalin-fixed, paraffin-embedded (FFPE) B16F10 tumor tissue, provided further confirmation of the BCAT1 treatment effects (FIG. 12D). Loss of β-catenin protein after BCAT1 therapy (approximately 60% decrease in relative intensity) is homogeneous throughout the tumor section, and is observed in both the cell membrane and the cytosol of B16F10 tumors. In the native state, the B16F10 tumors are negative for CD8, consistent with their immunologically "cold" status. After two rounds of BCAT1 treatment, CD8 staining was observed throughout the tumor (FIG. 12D). Collectively, the qPCR, flow cytometry and IHC data demonstrate that inhibiting Ctnnb1 expression in the non-Wnt activated B16F10 tumors increases the population of tumor-associated APCs and T lymphocytes, both of which are known to have positive predictive value for response to immunotherapy. BCAT1-treated tumors had significantly increased levels of the immune cell markers, tumor cell markers, and checkpoint molecules analyzed. More specifically, there was a significant increase in the levels of CD8, CCL4, CD103 and PD-1 after BCAT1 treatment.

Example 4: Inhibiting β-Catenin Enhances the Expression of the NF-κB-Responsive Genes, Cxcl10 and Cxcl11, in Non Wnt Activated Tumors Given the observation that steady-state nuclear β-catenin was not required for its immune modulating function in tumors, the possible role for indirect, noncanonical mechanisms was explored. β-catenin is known to interact directly with NF-κB transcription complexes and inhibit its transcriptional activity through sequestration, an event which may contribute to immunosuppression in a subset of liver, breast and colorectal tumors (Deng et al; 2002, Cancer cell, 2(4):323-34; Du et al; 2009, Cancer Res, 69(9): 3764-71; Moreau et al; 2011, Int J Cancer, 128(6):1280-92.). Chemokines CXCL10 and CXCL11 are known to be highly responsive to NF-κB signaling (Huang et al; 2015, FASEB J, 29(1): 227-38).

Figure 14A:
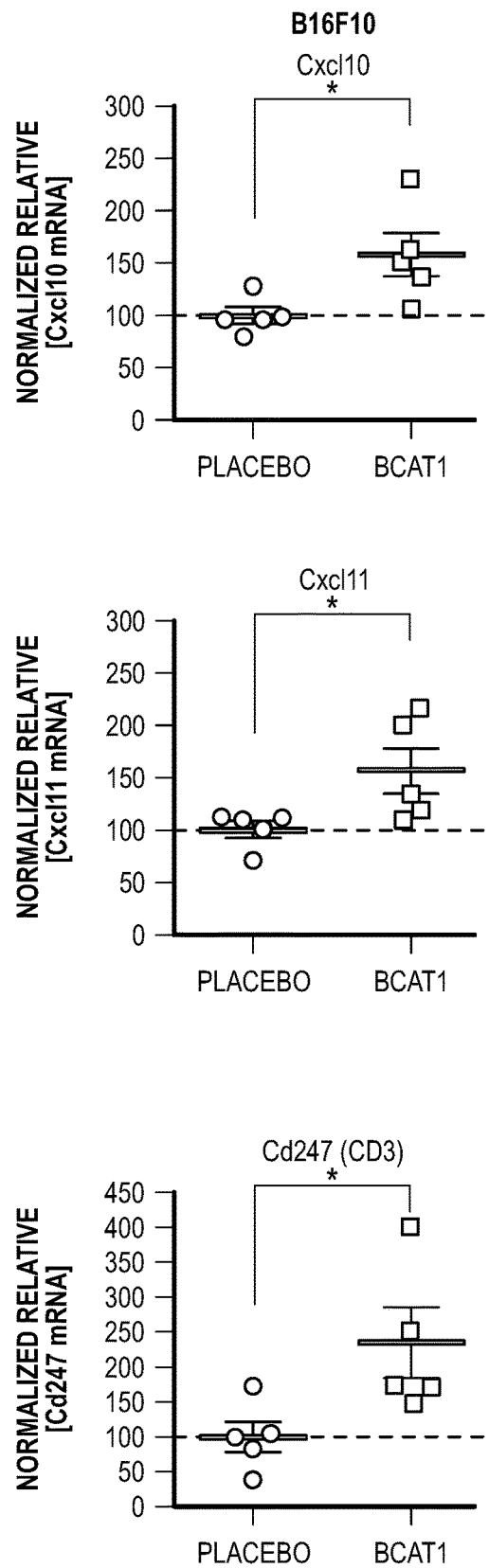
FIGS. 14A-B show that a single treatment cycle with BCAT1 causes upregulation of Cxcl10, Cxcl11, and CD3 mRNA in mice grafted with B16F10 tumors (A) and mice implanted with Neuro2A tumors (B).
Figure 14B:
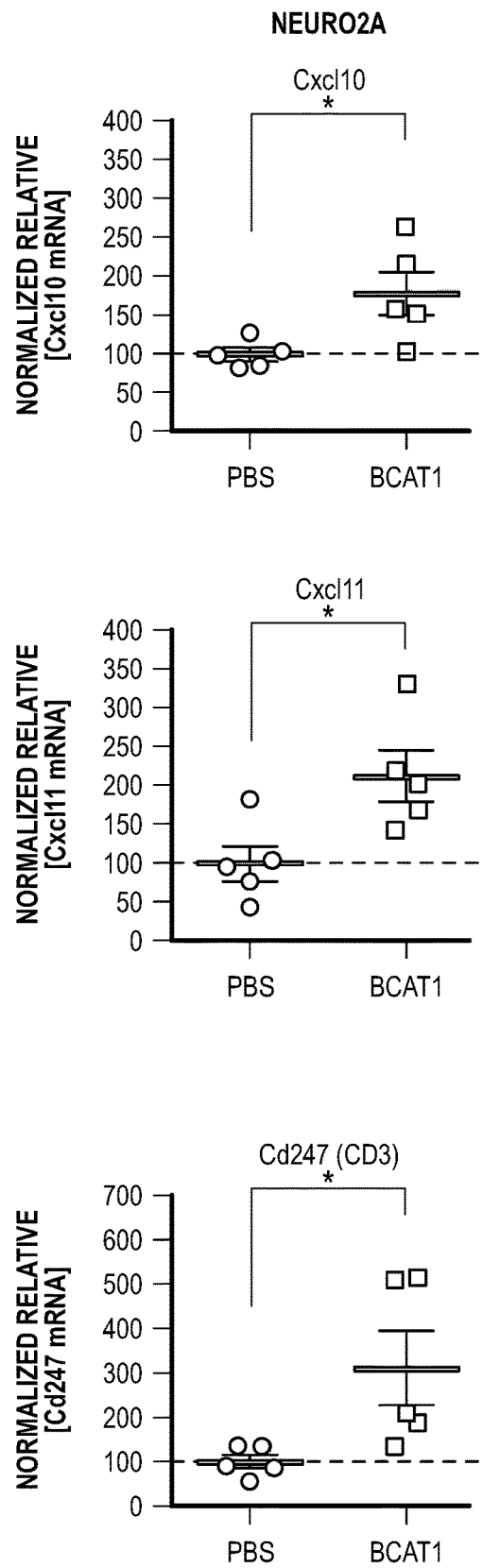

Mice harboring Neuro2A and B16F10 tumors were treated with BCAT1 according to the schedules set forth in in FIGS. 3A and 12A, respectively. Systemic BCAT1 therapy caused upregulation of the corresponding mRNAs encoding Cxcl10, Cxcl11, and CD3 in both B16F10 and Neuro2A syngeneic tumors (FIGS. 14A-B). Without intending to be bound by any theory, it is possible that the pharmacological inhibition of β-catenin in the non Wnt-activated setting reverses β-catenin's suppression of inflammatory genes, in part, by restoring NF-κB activity/signaling.

Interestingly, NF—KB is also known to cross talk with the ATF3 transcriptional repressor, possibly explaining β-catenin's effects on CCL4 even in the non-Wnt activated tumor context.

Example 5: Combining β-Catenin Inhibition and Immunotherapy Significantly Inhibits Growth of Tumors with and without Wnt Activation Combination therapy with BCAT1 and immune checkpoint inhibitors (anti-PD-1 and anti-CTLA4 antibodies) was evaluated in tumors with (4T1) and without Wnt activation (B16F10, Neuro2A, and Renca). The anti-PD-1 antibody and anti-CTLA4 antibody (99% purity) were provided in PBS at 6.66 and 5.4 mg/ml concentration, respectively. This solution was further diluted in PBS and administered intraperitoneally as described above. BCAT1 or Placebo (LNP with scrambled CTNNB1 dsRNAi inhibitor molecule) was given intravenously as described above.

B16F10 cells were implanted in C57BL/6 mice and 5 days post implantation, with an average tumor size of 100 mm$^3$, the mice were sorted into 4 groups (n=5). The dosing schedule is summarized in FIG. 4B. Groups 1 and 3 received two doses of Placebo, while groups 2 and 4 received two doses of BCAT1 at 3 mg/kg (qdx2) on days 5 and 6 post-implantation. Twenty-four hours after the last dose of Placebo or BCAT1, groups 3 and 4 received a combination of anti-PD-1/CTLA-4 antibodies intraperitoneally at 5 mg/kg on days 7 and 9. This combination dosing cycle was then repeated starting on day 11 and continuing through day 15. Tumor growth was monitored by measuring the tumor sizes over the course of the treatment period.

Figure 4B:
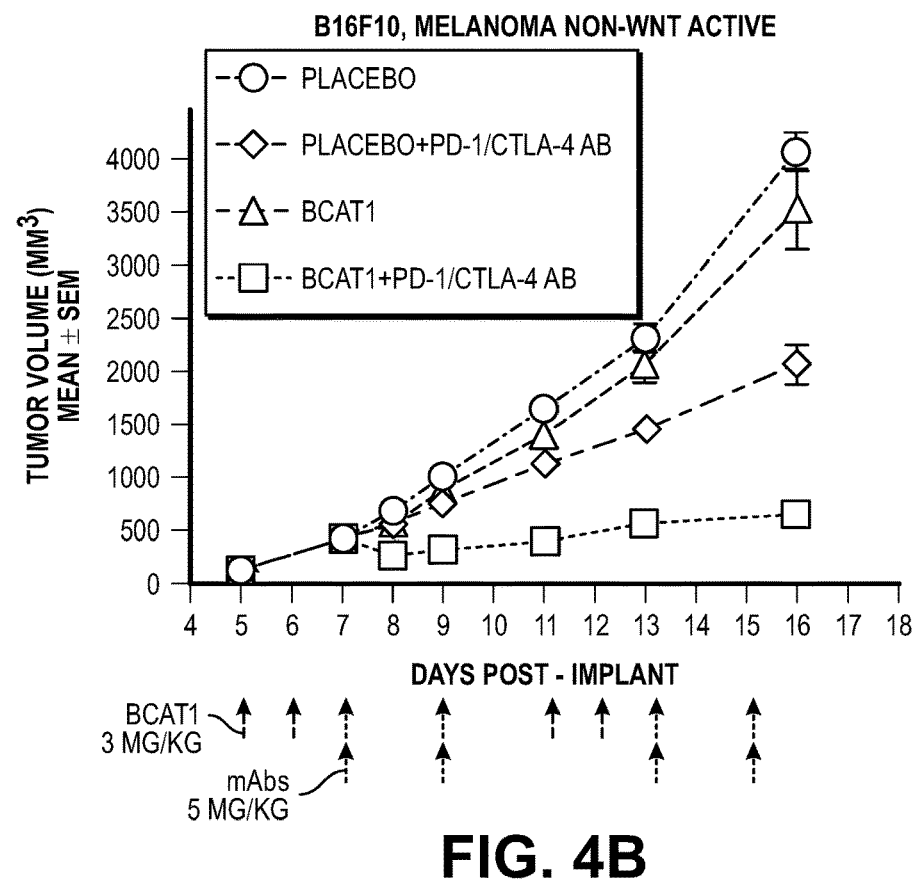

The groups of mice that received Placebo or BCAT1 alone (monotherapy) did not demonstrate any reduction in tumor growth. Inhibiting β-catenin in B16F10 tumors was not expected to reduce tumor growth because these tumor cells do not have an activated Wnt pathway. Mice receiving the combination of Placebo pre-treatment followed by a combination of anti-PD1 and anti-CTLA4 antibodies showed a partial response. FIG. 4B. Administering BCAT1 before treatment with the anti-PD-1/CTLA-4 antibodies resulted in synergistic effects, demonstrating almost complete tumor growth inhibition. FIG. 4B. These results surprisingly show that β-catenin inhibition in non-Wnt activated tumors can potently increase the sensitivity of these tumors to immunotherapy.

The combination treatment was also evaluated in Neuro2A tumors (N2A, murine neuroblastoma). A/J mice were implanted with Neuro2A tumor cells and six days post implantation, with an average tumor size of 100 mm$^3$, the mice were sorted into 4 groups (n=5). The dosing schedule is summarized in FIG. 4A. Groups 1 and 2 received two doses of Placebo and groups 3 and 4 received two doses of BCAT1 at 3 mg/kg (qdx2) on days 6 and 7 post-implantation. Twenty-four hours after the last dose, groups 3 and 4 received a combination of anti-PD-1/CTLA-4 antibodies intraperitoneally at 5 mg/kg on days 8 and 9. This combination dosing cycle was then repeated starting on day 11 and continuing through day 14. Tumor growth was monitored by measuring the tumor sizes over the course of the treatment period.

Mice receiving BCAT1 alone (monotherapy) or anti-PD-1/CTLA-4 antibodies alone did not demonstrate any significant reduction in tumor growth, confirming that Neuro2A tumor cells were resistant to immunotherapy and consistent with a non-activated Wnt pathway. FIG. 4A. On the other hand, mice treated with BCAT1 before receiving anti-PD-1/CTLA-4 antibodies demonstrated significant tumor growth inhibition. FIG. 4A. The combination therapy generated synergistic results, with tumor reductions that were far greater than the sum of the agents alone. These results surprisingly show that β-catenin inhibition in a second, non-Wnt active tumor potently increased the sensitivity of these tumors to immunotherapy.

Figure 4C:
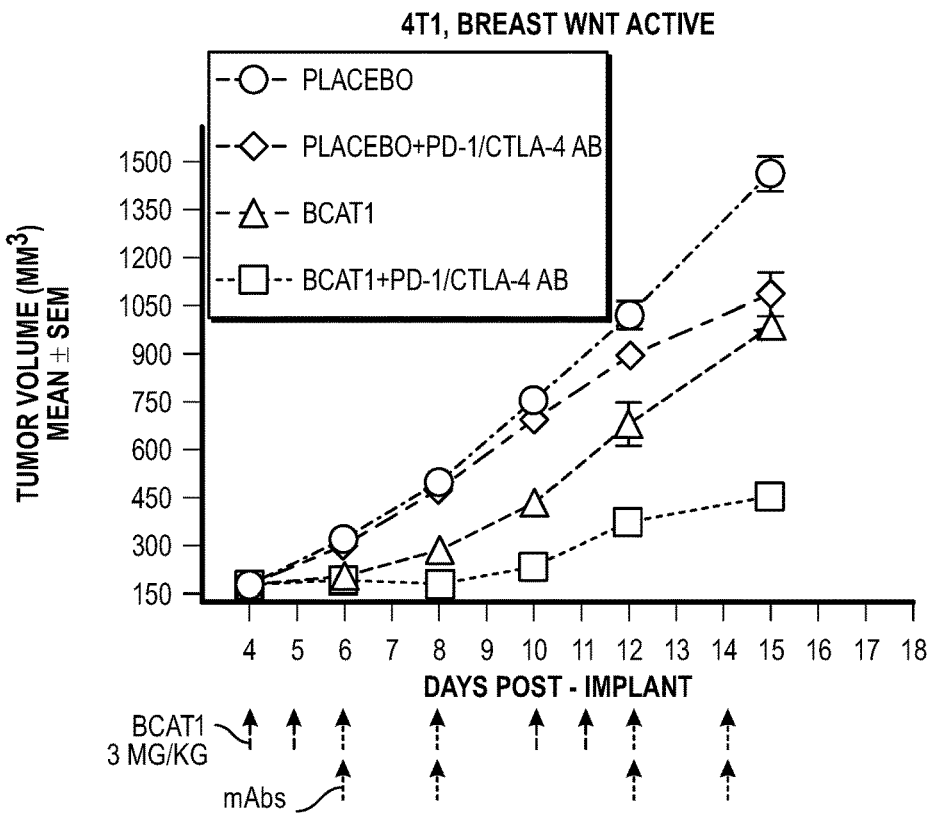
Figure 4D:
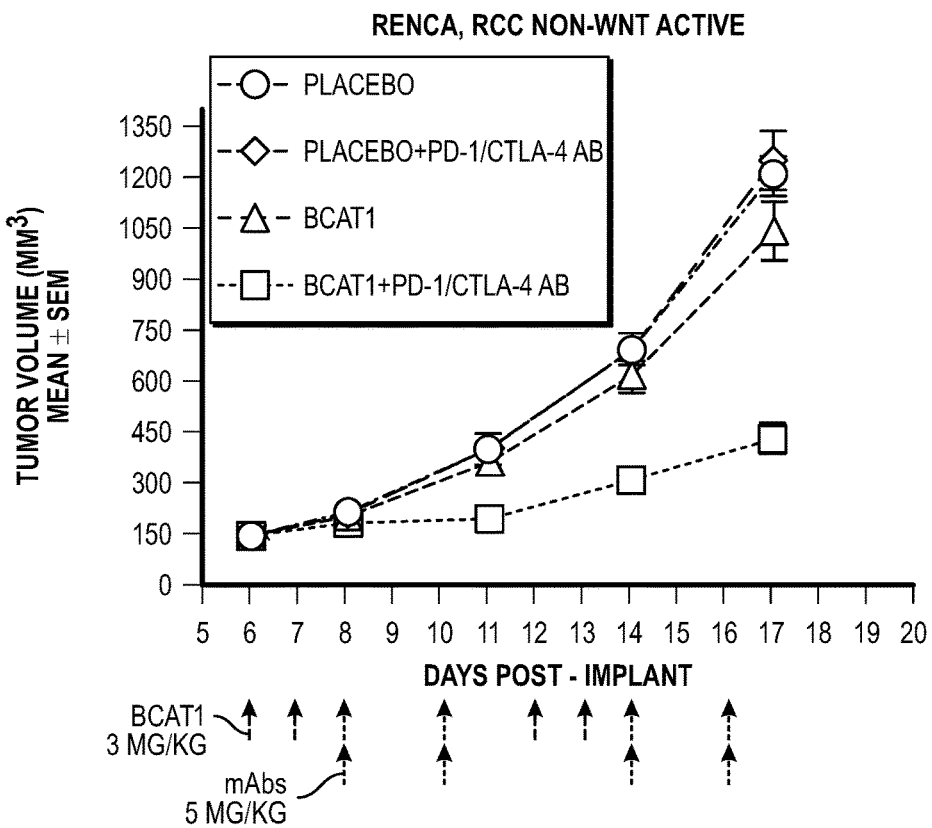

The combination treatment was also evaluated in Renca (a murine renal adenocarcinoma), another non-Wnt active tumor. Balb/C mice were implanted with Renca cells and six days post implantation, with an average tumor size of 100 mm$^3$, mice were treated with a combination of Placebo and anti-PD-1/CTLA-4 antibodies or a combination of BCAT1 and anti-PD-1/CTLA-4 antibodies, as shown in FIG. 4D. Mice were administered two doses of Placebo or BCAT1 at 3 mg/kg (qdx2) on days 6 and 7. Twenty-four hours after the last dose, mice were administered the anti-PD-1/CTLA-4 antibodies intraperitoneally at 5 mg/kg on days 8 and 10. This combination dosing cycle was then repeated starting on day 12 and continuing through day 16. Tumor growth was monitored by measuring the tumor sizes over the course of the treatment period.

In this model, mice receiving combination therapy with BCAT1 and the anti-PD-1/CTLA-4 antibodies showed significant tumor growth reduction compared to mice receiving only the anti-PD-1/CTLA-4 antibodies, once again demonstrating that inhibiting β-catenin in non-Wnt activated tumors surprisingly enhances the sensitivity of those tumors to immunotherapy. FIG. 4D.

Finally, the combination therapy was evaluated in 4T1 tumor cells (murine breast), a Wnt activated cell line. Balb/C mice were implanted with 4T1 tumor cells, and 4 days post implantation, the mice were randomized into four groups and treated with Placebo/BCAT1 or anti-PD-1/CTLA-4 antibodies as shown in FIG. 4C. Mice were administered two doses of Placebo or BCAT1 at 3 mg/kg (qdx2) on days 4 and 5. Twenty-four hours after the last dose, mice were administered the anti-PD-1/CTLA-4 antibodies intraperitoneally at 5 mg/kg on days 6 and 8. This combination dosing cycle was then repeated starting on day 10 and continuing through day 14. Tumor growth was monitored by measuring the tumor sizes over the course of the treatment period.

Figure 15A:
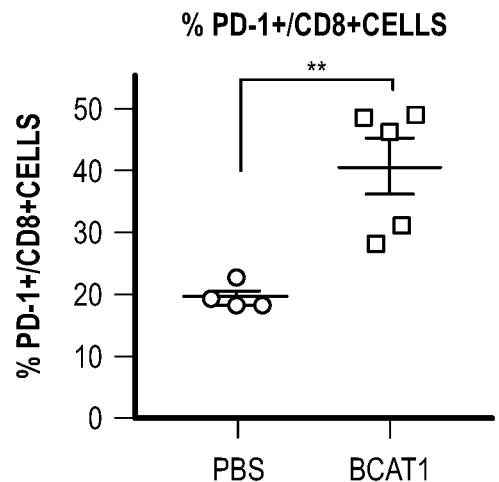
FIG. 15A-B show that a single treatment cycle with BCAT1 increases mRNA expression of Cxcl10, Cxcl11, and CD3 in mice implanted with the Wnt activated 4T1 tumors (A); and has minimal to no effect on tumor-associated natural killer (NK) cells or myeloid derived suppressor cells (MDSCs), but does increase Regulatory T-cells (Tregs) (B) in the tumor microenvironment.
Figure 15A:
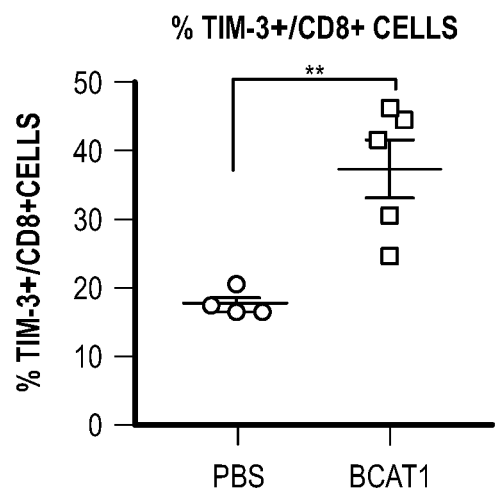
Figure 15A:
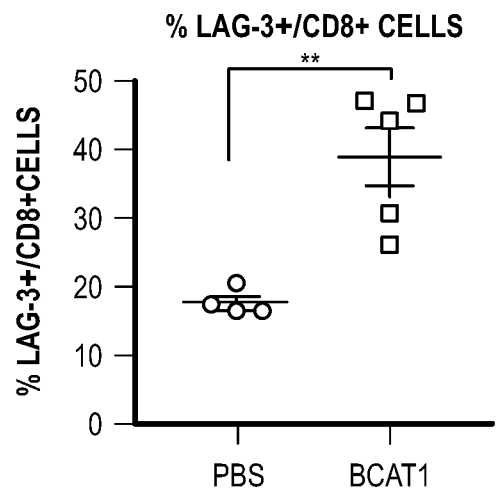
Figure 15B:
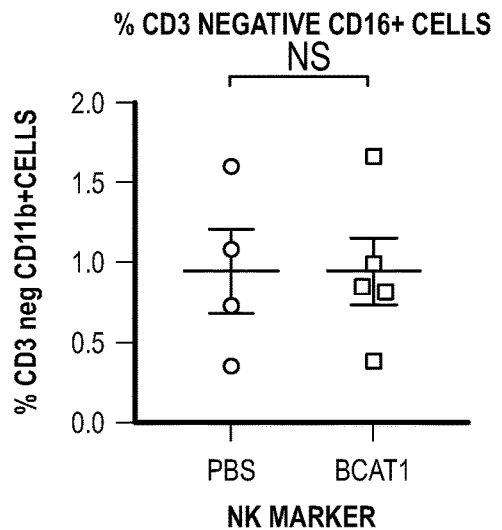
Figure 15B:
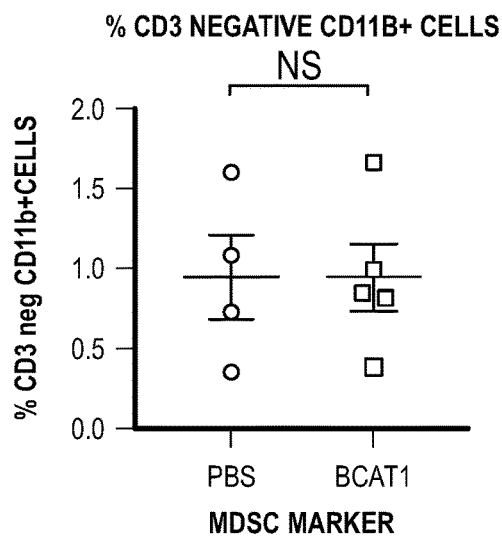
Figure 15B:
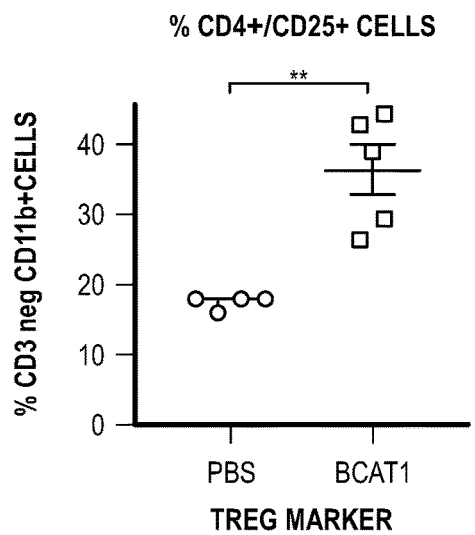

Because 4T1 tumors are Wnt active, treating mice with BCAT1 alone caused tumor growth inhibition. FIG. 4C. However, combining BCAT1 with anti-PD-1/CTLA-4 antibodies resulted in significant tumor growth inhibition compared to either agent alone. FIG. 4C. These results demonstrate that inhibiting β-catenin inhibition in a Wnt activated tumor enhances the sensitivity of those tumors to immunotherapy. Interestingly, flow cytometry data from Wnt-activated 4T1 tumors shows that BCAT1 treatment increases TCR cofactors known to be checkpoints within CD8+ T-cells: PD-1, TIM-3 and LAG-3 (FIG. 15A), as was observed with the non-Wnt activated tumor, B16F10. Similarly, there were no observed treatment-related effects on tumor-associated NK cells or immunosuppressive MDSCs (FIG. 15B), although there was an increase in TREGs upon DCR-BOAT treatment.

Example 6: Expression of Cytotoxic T Cell Markers Following Combination of β-Catenin Inhibition and Immunotherapy After the completion of the combination therapy study in the B16F10 tumor model, tumors were collected and analyzed by immunohistochemistry to measure the expression levels of granzyme B and perforin, which are released by CD8+ cytotoxic T cells upon recognition of antigen on the surface of a target cell (e.g., tumor cell). Following release, granzyme B and perforin are endocytosed by tumor cells. Perforin molecules promote endosomal pore formation, allowing granzyme B to enter the cytosol. Once in the cytosol of the tumor cell, granzyme B activates pro-apoptotic Bcl-2 family members and caspases via site-specific protease activity and mediate apoptosis. The perforin-mediated pores can be visualized by electron microscopy. In certain instances, the pores are large enough to be visualized without microscopy.

Figure 5:
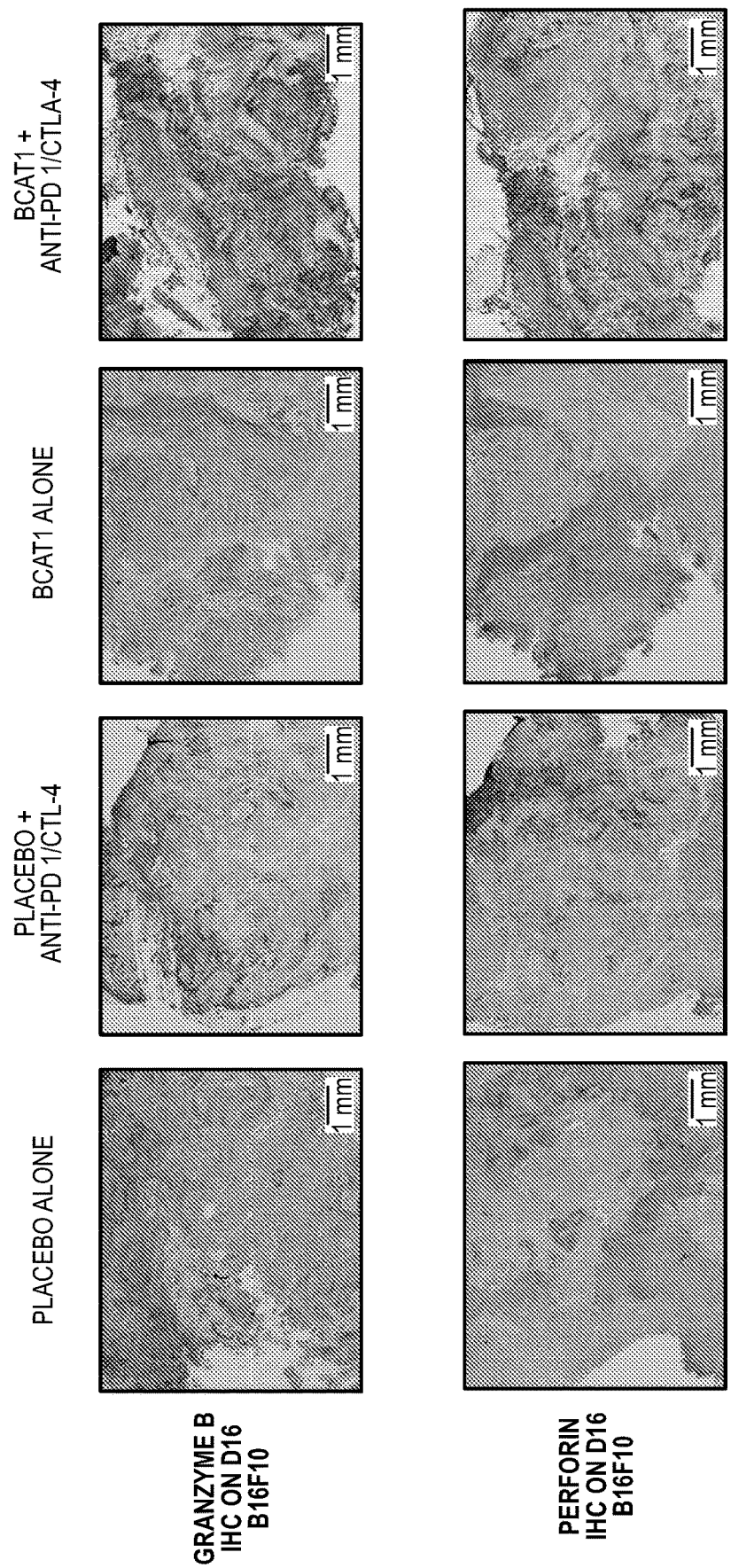
FIG. 5 shows by immunohistochemistry that combining BCAT1 and immunotherapy (10) enhances the release of perforin and granzyme B from CD8 cytotoxic T cells in B16F10 tumor cells.

BF16F10 tumors from mice treated with a combination of BCAT1 and anti-PD-1/CTLA4 antibodies expressed high levels of both granzyme B and perforin as compared to tumors from mice treated with either BCAT1 alone or Placebo and anti-PD-1/CTLA4 antibodies. FIG. 5. Tumors from mice treated with Placebo alone had extremely low levels of granzyme or perforin expression, suggesting that the significant reduction of tumor growth observed in the mice receiving combination therapy was associated with massive T cell infiltration of the tumor microenvironment. The tumors were also analyzed for pore formation resulting from the release of perforin from cytotoxic T cells. Pore formation was observed in tumors treated with either 1) Placebo and anti-PD-1/CTLA4 antibodies or 2) BCAT1 and anti-PD-1/CTLA4 antibodies, but was more pronounced in the mice treated with BCAT1 and anti-PD-1/CTLA4 antibodies (data not shown).

Example 7: Combination of β-Catenin Inhibition and Immunotherapy Reduces Tumor Growth in Small and Large MMTV-Wnt1 Tumors To see if β-catenin inhibition enhances T cell infiltration and potentiates the effect of immunotherapy in spontaneous tumors, the MMTV-Wnt1 model was utilized. In this model, mammary gland specific overexpression of Wnt1 with MMTV-LTR leads to spontaneous breast tumors with activated Wnt/β-catenin signaling.

Figure 6A:
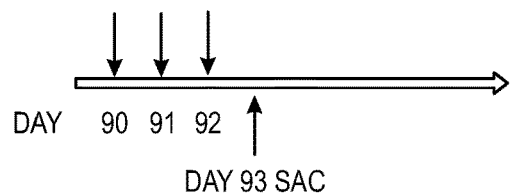
FIG. 6A shows the treatment schedule of mice with spontaneous MMTV-Wnt tumors that were treated with PBS or BCAT1, as described in Example 7.
Figure 6B:
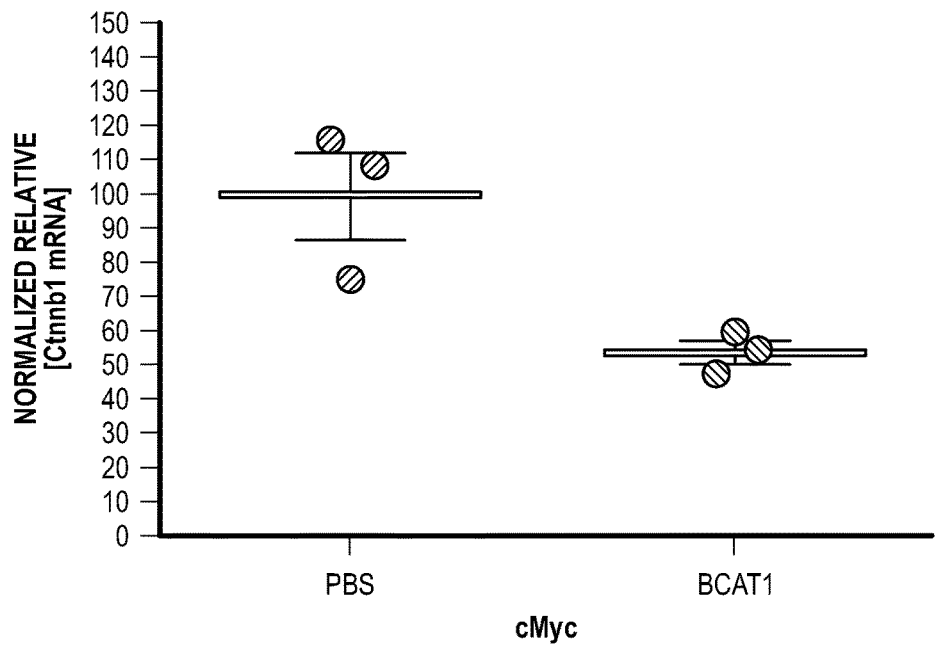
FIGS. 6B-F show that a single treatment cycle with BCAT1 in mice with spontaneous MMTV-Wnt1 tumors leads to reduced levels of β-catenin (Ctnnb1) and c-Myc mRNA as measured by qPCR (B); reduced β-catenin protein expression as measured by immunohistochemistry (IHC) (C); increased CD8 expression in the tumor microenvironment as measured by IHC (D); and reduced tumor growth (E); and that large tumors in mice initially treated with placebo respond to treatment with BCAT1 (F).
Figure 6B:
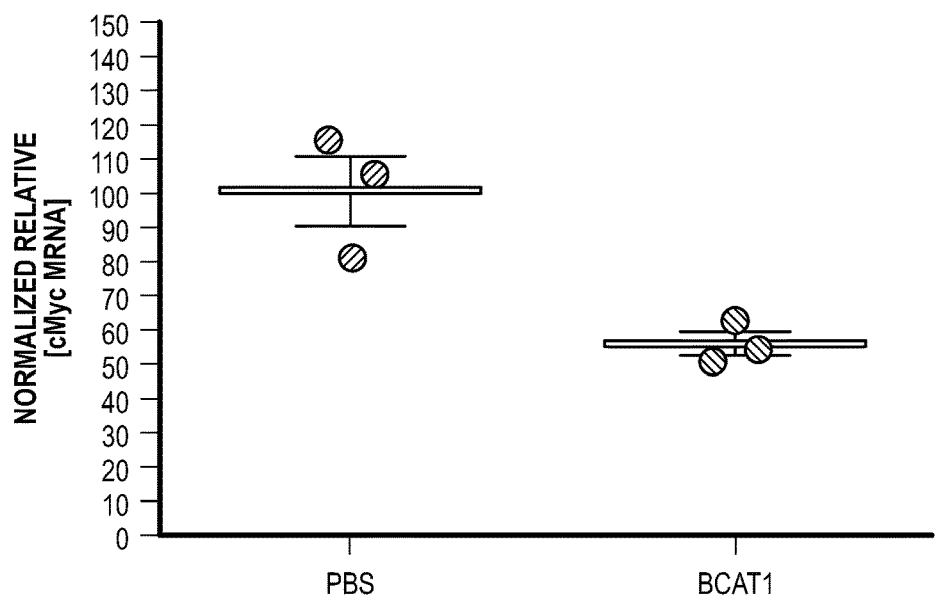
Figure 6C:
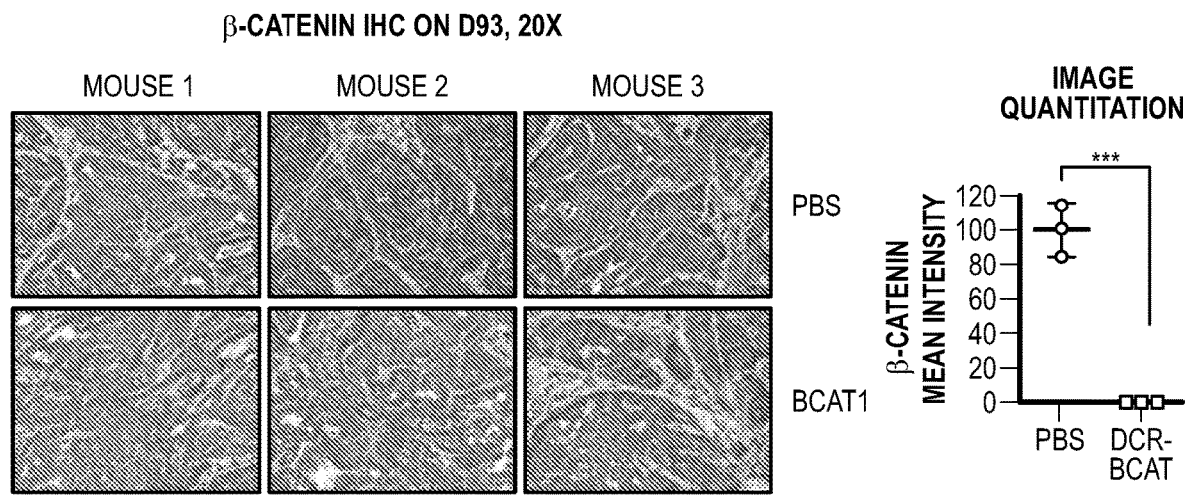

Initially, at day 90 (3 months from birth), mice were treated with BCAT1 at 5 mg/kg (qdx3). Twenty-four hours after the last injection, tumor β-catenin and cMyc mRNA levels were determined by qPCR. Unlike non-Wnt activated tumors, reducing β-catenin mRNA levels led to a reduction in the cMyc mRNA levels of these Wnt activated tumors, as expected. FIG. 6. β-catenin protein levels were measured by immunohistochemistry and were also reduced in tumors treated with BCAT1, as expected. FIG. 6C. Control tumors treated with PBS show nuclear localization of β-catenin, a hallmark of Wnt activated tumors, which was reversed by a single cycle of BCAT1 treatment, resulting in almost complete depletion of β-catenin protein. FIG. 6C.

Figure 6D:
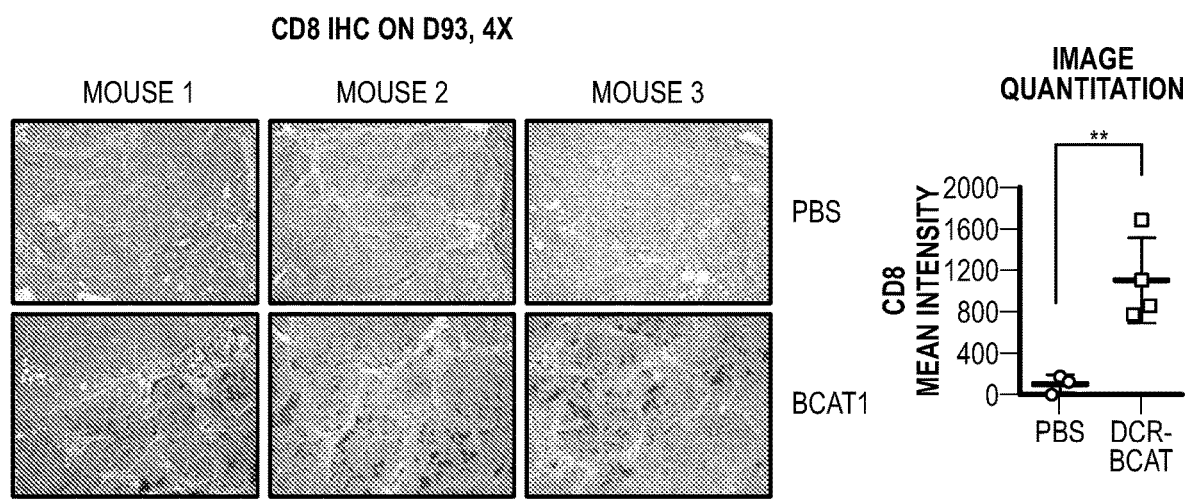

In addition, to see if β-catenin inhibition affects CD8 T cell infiltration, CD8 expression was measured by immunohistochemistry in the same tumors. FIG. 6D. CD8+ T cell infiltrates were visible in multiple areas of each tumor section and the same pattern was confirmed in the tumors of every animal. As shown in FIGS. 6C and 6D, the almost complete depletion of β-catenin protein correlated with higher levels of CD8 T cells, suggesting that the β-catenin inhibition increases T cell infiltration in these spontaneously grown tumors.

Figure 6E:
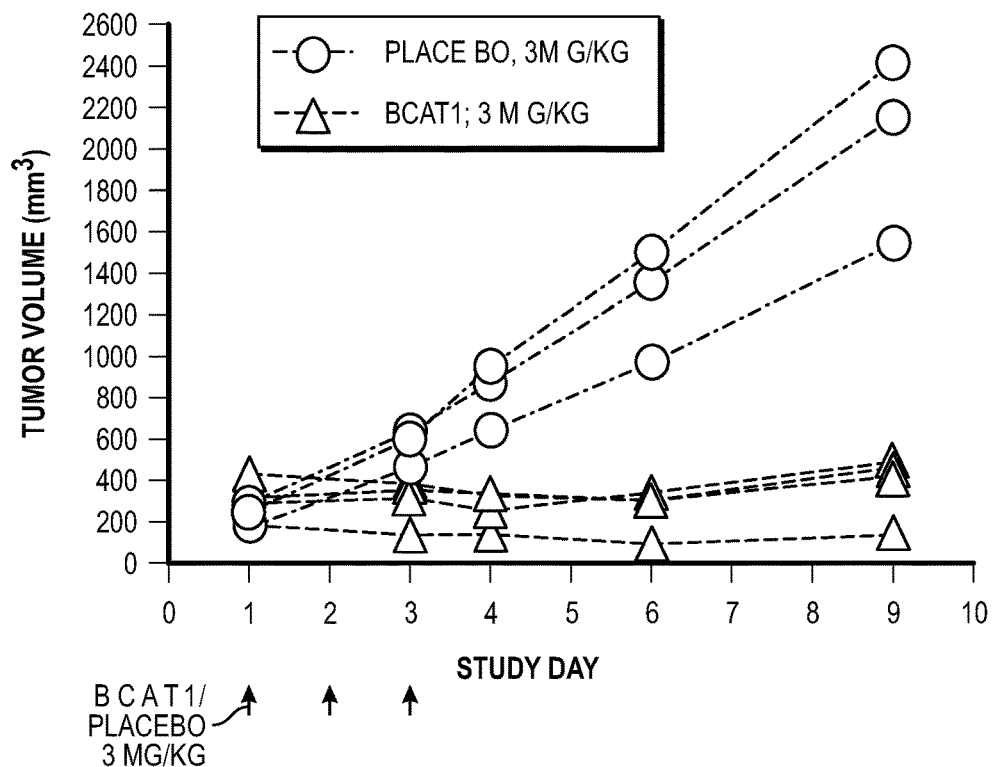
Figure 6F:
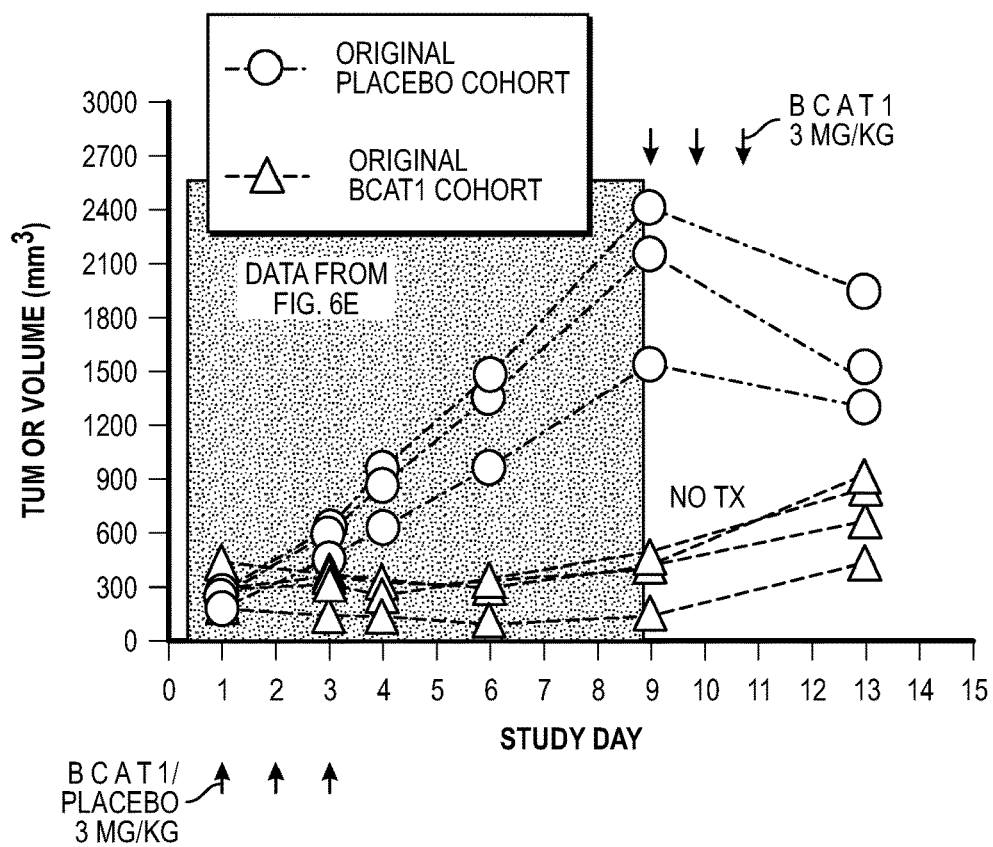

The efficacy of BCAT1 monotherapy was evaluated in these spontaneous tumors by treating one group of mice (n=4) with BCAT1 and another group (n=3) with Placebo (qdx3, 3 mg/kg). A single cycle of BCAT1 treatment resulted in complete tumor growth inhibition as compared to mice treated with Placebo. FIG. 6E. By day 9, the tumors treated with Placebo had grown sizably. These large tumors were then treated with a single cycle of BCAT1 (qdx3, 3 mg/kg), starting at day 9. As shown in FIG. 6F, even these large tumors responded to BCAT1, suggesting that β-catenin inhibition in these large tumors inhibited tumor growth.

Figure 7:
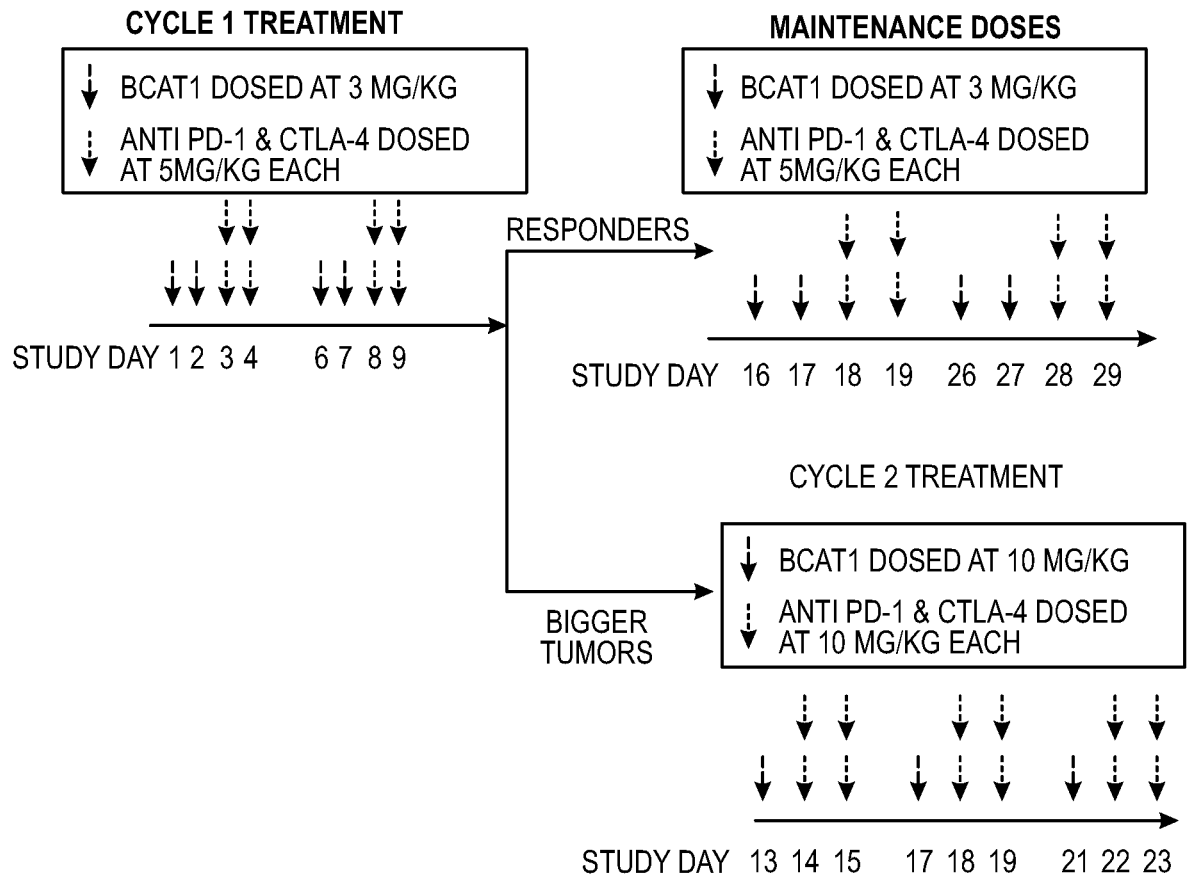
FIG. 7 shows the combination therapy treatment schedules used in Example 7. Mice were treated according to Cycle 1 followed by either a maintenance dose schedule (for mice that responded to Cycle 1 treatment) or treatment according to Cycle 2 (for mice having large tumors following Cycle 1 treatment).

To see if combining β-catenin inhibition with immunotherapy would further improve the anti-tumor efficacy in these spontaneous tumors, another study was conducted using mice with an average tumor size of about 500-600 mm$^3$. Because these spontaneous tumors grow at different times, mice with an average tumor size of about 500-600 mm$^3$ were recruited for the study at different times. Two groups of mice received Placebo (n=2 and n=3) and another two groups of mice (n=3 and n=5) received BCAT1 at 3 mg/kg (qdx2) on days 1 and 2. Following treatment with BCAT1 or Placebo, one of the groups from each treatment (n=2 and n=5) received anti-PD-1/CTLA-4 antibodies at 5 mg/kg for each antibody (qdx2) on days 3 and 4. Forty-eight hours later, all four groups were subjected to the same treatment schedule and tumor growth was monitored until day 13, as shown in FIG. 7.

Figure 8:
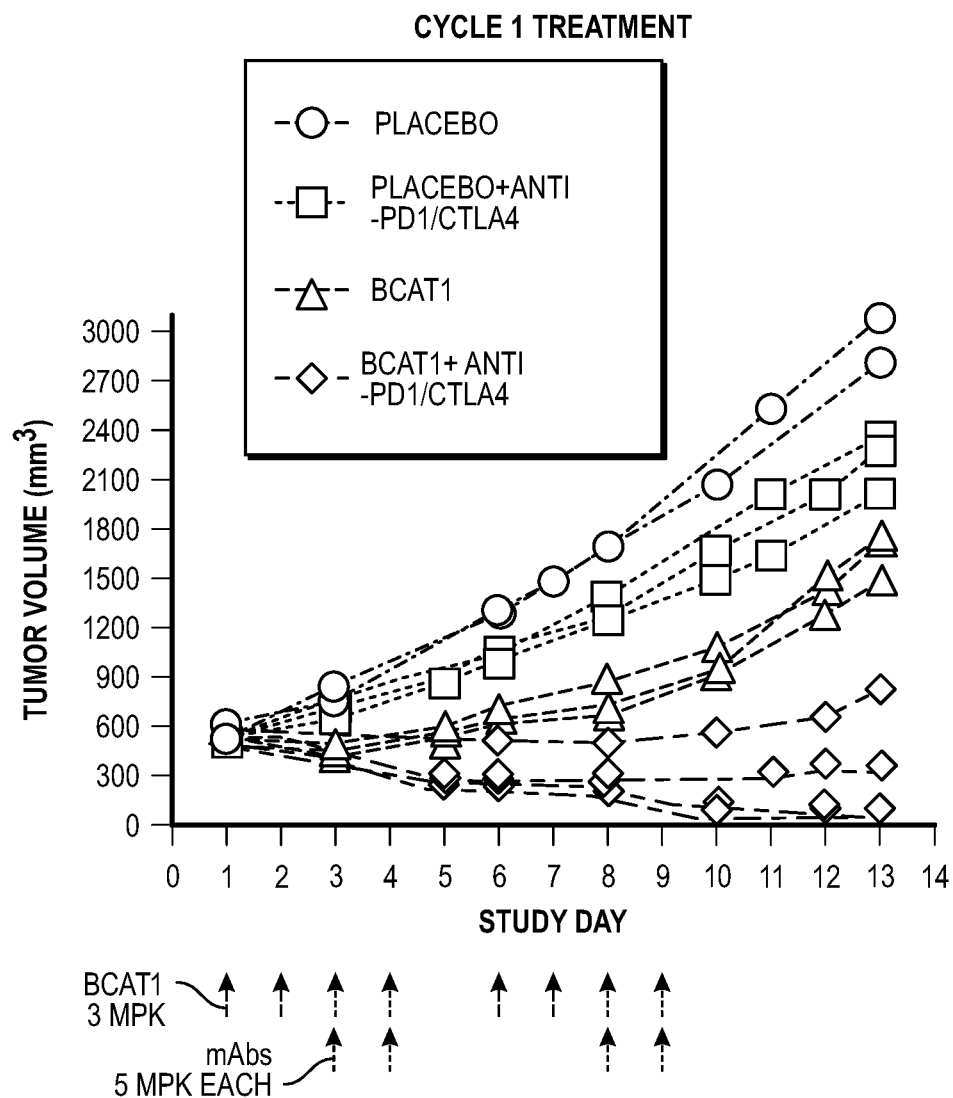
FIG. 8 shows that combination therapy with BCAT1 and anti-PD-1/CTLA-4 antibodies according to the Cycle 1 treatment schedule in mice with spontaneous MMTV-Wnt1 tumors resulted in complete tumor regression in 3 of 4 animals treated.

Mice that received Placebo had significant tumor growth, while mice that received Placebo and anti-PD-1/CTLA-4 antibodies showed a slight reduction in tumor growth as compared to the Placebo alone. FIG. 8. Mice receiving BCAT1 alone demonstrated modest efficacy in reducing tumor growth, while the mice treated with both BCAT1 and anti-PD-1/CTLA-4 antibodies demonstrated potent inhibition of tumor growth, as shown in FIG. 8. Remarkably, in three out of the five mice treated with the combination of BCAT1 and immunotherapy, the tumors completely regressed. The remaining animal in that group, although it responded significantly compared to mice in any of the other groups, did not perform as well as the other three mice receiving combination therapy, likely reflecting heterogeneity that is expected in spontaneous tumor growth settings and may also be present in clinical settings.

The four mice with large tumors following the first cycle of treatment (FIG. 9A) were subjected to a second cycle of treatment with BCAT1 and immunotherapy at higher doses to see how those larger tumors responded to the combination therapy. These mice were treated with BCAT1 at 10 mg/kg, starting on day 13, followed by anti-PD-1/CTLA-4 antibodies at 10 mg/kg for each antibody (qdx2) on days 14 and 15. The treatment schedule was repeated two more times, starting at days 17 and 21, and tumor growth was monitored until day 24 as shown in FIG. 7. Tumors in all four mice responded and regressed after the combination treatment (FIG. 9B), showing that the inhibition of β-catenin mediated by BCAT1 sensitizes these larger tumors to checkpoint inhibitors, presumably by enhancing infiltration of T-cells at the tumor site.

The three mice with complete regression following the first cycle of treatment (see FIG. 9A) were subjected to maintenance doses, starting on day 16. The mice were treated with BCAT1 at 3 mg/mg (qdx2) on days 16 and 17, followed by anti-PD-1/CTLA-4 antibodies at 5 mg/kg for each antibody (qdx2) on days 18 and 19. FIG. 7. The mice were subjected to the same treatment schedule, starting on day 26, and tumor growth was monitored until day 31, as shown in FIGS. 9A and 9C. Mice receiving the maintenance doses remained tumor free throughout the course of the study, as shown in FIG. 9A. The kinetics of tumor regression in these mice is also shown in FIG. 9C, which is a blown up version of the BCAT1+anti-PD-1/CTLA-4 data in FIG. 9A.

Example 8: Indirect Wnt Pathway Targeting is not Sufficient for Converting Cold Non-Wnt Activated Tumors into Hot Tumors While BCAT1 targets β-catenin directly via post-transcriptional mRNA silencing, several clinical-stage Wnt pathway modulators are being evaluated for their ability to promote antitumor efficacy through indirect β-catenin inhibition ((Zhan et al; 2017, Oncogene, 36(11):1461-73; Schatoff et al; 2017, Curr Colorectal Cancer Rep, 13(2):101-10; Novellasdemunt et al; 2015, Am J Physiol Cell Physiol, 309(8): C511-21 and Zhang et al; 2015, Am J Cancer Res, 5(8): 2344-60). One such investigational drug (and arguably the most clinically advanced), LGK-974, is an inhibitor of the PORCN acetyltransferase, an enzyme that is required for secretion of Wnt ligands (Liu et al; 2013, Proceedings of the National Academy of Sciences of the United States of America, 110(50): 20224-9). LGK-974 has been in multiple clinical trials, including in combination with anti-PD-(L)1 for evaluation as a potentiator of immune checkpoint inhibition.

The ability of LGK-974 and BCAT1 to convert cold tumors to hot tumors by promoting T-cell infiltration was compared. To perform this comparison, mice harboring two relevant tumor types were used: Wnt-active tumors driven by overexpression of a Wnt ligand and therefore predicted to be responsive to LGK-974 (MMTV-Wnt1 model), and non-Wnt activated tumors (B16F10). This analysis utilized Axin2 mRNA as a surrogate for Wnt activity, due to its excellent correlation with Wnt signatures and nuclear β-catenin in humans and Cd8a mRNA to monitor tumor T-cell content.

Figure 16A:
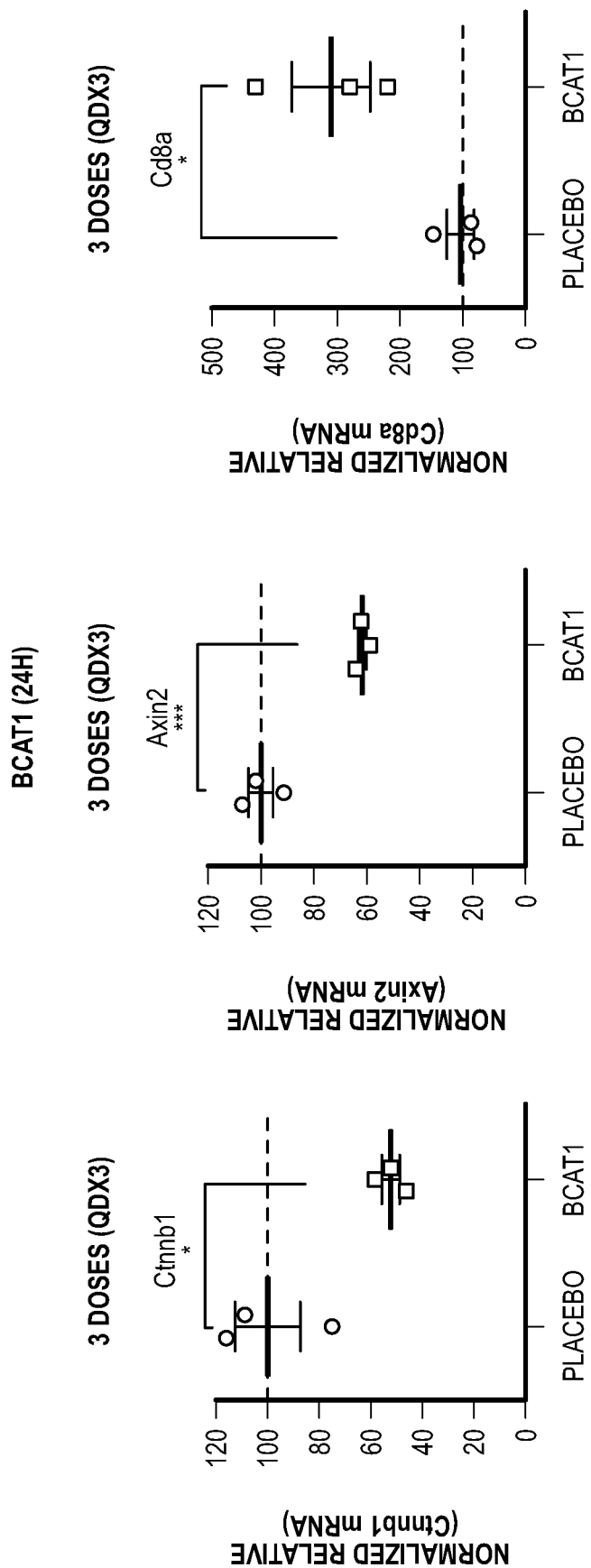
FIGS. 16A-C show the ability of BCAT1 (three doses of qdx3) (A), and high dose LGK-974 (three doses qdx3) (C) to significantly enhance CD8 mRNA expression in mice harboring MMTTV-Wnt tumors. Low dose LGK-974 (single dose of qdx1) also enhances CD8 mRNA expression in those mice but to a lesser extent than BCAT1 or high dose LGK-974 (B). Both BCAT1 and LGK-974 reduce Axin2 mRNA expression, although the BCAT1-induced reduction of Axin2 mRNA is better sustained through 24 hours. LGK-974 has no effect on β-catenin (Ctnnb1) mRNA expression.
Figure 16B:
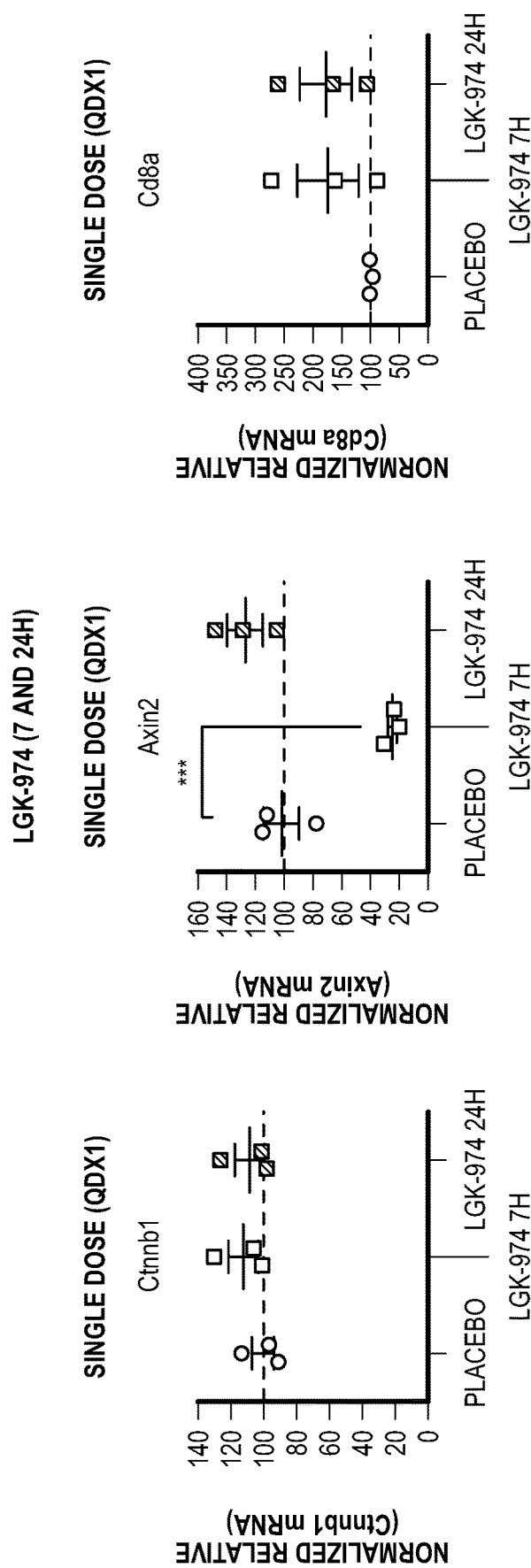
Figure 16C:
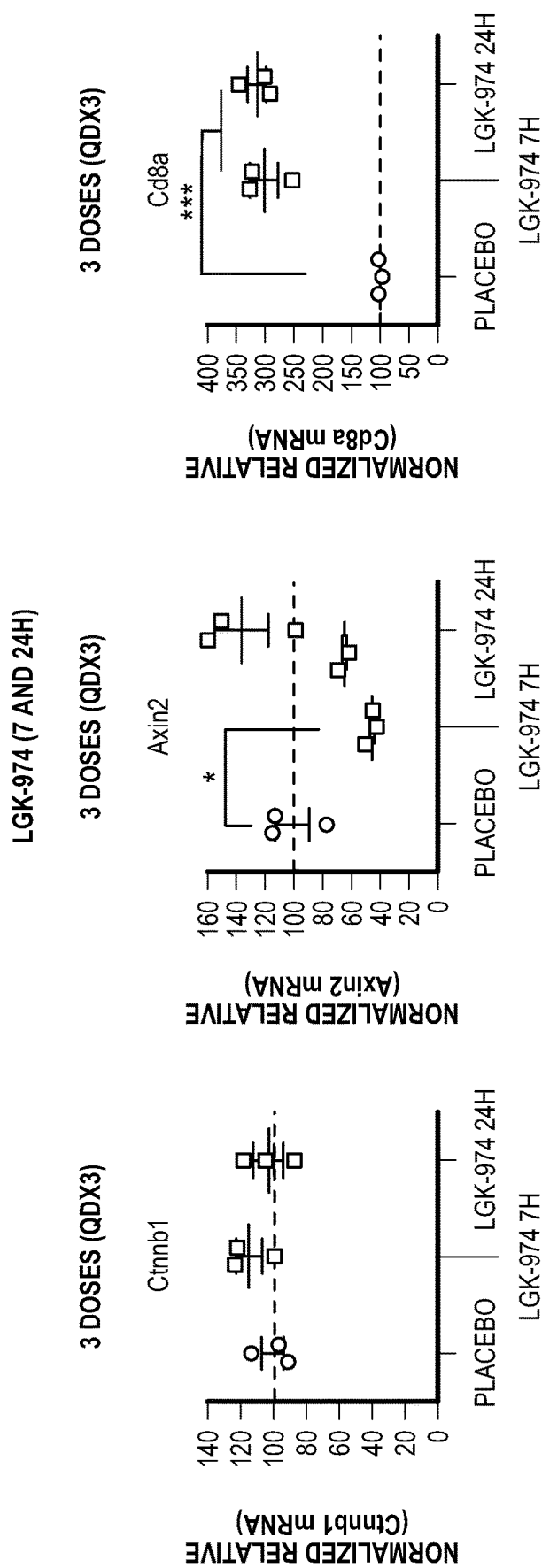

In MMTV-Wnt1 tumors, the Wnt effector Axin2 is suppressed by both BCAT1 and LGK-974 at dose levels previously reported to be efficacious (FIG. 16A). The pharmacodynamic response to LGK-974, however, is very transient as previously shown (Liu et al; 2013, Proceedings of the National Academy of Sciences of the United States of America, 110(50): 20224-9) presumably due to its pharmacokinetic properties; Axin2 mRNA returns to baseline by 24 h after treatment (FIGS. 16A-B). Increasing the frequency of LGK-974 dosing induces variable results but does appear to provide some improvement in the duration of Axin2 inhibition (FIG. 16C). Predictably, only BCAT1 directly affects Ctnnb1 mRNA levels as LGK-974 does not target Ctnnb1 mRNA or β-catenin protein directly (FIGS. 16A-C). Importantly, Cd8a mRNA elevation is observed after both direct and indirect inhibition with BCAT1 and LGK-974, respectively. T-cell elevation appears to be variable but sustained 24 h after LGK-974 treatment, suggesting that even a transient dampening of Wnt activity is sufficient for this mechanism (FIGS. 16A-C). However, the T-cell response is far more robust and consistent between animals after repeat dosing of LGK-974, compared to a single administration (FIGS. 16B-C). These data suggest that suppression of β-catenin by direct or indirect pharmacological intervention is sufficient to overcome its immune evasion function in tumors that are driven by Wnt ligand defects, although such genetic lesions are relatively uncommon in humans (Zhan et al; 2017, Oncogene, 36(11):1461-73).

Figure 17:
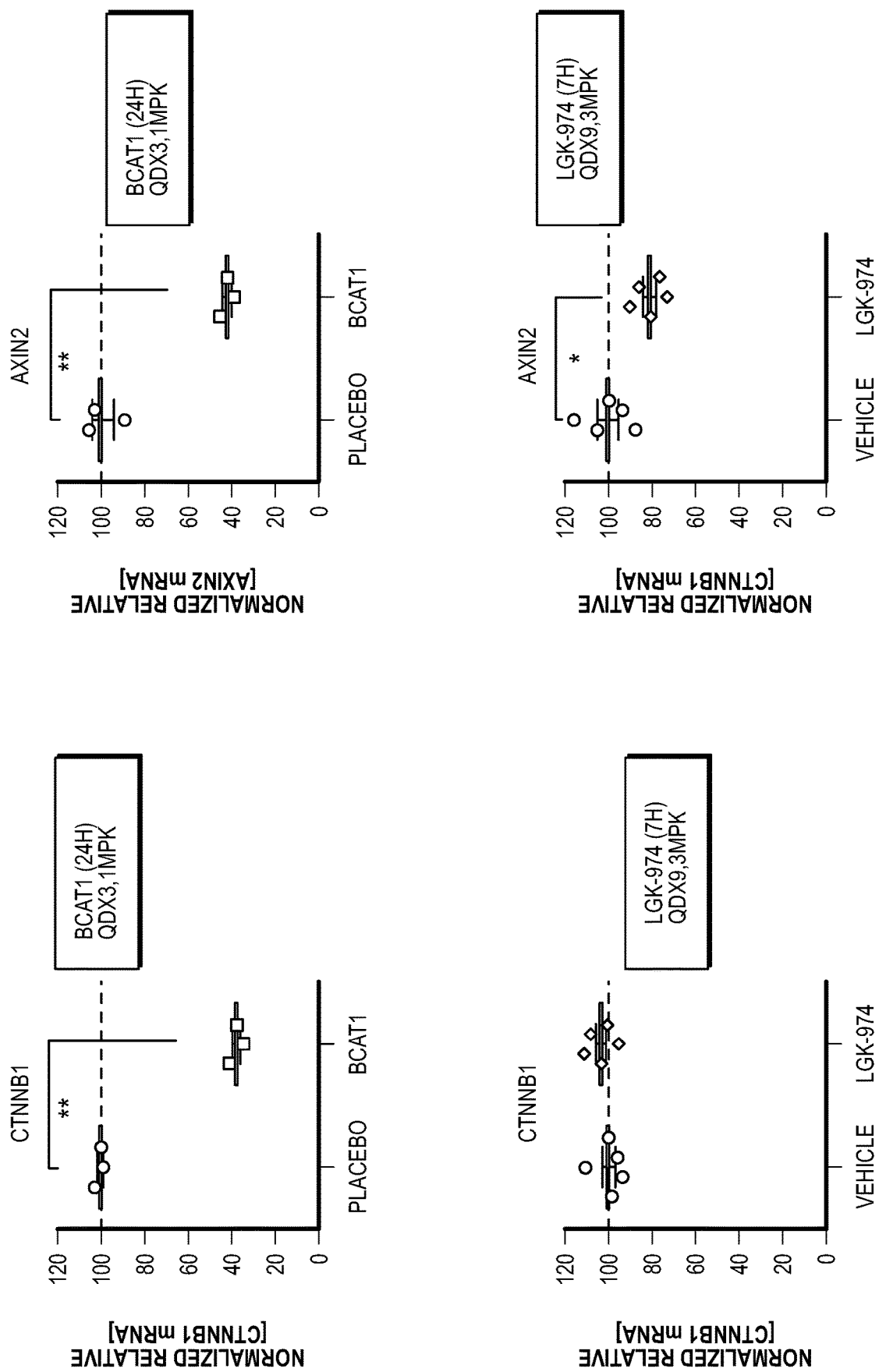
FIG. 17 shows that BCAT1 reduces expression of both Ctnnb1 and Axin2 in human tumor xenografts harboring an APC loss-of-function mutation and that LGK-974 causes only a slight, transient reduction of Axin2 in such tumors even at highly exaggerated dose levels.

One limitation of LGK-974 is that, as an inhibitor of Wnt ligand secretion, it is expected to be generally ineffective against the majority of Wnt-activated tumors. This is because most tumors in this category are driven by downstream genetic lesions such as APC, which is by far the most common mutation found in colorectal tumors. Indeed, while BCAT1 reduces expression of both CTNNB1 (67%) and AXIN2 (58%) in human tumor xenografts harboring an APC loss-of-function mutation, LGK-974 caused only a slight, transient reduction of AXIN2 (19%) in such tumors even at highly exaggerated dose levels of 9 daily doses of 3 mg/kg (FIG. 17). These data further highlight the broad potential of directly inhibiting β-catenin expression.

Figure 18A:
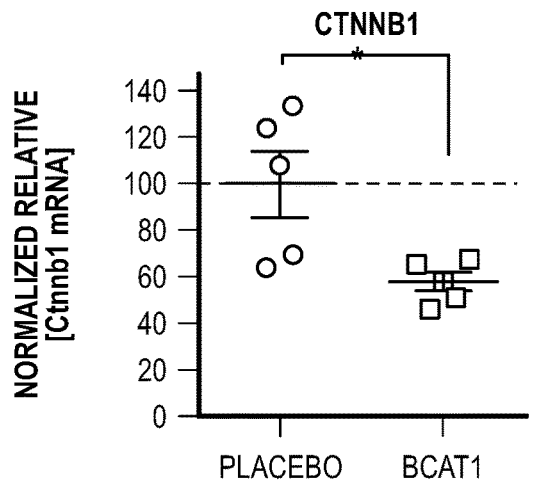
FIGS. 18A-B show that in mice implanted with non Wnt-activated B16F10 tumors, BCAT1 treatment reduces Ctnnb1 mRNA but has no effect on Axin2 mRNA (A), and that LGK-974 is unable reduce Axin2 mRNA expression or increase Cd8a mRNA expression in this non-Wnt activated tumor (B).
Figure 18A:
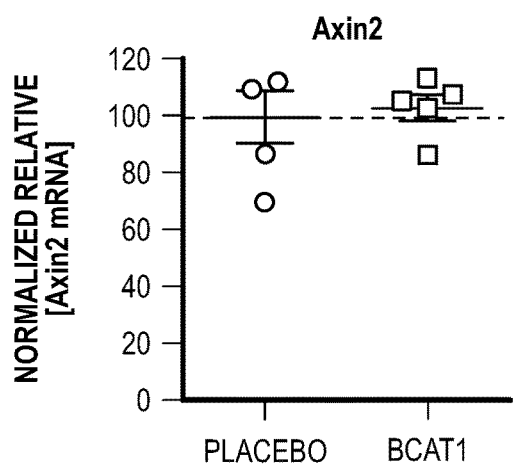
Figure 18A:
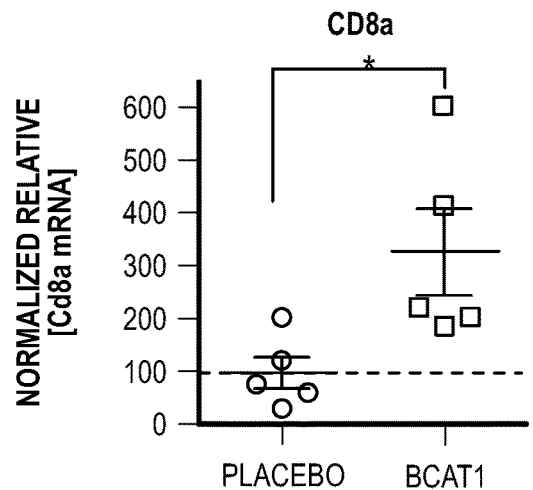
Figure 18B:
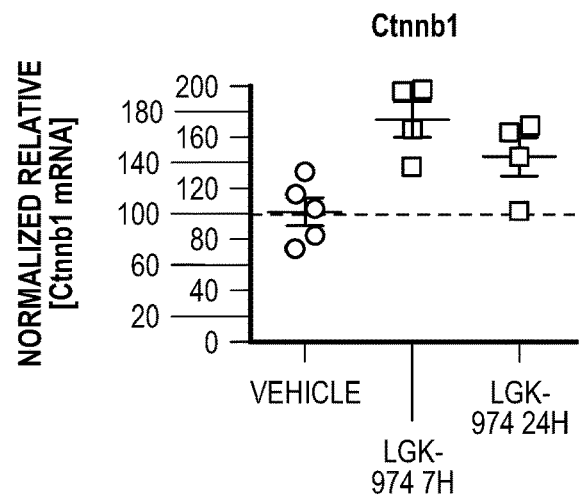
Figure 18B:
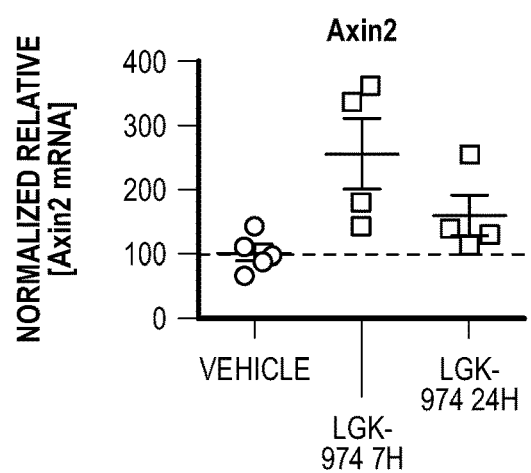
Figure 18B:
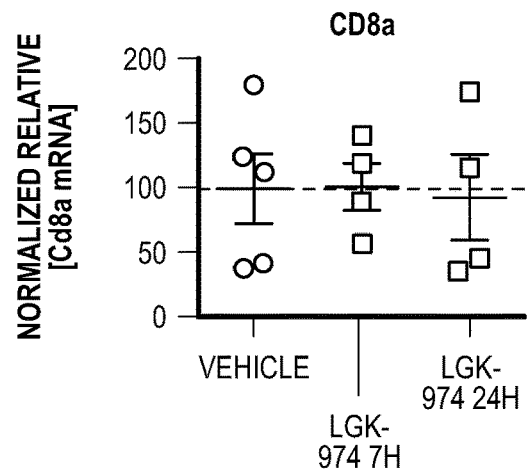

In non Wnt-activated B16F10 tumors, BCAT1 treatment demonstrates similar reduction of Ctnnb1 mRNA but no effect on Axin2 mRNA, as predicted given the lack of steady state nuclear β-catenin (FIG. 18A). Despite the lack of direct transcriptional effects, direct inhibition of β-catenin by BCAT1 enhanced Cd8a mRNA expression in B16F10 tumors. To the contrary, LGK-974 was unable to promote an increase in Cd8a mRNA, showing that pathway perturbation at the level of Wnt ligand secretion does not promote immune modulation in contexts where β-catenin function is not dysregulated (FIG. 18B). These stark differences suggest that the broad applicability of direct β-catenin inhibitors, like the β-catenin nucleic acid inhibitor molecules described herein, in potentiating immunotherapy across tumors of diverse genetic origin does not extend to indirect Wnt pathway modulators, like LGK-974.

What is claimed is:

1. A method of treating cancer in a subject, comprising administering to the subject:
 a therapeutically effective amount of a β-catenin nucleic acid inhibitor molecule, wherein said nucleic acid inhibitor molecule is a double stranded RNAi, wherein the sense strand of said RNAi comprises or consists of the sequence of SEQ ID NO:1; and
 a therapeutically effective amount of an immunotherapeutic agent.

2. The method of claim 1, wherein the subject is a human.

3. The method of claim 1, wherein the cancer is a non-Wnt activated cancer.

4. The method of claim 1, wherein the cancer is a Wnt activated cancer.

5. The method of claim 1, wherein the β-catenin nucleic acid inhibitor molecule is a double stranded RNAi inhibitor molecule.

6. The method of claim 1, wherein the antisense strand includes a single-stranded overhang of 1-5 nucleotides at its 3' terminus.

7. The method of claim 6, wherein the antisense strand of the double stranded RNAi inhibitor molecule further comprises a single-stranded overhang of 1-10 nucleotides at its 5' terminus.

8. The method of claim 1, wherein the β-catenin nucleic acid inhibitor molecule is a double stranded RNAi inhibitor molecule comprising a sense and an antisense strand and a region of complementarity between the sense strand and the antisense strand of 26 base pairs, wherein the sense strand is 26 nucleotides in length and wherein the antisense strand is 38 nucleotides in length and includes a single-stranded overhang of 2 nucleotides at its 3' terminus and a single-stranded overhang of 10 nucleotides at its 5' terminus.

9. The method of claim 1, wherein the antisense strand comprises or consists of the sequence of SEQ ID NO: 2.

10. The method of claim 1, wherein the β-catenin nucleic acid inhibitor molecule contains a tetraloop.

11. The method of claim 1, wherein the immunotherapeutic agent is an antagonist of an inhibitory immune checkpoint molecule or an agonist of a co-stimulatory checkpoint molecule.

12. The method of claim 11, wherein the immunotherapeutic agent is an antagonist of an inhibitory check point, and the inhibitory check point is PD-1 or PD-L1.

13. The method of claim 11, wherein the antagonist of the inhibitory immune checkpoint molecule or the agonist of the co-stimulatory checkpoint molecule is a monoclonal antibody.

14. The method of claim 13, wherein the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

15. A method of treating cancer in a human subject, comprising administering to the human subject:
 a therapeutically effective amount of a β-catenin nucleic acid inhibitor molecule, wherein the β-catenin nucleic acid inhibitor molecule is a double stranded RNAi inhibitor molecule comprising a sense and an antisense strand and a region of complementarity between the sense strand and the antisense strand, wherein the sense strand comprises or consists of the sequence of SEQ ID NO:1 and the antisense strand comprises or consists of the sequence of SEQ ID NO: 2; and
 a therapeutically effective amount of an immunotherapeutic agent, wherein the immunotherapeutic agent comprises an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

16. The method of claim 1, wherein the β-catenin nucleic acid inhibitor molecule is formulated with a lipid nanoparticle.

17. The method of claim 16, wherein the lipid nanoparticle comprises a cationic lipid and a pegylated lipid.

18. The method of claim 1, wherein the subject has been identified as having the non-Wnt activated cancer before the administering step.

19. The method of claim 1, further comprising before the administering step, a step of analyzing a tumor sample from the subject to determine if the subject has the non-Wnt activated cancer.

20. The method of claim 1, wherein the non-Wnt activated cancer is resistant to treatment with the immunotherapeutic agent when the immunotherapeutic agent is not administered in combination with the β-catenin nucleic acid inhibitor molecule.

21. The method of claim 1, wherein the non-Wnt activated cancer is a melanoma, a neuroblastoma, or a renal cancer.

22. A method of potentiating a therapeutic effect of an immunotherapeutic agent against a cancer, comprising administering to a subject having the cancer a β-catenin nucleic acid inhibitor molecule in an amount sufficient to potentiate the therapeutic effect of the immunotherapeutic agent against the cancer, wherein said β-catenin nucleic acid inhibitor molecule is a double stranded RNAi, wherein the sense strand of said RNAi comprises or consists of the sequence of SEQ ID NO:1.

23. The method of claim 22, wherein the cancer is a Wnt activated cancer.

24. The method of claim 22, wherein the cancer is a non-Wnt activated cancer.

25. The method of claim 22, wherein prior to administering the β-catenin nucleic acid inhibitor molecule, the cancer is associated with a non-T cell inflamed phenotype that is resistant to immunotherapy and wherein administering the β-catenin nucleic acid inhibitor molecule converts the non-T cell inflamed phenotype into an T cell-inflamed phenotype that is responsive to an immunotherapeutic agent.

26. The method of claim 22, wherein the immunotherapeutic agent is an antagonist of an inhibitory immune checkpoint molecule or an agonist of a co-stimulatory checkpoint molecule.

27. The method of claim 26, wherein the immunotherapeutic agent is an antagonist of an inhibitory check point, and the inhibitory check point is PD-1 or PD-L1.

28. The method of claim 26, wherein the antagonist of the inhibitory immune checkpoint molecule or the agonist of the co-stimulatory checkpoint molecule is a monoclonal antibody.

29. The method of claim 28, wherein the monoclonal antibody is an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

* * * * *

SEQUENCE LISTING

<160> NUMBER OF SEQ ID NOS: 3

<210> SEQ ID NO 1
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
agaauacaaa ugauguagaa acagcc                                          26

<210> SEQ ID NO 2
<211> LENGTH: 38
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uagcuaucgt ggcuguuucu acaucauuug uauucugc                              38

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15
```